US010363320B2

(12) United States Patent
Jung et al.

(10) Patent No.: US 10,363,320 B2
(45) Date of Patent: *Jul. 30, 2019

(54) CONJUGATE COMPRISING OXYNTOMODULIN AND AN IMMUNOGLOBULIN FRAGMENT, AND USE THEREOF

(71) Applicant: HANMI SCIENCE CO., LTD, Hwaseong-si, Gyeonggi-Do (KR)

(72) Inventors: Sung Youb Jung, Suwon-si (KR); Dae Jin Kim, Hwaseong-si (KR); Sung Hee Park, Seoul (KR); Young Eun Woo, Daejeon (KR); In Young Choi, Yongin-si (KR); Se Chang Kwon, Seoul (KR)

(73) Assignee: Hanmi Science Co., Ltd., Hwaseong-Si, Gyeonggi-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/636,160

(22) Filed: Jun. 28, 2017

(65) Prior Publication Data
US 2017/0340753 A1    Nov. 30, 2017

Related U.S. Application Data

(62) Division of application No. 14/126,914, filed as application No. PCT/KR2012/004722 on Jun. 15, 2012, now Pat. No. 9,731,031.

(30) Foreign Application Priority Data

Jun. 17, 2011   (KR) ........................ 10-2011-0058852

(51) Int. Cl.
| | | |
|---|---|---|
| A61K 47/68 | (2017.01) | |
| C07K 14/575 | (2006.01) | |
| A61K 45/06 | (2006.01) | |
| A61K 38/26 | (2006.01) | |
| A61K 47/60 | (2017.01) | |
| A61P 3/04 | (2006.01) | |
| A61K 38/00 | (2006.01) | |

(52) U.S. Cl.
CPC .......... *A61K 47/6889* (2017.08); *A61K 38/26* (2013.01); *A61K 45/06* (2013.01); *A61K 47/60* (2017.08); *A61K 47/68* (2017.08); *A61K 47/6801* (2017.08); *A61K 47/6811* (2017.08); *C07K 14/575* (2013.01); *A61K 38/00* (2013.01); *C07K 2319/30* (2013.01)

(58) Field of Classification Search
CPC .. C07K 14/575; C07K 2319/30; A61K 38/00; A61K 38/26; A61K 47/6811; A61K 47/6801; A61K 47/6889; A61K 47/68; A61K 47/60; A61K 45/06
See application file for complete search history.

(56) References Cited

U.S. PATENT DOCUMENTS

| | | |
|---|---|---|
| 6,776,983 B1 | 8/2004 | Sumida et al. |
| 7,217,845 B2 | 5/2007 | Rosen et al. |
| 7,521,424 B2 | 4/2009 | Rosen et al. |
| 7,737,260 B2 | 6/2010 | Kim et al. |
| 7,928,058 B2 | 4/2011 | Sinha et al. |
| 8,263,084 B2 | 9/2012 | Song et al. |
| 8,729,017 B2 | 5/2014 | DiMarchi et al. |
| 8,778,872 B2 | 7/2014 | DiMarchi et al. |
| 8,975,001 B2 | 3/2015 | Bae |
| 2003/0032588 A1 | 2/2003 | Marshall et al. |
| 2004/0087778 A1 | 5/2004 | Feige et al. |
| 2009/0053246 A1 | 2/2009 | Kim et al. |
| 2009/0238838 A1 | 9/2009 | Kim et al. |
| 2009/0297496 A1 | 12/2009 | Grabowski |
| 2009/0298757 A1 | 12/2009 | Bloom et al. |
| 2010/0144617 A1 | 6/2010 | Sinha Roy et al. |
| 2010/0190701 A1 | 7/2010 | Day et al. |
| 2010/0196405 A1 | 8/2010 | Ng |
| 2010/0330108 A1 | 12/2010 | Song et al. |
| 2011/0034374 A1 | 2/2011 | Bloom et al. |
| 2011/0065633 A1 | 3/2011 | DiMarchi et al. |
| 2011/0190200 A1 | 8/2011 | DiMarchi et al. |
| 2012/0003712 A1 | 1/2012 | Song et al. |
| 2012/0178670 A1 | 7/2012 | Riber et al. |
| 2012/0329707 A1 | 12/2012 | DiMarchi et al. |
| 2013/0035285 A1 | 2/2013 | Lau et al. |
| 2013/0122023 A1 | 5/2013 | Woo et al. |

FOREIGN PATENT DOCUMENTS

| | | |
|---|---|---|
| CN | 101213209 A | 7/2008 |
| CN | 101389648 A | 3/2009 |

(Continued)

OTHER PUBLICATIONS

Wynne et al, Subcutaneous Oxyntomodulin Reduces Body Weight in Overweight and Obese Subjects A Double-Blind Randomized, Controlled Trial, Diabetes, 2005, 54, pp. 2390-2395.

(Continued)

*Primary Examiner* — Karlheinz R. Skowronek
*Assistant Examiner* — Li N Komatsu
(74) *Attorney, Agent, or Firm* — BakerHostetler

(57) ABSTRACT

The present invention relates to a conjugate comprising oxyntomodulin, an immunoglobulin Fc region, and non-peptidyl polymer wherein the conjugate being obtainable by covalently linking oxyntomodulin to immunoglobulin Fc region via non-peptidyl polymer, and a pharmaceutical composition for the prevention or treatment of obesity comprising the conjugates. The conjugate comprising oxyntomodulin and the immunoglobulin Fc of the present invention reduces food intake, suppresses gastric emptying, and facilitates lipolysis without side-effects, unlike native oxyntomodulin, and also shows excellent receptor-activating effects and long-term sustainability, compared to native oxyntomodulin. Thus, it can be widely used in the treatment of obesity with safety and efficacy.

20 Claims, 33 Drawing Sheets
Specification includes a Sequence Listing.

(56) References Cited

FOREIGN PATENT DOCUMENTS

| | | |
|---|---|---|
| CN | 101578107 A | 11/2009 |
| CN | 101974077 A | 2/2011 |
| CN | 102010473 A | 4/2011 |
| CN | 102369209 A | 3/2012 |
| CN | 103732616 A | 4/2014 |
| CN | 103732618 A | 4/2014 |
| EP | 2300037 A2 | 3/2011 |
| EP | 2330124 A2 | 6/2011 |
| EP | 1891105 B1 | 4/2012 |
| JP | 2003-531632 A | 10/2003 |
| JP | 2008-543816 A | 12/2008 |
| JP | 2009-527558 A | 7/2009 |
| JP | 2009-203235 A | 9/2009 |
| JP | 2011-505355 A | 2/2011 |
| JP | 2011-511753 A | 4/2011 |
| JP | 2013-537525 A | 10/2013 |
| KR | 10-0389726 B1 | 6/2003 |
| KR | 10-2005-0026685 A | 3/2005 |
| KR | 10-2006-0106486 A | 10/2006 |
| KR | 10-2008-0039375 A | 5/2008 |
| KR | 10-2009-0096498 A | 9/2009 |
| KR | 10-2009-0098843 A | 9/2009 |
| KR | 10-0925017 B1 | 11/2009 |
| KR | 10-2010-0105494 A | 9/2010 |
| KR | 10-2011-0039230 A | 4/2011 |
| KR | 10-2012-0043208 A | 5/2012 |
| KR | 10-2012-0052973 A | 5/2012 |
| KR | 10-2012-0137271 A | 12/2012 |
| KR | 10-2012-0139579 A | 12/2012 |
| KR | 10-2014-0018462 A | 2/2014 |
| TW | 200848423 A | 12/2008 |
| TW | 201245246 | 11/2012 |
| TW | 201546053 | 12/2015 |
| WO | 96/32478 A1 | 10/1996 |
| WO | 97/34631 A1 | 9/1997 |
| WO | 2003/022304 A1 | 3/2003 |
| WO | 2005/035761 A1 | 4/2005 |
| WO | 2005/087797 A1 | 9/2005 |
| WO | 2006/059106 A2 | 6/2006 |
| WO | 2006/086769 | 8/2006 |
| WO | 2006/107124 A1 | 10/2006 |
| WO | 2006/134340 A2 | 12/2006 |
| WO | 2007/022123 A2 | 2/2007 |
| WO | 2007/100535 A2 | 9/2007 |
| WO | 2007/146038 A2 | 12/2007 |
| WO | 2008/071972 A1 | 6/2008 |
| WO | 2008/082274 A1 | 7/2008 |
| WO | 2008/101017 A2 | 8/2008 |
| WO | 2009/033756 A2 | 3/2009 |
| WO | 2009/058734 A1 | 5/2009 |
| WO | 2009/069983 A2 | 6/2009 |
| WO | 2009/099763 A1 | 8/2009 |
| WO | 2009/155257 A1 | 12/2009 |
| WO | 2009/155258 A2 | 12/2009 |
| WO | 2010/013012 A2 | 2/2010 |
| WO | 2010/033207 A1 | 3/2010 |
| WO | 2010/033220 A2 | 3/2010 |
| WO | 2010/070253 A1 | 6/2010 |
| WO | 2010/071807 A1 | 6/2010 |
| WO | 2010/096052 A1 | 8/2010 |
| WO | 2010/096142 A1 | 8/2010 |
| WO | 2010/107256 A2 | 9/2010 |
| WO | 2010/108153 A2 | 9/2010 |
| WO | 2010/148089 A1 | 12/2010 |
| WO | 2011/006497 A1 | 1/2011 |
| WO | 2011/056713 A2 | 5/2011 |
| WO | 2011/071957 A1 | 6/2011 |
| WO | 2011/075393 A2 | 6/2011 |
| WO | 2011/087671 A1 | 7/2011 |
| WO | 2011/087672 A1 | 7/2011 |
| WO | 2011/143208 A1 | 11/2011 |
| WO | 2012/011752 A2 | 1/2012 |
| WO | 2012/088379 A2 | 6/2012 |
| WO | 2012/169798 A2 | 12/2012 |
| WO | 2012/173422 A1 | 12/2012 |
| WO | 2013/157002 A1 | 10/2013 |
| WO | 2014/017843 A1 | 1/2014 |
| WO | 2014/073842 A1 | 5/2014 |
| WO | 2014/073845 A1 | 5/2014 |

OTHER PUBLICATIONS

What Causes Overweight and Obesity?, from http://www.nhlbi.nih.gov/health/health-topics/topics/obe/causes.html, pp. 1-5, accessed Oct. 6, 2014.

Vorobiev et al., "Chemical polysialylation: Design of conjugated human oxyntomodulin with a prolonged anorexic effect in vivo", Biochimie, 2013, vol. 95, 264-270.

Voet et al, Biochemistry, John Wiley & Sons Inc., 1995, pp. 235-241.

Vitamins & Supplements Search, http://www.webmd.com/vitamins-supplements/condition-1275-Hyperlipidemia.a- spx, accessed Dec. 29, 2015, pp. 1-3.

Treethammathurot et al., "Effect of PEG molecular weight and linking chemistry on the biological activity and thermal stability of PEGylated trypsin", International Journal of Pharmaceutics, 2008, vol. 357, pp. 252-259.

Skosyrev et al., "The Dependence of Stability of the Green Fluorescent Protein-Obelin Hybrids on the Nature of Their Constituent Modules and the Structure of the Amino Acid Linker", Russian Journal of Bioorganic Chemistry, 2001, vol. 27, No. 5, pp. 323-329.

Sigma-Aldrich, "Exendin-4 sequence", http://www.simgaaldrich.com/catalog/product/sigma/e7144lang=en (Registered) ion=US, accessed Dec. 28, 2015, 1 page.

Sigma, 2004, pp. 1-2.

Santoprete et al., "DPP-IV-resistant, long acting oxyntomodulin derivatives", Journal of Peptide Science, Feb. 2011, vol. 17, No. 4, 270-280.

Rudinger, Peptide Hormones, JA Parsons, Ed., 1976, pp. 1-7.

Prescription Medications for the Treatment of Obesity, pp. 1-8, published on Apr. 2013.

Pocai et al., "Glucagon-like peptide 1/glucagon receptor dual agonism reverses obesity in mice", Diabetes, 2009, vol. 58, No. 10, 2253-2266.

Obesity—Merck Manual, from http://www.merckmanuals.com/professional/nutritional_disorders/obesity_and_the_metab . . . , pp. 1-9, accessed Oct. 6, 2014.

Obesity Causes, from http://www.hsph.harvard.edu/obesity-prevention-source/obesity-causes/, pp. 1-3, accessed Oct. 6, 2014.

Ngo et al, Computational Complexity, Protein Structure Protection, and the Levinthal Paradox, 1994, pp. 491-494.

Machine translation of KR 20100105494 A, enclosed pp. 1-48, accessed May 2, 2014.

Lam, "Nonatheromatous Arteriosclerosis", http://222.merckmanuals.com/profession/cardiovasculardisorders/arterioscl- erosis/non . . . , accessed Dec. 29, 2015, 2 pages.

Lam, "Definition of Arteriosclerosis", http://www.merkmanuals.com/professional/cardiovascular-disorders/arterios-clerosis/defi . . . , accessed Dec. 29, 2015, 1 page.

Lam, "Atherosclerosis", Atherosclerosis—Cardiovascular Disorder—Merck Manuals Professional Edition, http://www.merkmanuals.com/professional/cardiovascular-disorder/arteriosc- lerosis/atherosclerosis, accessed Dec. 29, 2015, 1-14.

K Wynne et al: "Oxyntomodulin increases energy expenditure in addition to decreasing energy intake in overweight and obese humans: a randomized controlled trial", International Journal of Obesity, vol. 30, 20. 12, Apr. 18, 2006, pp. 1729-1736.

Hepatitis Health Center, "Fatty Liver Disease", http://www.webmd.com/hepatitis/fatty-liver-diseasepage=2&print=true, accessed, pp. 1-4, Dec. 29, 2015.

Goldberg, "Dyslipidemia", Dyslipidemia—Endocrine and Metabolic Disorders—Merck Manuals Professional Edition, http://www.merckmanuals.com/professional/endocrine-and-metabolic-diorders- /lipid-dis . . . , accessed Dec. 29, 2015, 11 pages.

(56) References Cited

OTHER PUBLICATIONS

Frankel et al., "Characterization of diphtheria fusion proteins targeted to the human interleukin-3 receptor", Protein Engineering, 2000, vol. 13, No. 8, pp. 575-581.
Drucker, Glucagon-Like Peptides, Diabetes, Feb. 1998, vol. 47, pp. 159-169.
Ding et al., "Exendin-4, a Glucagon-Like Protein-1 (GLP-1) Receptor Agonist, Reverses Hepatic Steatosis in ob/ob Mice", Hepatology, 2006, 43, 173-181.
Day et al., "Optimization of Co-Agonism at GLP-1 and Glucagon Receptors to Safely Maximize Weight Reduction in DIO-Rodents", Peptide Science, 2012, 98, 443-450.
Day et al, A new glucagon and GLP-1 co-agonist eliminates obesity in rodents, Nature Chemical Biology, 2009, 5, pp. 749-757.
Collie et al, Purification and sequence of rat oxyntomodulin, Proc. Natl. Acad. Sci. USA, 1994, 91, pp. 9362-9366.
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.
Berendsen, A Glimpae of the Holy Grail?, Science, 1998, 282, pp. 642-643.
Zhou et al., "Role of AMP-activated protein kinase in mechanism of metformin action", J. Clinical Invest., 2001, 108, 1167-1174.
Shani Ben-Shlomo et al., "Glucagon-like pepetide-1 reduces hepatic lipogenesis via activation of AMP-activated protein kinase", Journal of Hepatology, Sep. 27, 2010, vol. 54, No. 6, pp. 1214-1223.
Seok et al., "Exendin-4 Improves Nonalcoholic Fatty Liver Disease by Regulating Glucose Transporter 4 Expression in ob/ob Mice", Korean Journal of Physiology and Pharmacology, Jan. 1, 2014, p. 333.
Neuschwander-Tetri et al., "Improved Nonalcoholic Steatohepatitis After 48 Weeks of Treatment With the PPAR-y Ligand Rosiglitazone", Hepatology, 2003, 38, 1008-1017.
Dhanesha et al., "Treatment with exendin-4 improves the antidiabetic efficacy and reverses hepatic steatosis in glucokinase activator treated db/db mice", European Journal of Pharmacology, vol. 714, No. 1, Jun. 25, 2013, pp. 188-192.
Chao-lin Li et al., "Review on the effect of glucagon-like peptide-1 receptor agonists and dipeptidyl peptidase-4 inhibitors for the treatment of non-alcoholic fatty liver disease", Huashong University of Science and Technology Journal, vol. 35, No. 3, Jun. 1, 2015, pp. 333-336.
Shigeru, "Obesity and Metabolic Syndrome", Tokyo Internal Medical Association Seminar 2008 Special Lecture, Dec. 2008, vol. 24, No. 2, 8 pages.
Kerr et al., "(D-Ser2)Oxm[mPEG-PAL]: A novel modified analogue of oxyntomodulin with antihyperglycaemic, insullinotropic and anorexigenic actions", Biochemical Pharmacology, Dec. 2010, vol. 80, Issue 11, 1727-1735.

```
                         SEQUENCE LISTING

<160> NUMBER OF SEQ ID NOS: 59

<210> SEQ ID NO 1
<211> LENGTH: 37
<212> TYPE: PRT
<213> ORGANISM: Homo sapiens
<220> FEATURE:
<221> NAME/KEY: MISC_FEATURE
<222> LOCATION: (1)..(37)
<223> OTHER INFORMATION: Oxyntomodulin

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 2

His Ser Gln Gly Thr Phe Thr Ser Asp Tyr Ser Lys Tyr Leu Asp Glu
1               5                   10                  15

Glu Ala Val Arg Leu Phe Ile Glu Trp Leu Met Asn Thr Lys Arg Asn
            20                  25                  30

Arg Asn Asn Ile Ala
        35

<210> SEQ ID NO 3
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 3

His Ser Gln Gly Thr Phe Thr Ser Asp Tyr Ser Lys Tyr Leu Asp Glu
1               5                   10                  15

Arg Arg Ala Gln Asp Phe Val Ala Trp Leu Lys Asn Thr Gly Pro Ser
            20                  25                  30

Ser Gly Ala Pro Pro Pro Ser
        35

<210> SEQ ID NO 4
<211> LENGTH: 39
```

```
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 4

His Gly Gln Gly Thr Phe Thr Ser Asp Tyr Ser Arg Tyr Leu Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser
            35

<210> SEQ ID NO 5
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 5

His Gly Gln Gly Thr Phe Thr Ser Asp Tyr Ser Arg Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser
            35

<210> SEQ ID NO 6
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 6

His Gly Glu Gly Thr Phe Thr Ser Asp Leu Ser Arg Gln Met Glu Glu
1               5                   10                  15

Glu Ala Val Arg Leu Phe Ile Glu Trp Ala Ala His Ser Gln Gly Thr
                20                  25                  30

Phe Thr Ser Asp Tyr Ser Lys Tyr Leu Asp
            35                  40

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
```

```
<222> LOCATION: (1)..(1)
<223> OTHER INFORMATION: 4-imidazoacetyl

<400> SEQUENCE: 7

His Ser Gln Gly Thr Phe Thr Ser Asp Tyr Ser Arg Tyr Leu Asp Glu
1               5                   10                  15

Glu Ala Val Arg Leu Phe Ile Glu Trp Leu Met Asn Thr Lys
            20                  25                  30

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 8

His Ser Gln Gly Thr Phe Thr Ser Asp Leu Ser Arg Gln Leu Glu Glu
1               5                   10                  15

Glu Ala Val Arg Leu Phe Ile Glu Trp Leu Met Asn Lys
            20                  25

<210> SEQ ID NO 9
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (20)..(20)
<223> OTHER INFORMATION: Alpha-methyl-glutamic acid

<400> SEQUENCE: 9

His Gly Gln Gly Thr Phe Thr Ser Asp Tyr Ser Arg Tyr Leu Asp Glu
1               5                   10                  15

Glu Ala Val Glu Leu Phe Ile Glu Trp Leu Met Asn Thr Lys Arg Asn
            20                  25                  30

Arg Asn Asn Ile Ala
        35

<210> SEQ ID NO 10
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 10

His Ser Gln Gly Thr Phe Thr Ser Asp Tyr Ser Arg Gln Met Glu Glu
1               5                   10                  15

Glu Ala Val Arg Leu Phe Ile Glu Trp Leu Met Asn Gly Gly Pro Ser
```

```
Ser Gly Ala Pro Pro Ser Lys
        35                  40

<210> SEQ ID NO 11
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 11

His Gly Glu Gly Thr Phe Thr Ser Asp Leu Ser Arg Gln Met Glu Glu
1               5                   10                  15

Glu Ala Val Arg Leu Phe Ile Glu Trp Ala Ala His Ser Gln Gly Thr
            20                  25                  30

Phe Thr Ser Asp Tyr Ser Arg Tyr Leu Asp Lys
        35                  40

<210> SEQ ID NO 12
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 12

His Ser Gln Gly Thr Phe Thr Ser Asp Tyr Ser Arg Tyr Leu Asp Gly
1               5                   10                  15

Gly Gly His Gly Glu Gly Thr Phe Thr Ser Asp Leu Ser Lys Gln Met
            20                  25                  30

Glu Glu Glu Ala Val Lys
        35

<210> SEQ ID NO 13
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (16)..(16)
<223> OTHER INFORMATION: Alpha-methyl-glutamic acid
<220> FEATURE:
<221> NAME/KEY: MOD_RES
<222> LOCATION: (20)..(20)
<223> OTHER INFORMATION: Alpha-methyl-glutamic acid

<400> SEQUENCE: 13

His Ser Gln Gly Thr Phe Thr Ser Asp Tyr Ser Arg Tyr Leu Asp Glu
1               5                   10                  15
```

Glu Ala Val Glu Leu Phe Ile Glu Trp Leu Met Asn Thr Lys
            20                  25                  30

<210> SEQ ID NO 14
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (20)..(20)
<223> OTHER INFORMATION: Alpha-methyl-glutamic acid
<220> FEATURE:
<221> NAME/KEY: MOD_RES
<222> LOCATION: (24)..(24)
<223> OTHER INFORMATION: Alpha-methyl-glutamic acid

<400> SEQUENCE: 14

His Gly Gln Gly Thr Phe Thr Ser Asp Tyr Ser Arg Tyr Leu Asp Glu
1               5                   10                  15

Glu Ala Val Glu Leu Phe Ile Glu Trp Leu Met Asn Thr Lys Arg Asn
            20                  25                  30

Arg Asn Asn Ile Ala
        35

<210> SEQ ID NO 15
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (24)..(24)
<223> OTHER INFORMATION: Alpha-methyl-glutamic acid

<400> SEQUENCE: 15

His Gly Gln Gly Thr Phe Thr Ser Asp Tyr Ser Arg Tyr Leu Asp Glu
1               5                   10                  15

Glu Ala Val Arg Leu Phe Ile Glu Trp Leu Met Asn Thr Lys Arg Asn
            20                  25                  30

Arg Asn Asn Ile Ala
        35

<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 16

His Ser Gln Gly Thr Phe Thr Ser Asp Leu Ser Arg Gln Leu Glu Gly

```
                1               5                  10                 15
Gly Gly His Ser Gln Gly Thr Phe Thr Ser Asp Leu Ser Arg Gln Leu
            20                  25                 30

Glu Lys

<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 17

His Ser Gln Gly Thr Phe Thr Ser Asp Tyr Ser Arg Tyr Leu Asp Glu
1               5                   10                  15

Glu Ala Val Arg Leu Phe Ile Glu Trp Ile Arg Asn Thr Lys Arg Asn
            20                  25                  30

Arg Asn Asn Ile Ala
        35

<210> SEQ ID NO 18
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 18

His Ser Gln Gly Thr Phe Thr Ser Asp Tyr Ser Arg Tyr Leu Asp Glu
1               5                   10                  15

Glu Ala Val Arg Leu Phe Ile Glu Trp Ile Arg Asn Gly Gly Pro Ser
            20                  25                  30

Ser Gly Ala Pro Pro Pro Ser Lys
        35                  40

<210> SEQ ID NO 19
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MISC_FEATURE
<222> LOCATION: (16)..(20)
<223> OTHER INFORMATION: Ring formation between residues

<400> SEQUENCE: 19

His Ser Gln Gly Thr Phe Thr Ser Asp Tyr Ser Arg Tyr Leu Asp Glu
1               5                   10                  15

Glu Ala Val Lys Leu Phe Ile Glu Trp Ile Arg Asn Thr Lys Arg Asn
            20                  25                  30
```

Arg Asn Asn Ile Ala
        35

<210> SEQ ID NO 20
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MISC_FEATURE
<222> LOCATION: (16)..(20)
<223> OTHER INFORMATION: Ring formation between residues

<400> SEQUENCE: 20

His Ser Gln Gly Thr Phe Thr Ser Asp Tyr Ser Arg Tyr Leu Asp Glu
1               5                   10                  15

Glu Ala Val Lys Leu Phe Ile Glu Trp Ile Arg Asn Gly Gly Pro Ser
            20                  25                  30

Ser Gly Ala Pro Pro Pro Ser Lys
        35                  40

<210> SEQ ID NO 21
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 21

His Ser Gln Gly Thr Phe Thr Ser Asp Tyr Ser Arg Gln Leu Glu Glu
1               5                   10                  15

Glu Ala Val Arg Leu Phe Ile Glu Trp Val Arg Asn Thr Lys Arg Asn
            20                  25                  30

Arg Asn Asn Ile Ala
        35

<210> SEQ ID NO 22
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: Desamino-histidyl
<220> FEATURE:
<221> NAME/KEY: MISC_FEATURE
<222> LOCATION: (16)..(20)
<223> OTHER INFORMATION: Ring formation between residues

<400> SEQUENCE: 22

His Ser Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Lys

<210> SEQ ID NO 23
<211> LENGTH: 29
<212> TYPE: PRT
<213> ORGANISM: Artificial Sequence
<220> FEATURE:
<223> OTHER INFORMATION: Description of Artificial Sequence: Synthetic
    peptide construct of Oxyntomodulin derivative
<220> FEATURE:
<221> NAME/KEY: MOD_RES
<222> LOCATION: (2)..(2)
<223> OTHER INFORMATION: Aib

<400> SEQUENCE: 23

His Xaa Gln Gly Thr Phe Thr Ser Asp Tyr Ser Lys Tyr Leu Asp Glu
1               5                   10                  15

Lys Arg Ala Lys Glu Phe Val Cys Trp Leu Met Asn Thr
            20                  25

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence: Synthetic
    polypeptide construct of Oxyntomodulin derivative
<220> FEATURE:
<221> NAME/KEY: MOD_RES
<222> LOCATION: (2)..(2)
<223> OTHER INFORMATION: Aib

<400> SEQUENCE: 24

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
    polypeptide construct of Oxyntomodulin derivative
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 25

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Synthetic
    polypeptide construct of Oxyntomodulin derivative
<220> FEATURE:
<221> NAME/KEY: MOD_RES

```
<222> LOCATION: (2)..(2)
<223> OTHER INFORMATION: Aib
<220> FEATURE:
<221> NAME/KEY: MOD_RES
<222> LOCATION: (12)..(16)
<223> OTHER INFORMATION: Ring formation between residues

<400> SEQUENCE: 26

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 27
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide construct of Oxyntomodulin derivative
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 27

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 28
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide construct of Oxyntomodulin derivative
<220> FEATURE:
<221> NAME/KEY: MOD_RES
<222> LOCATION: (2)..(2)
<223> OTHER INFORMATION: Aib

<400> SEQUENCE: 28

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr
            20                  25

<210> SEQ ID NO 29
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide oxyntomodulin derivative
<220> FEATURE:
<221> NAME/KEY: MOD_RES
<222> LOCATION: (2)..(2)
<223> OTHER INFORMATION: D-Ser

<400> SEQUENCE: 29

His Ser Gln Gly Thr Phe Thr Ser Asp Tyr Ser Lys Tyr Leu Asp Ser
1               5                   10                  15
```

Arg Arg Ala Gln Asp Phe Val Gln Trp Leu Met Asn Thr Lys Arg Asn
            20                  25                  30

Arg Asn Asn Ile Ala
        35

<210> SEQ ID NO 30
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 30

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 31
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (2)..(2)
<223> OTHER INFORMATION: D-Ser

<400> SEQUENCE: 31

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 32
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

```
<400> SEQUENCE: 32

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 33
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide oxyntomodulin derivative
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 33

His Xaa Gln Gly Thr Phe Thr Ser Asp Tyr Ala Lys Tyr Leu Asp Glu
1               5                   10                  15

Lys Arg Ala Lys Glu Phe Val Gln Trp Leu Met Asn Thr Cys
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide oxyntomodulin derivative
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 34

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide construct; Variable R2 of Formula 1

<400> SEQUENCE: 35

Lys Arg Asn Arg Asn Asn Ile Ala
1               5

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide construct; Variable R2 of Formula 1

<400> SEQUENCE: 36

Gly Pro Ser Ser Gly Ala Pro Pro Pro Ser
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide construct; Variable R2 of Formula 1

<400> SEQUENCE: 37

Gly Pro Ser Ser Gly Ala Pro Pro Pro Ser Lys
1               5                   10

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide construct; Variable R2 of Formula 1

<400> SEQUENCE: 38

His Ser Gln Gly Thr Phe Thr Ser Asp Tyr Ser Lys Tyr Leu Asp
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct; Variable R2 of Formula 1

<400> SEQUENCE: 39

His Ser Gln Gly Thr Phe Thr Ser Asp Tyr Ser Arg Tyr Leu Asp Lys
1               5                   10                  15

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide construct; Variable R2 of Formula 1

<400> SEQUENCE: 40

His Gly Glu Gly Thr Phe Thr Ser Asp Leu Ser Lys Gln Met Glu Glu
1               5                   10                  15

Glu Ala Val Lys
            20

<210> SEQ ID NO 41
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct; Variable A or B of Formulae 2-3

<400> SEQUENCE: 41

Ser Gln Gly Thr Phe Thr Ser Asp Tyr Ser Lys Tyr Leu Asp Ser Arg
1               5                   10                  15

Arg Ala Gln Asp Phe Val Gln Trp Leu Met Asn Thr
            20                  25

<210> SEQ ID NO 42
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct; Variable A or B of Formulae 2-3

<400> SEQUENCE: 42

Ser Gln Gly Thr Phe Thr Ser Asp Tyr Ser Lys Tyr Leu Asp Glu Glu
1               5                   10                  15

Ala Val Arg Leu Phe Ile Glu Trp Leu Met Asn Thr
            20                  25

<210> SEQ ID NO 43
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct; Variable A or B of Formulae 2-3

<400> SEQUENCE: 43

Ser Gln Gly Thr Phe Thr Ser Asp Tyr Ser Lys Tyr Leu Asp Glu Arg
1               5                   10                  15

Arg Ala Gln Asp Phe Val Ala Trp Leu Lys Asn Thr
            20                  25

<210> SEQ ID NO 44
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct; Variable A or B of Formulae 2-3

<400> SEQUENCE: 44

Gly Gln Gly Thr Phe Thr Ser Asp Tyr Ser Arg Tyr Leu Glu Glu Glu
1               5                   10                  15

Ala Val Arg Leu Phe Ile Glu Trp Leu Lys Asn Gly
            20                  25

<210> SEQ ID NO 45
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct; Variable A or B of Formulae 2-3

<400> SEQUENCE: 45

Gly Gln Gly Thr Phe Thr Ser Asp Tyr Ser Arg Gln Met Glu Glu Glu
1               5                   10                  15

Ala Val Arg Leu Phe Ile Glu Trp Leu Lys Asn Gly
            20                  25

<210> SEQ ID NO 46
<211> LENGTH: 26
<212> TYPE: PRT
<213> ORGANISM: Artificial Sequence
<220> FEATURE:
<223> OTHER INFORMATION: Description of Artificial Sequence: Synthetic peptide construct; Variable A or B of Formulae 2-3

<400> SEQUENCE: 46

Gly Glu Gly Thr Phe Thr Ser Asp Leu Ser Arg Gln Met Glu Glu Glu
1               5                   10                  15

Ala Val Arg Leu Phe Ile Glu Trp Ala Ala
            20                  25

<210> SEQ ID NO 47
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct; Variable A or B of Formulae 2-3

<400> SEQUENCE: 47

Ser Gln Gly Thr Phe Thr Ser Asp Tyr Ser Arg Gln Met Glu Glu Glu
1               5                   10                  15

Ala Val Arg Leu Phe Ile Glu Trp Leu Met Asn Gly
            20                  25

<210> SEQ ID NO 48
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide construct; Variable B of Formula 3

<400> SEQUENCE: 48

Gly Glu Gly Thr Phe Thr Ser Asp Leu Ser Arg Gln Met Glu Glu Glu
1               5                   10                  15

Ala Val Arg Leu Phe Ile Glu Trp
            20

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide construct; Variable B of Formula 3

<400> SEQUENCE: 49

Ser Gln Gly Thr Phe Thr Ser Asp Tyr Ser Arg Tyr Leu Asp
1               5                   10

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cccggccccc gcggccgcta ttcgaaatac                                      30

<210> SEQ ID NO 51
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gaacggtccg gaggacgtcg actcttaaga tag                                      33

<210> SEQ ID NO 52
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cagcgacacc gaccgtcccc ccgtacttaa ggcc                                     34

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ctaaccgact ctcggggaag actgagctcg cc                                       32

<210> SEQ ID NO 54
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MOD_RES
<222> LOCATION: (2)..(2)
<223> OTHER INFORMATION: Aib(aminosiobutyric acid), d-alanine, glycine,
      Sar(N-methylglycine), serine or d-serine
<220> FEATURE:
<221> NAME/KEY: MOD_RES
<222> LOCATION: (3)..(3)
<223> OTHER INFORMATION: Glutamic acid or glutamine
<220> FEATURE:
<221> NAME/KEY: MOD_RES
<222> LOCATION: (10)..(10)
<223> OTHER INFORMATION: Leucine or tyrosine
<220> FEATURE:
<221> NAME/KEY: MOD_RES
<222> LOCATION: (11)..(11)
<223> OTHER INFORMATION: Serine or alanine
<220> FEATURE:
<221> NAME/KEY: MOD_RES
<222> LOCATION: (12)..(12)
<223> OTHER INFORMATION: Lysine or arginine
<220> FEATURE:
<221> NAME/KEY: MOD_RES
<222> LOCATION: (13)..(13)
<223> OTHER INFORMATION: Glutamine or tyrosine
<220> FEATURE:
<221> NAME/KEY: MOD_RES
<222> LOCATION: (14)..(14)
<223> OTHER INFORMATION: Leucine or methionine
<220> FEATURE:
<221> NAME/KEY: MOD_RES
<222> LOCATION: (15)..(15)
<223> OTHER INFORMATION: Aspartic acid or glutamic acid
<220> FEATURE:

```
<221> NAME/KEY: MOD_RES
<222> LOCATION: (16)..(16)
<223> OTHER INFORMATION: Glutamic acid, serine, alpha-methyl-glutamic
      acid or not present
<220> FEATURE:
<221> NAME/KEY: MOD_RES
<222> LOCATION: (17)..(17)
<223> OTHER INFORMATION: Glutamine, glutamic acid, lysine, arginine,
      serine or not present
<220> FEATURE:
<221> NAME/KEY: MOD_RES
<222> LOCATION: (18)..(18)
<223> OTHER INFORMATION: Alanine, arginine, valine or not present
<220> FEATURE:
<221> NAME/KEY: MOD_RES
<222> LOCATION: (19)..(19)
<223> OTHER INFORMATION: Alanine, arginine, serine, valine or not
      present
<220> FEATURE:
<221> NAME/KEY: MOD_RES
<222> LOCATION: (20)..(20)
<223> OTHER INFORMATION: Lysine, glutamine, arginine, alpha-methyl-
      glutamic acid or not present
<220> FEATURE:
<221> NAME/KEY: MOD_RES
<222> LOCATION: (21)..(21)
<223> OTHER INFORMATION: Aspartic acid, glutamic acid, leucine or not
      present
<220> FEATURE:
<221> NAME/KEY: MISC_FEATURE
<222> LOCATION: (22)..(22)
<223> OTHER INFORMATION: May or may not be present
<220> FEATURE:
<221> NAME/KEY: MOD_RES
<222> LOCATION: (23)..(23)
<223> OTHER INFORMATION: Isoleucine, valine or not present
<220> FEATURE:
<221> NAME/KEY: MOD_RES
<222> LOCATION: (24)..(24)
<223> OTHER INFORMATION: Alanine, cysteine, glutamic acid, lysine,
      glutamine, alpha-methyl-glutamic acid or not present
<220> FEATURE:
<221> NAME/KEY: MISC_FEATURE
<222> LOCATION: (25)..(25)
<223> OTHER INFORMATION: May or may not be present
<220> FEATURE:
<221> NAME/KEY: MOD_RES
<222> LOCATION: (26)..(26)
<223> OTHER INFORMATION: Alanine, isoleucine, leucine, serine, valine
      or not present
<220> FEATURE:
<221> NAME/KEY: MOD_RES
<222> LOCATION: (27)..(27)
<223> OTHER INFORMATION: Alanine, lysine, methionine, glutamine,
      arginine or not present
<220> FEATURE:
<221> NAME/KEY: MISC_FEATURE
<222> LOCATION: (28)..(28)
<223> OTHER INFORMATION: May or may not be present
<220> FEATURE:
<221> NAME/KEY: MOD_RES
<222> LOCATION: (29)..(29)
<223> OTHER INFORMATION: Alanine, glycine, threonine or not present
<220> FEATURE:
<221> NAME/KEY: MOD_RES
<222> LOCATION: (30)..(30)
<223> OTHER INFORMATION: Cysteine, lysine or not present
<220> FEATURE:
<221> NAME/KEY: MOD_RES
<222> LOCATION: (31)..(40)
<223> OTHER INFORMATION: Alanine, glycine, serine or not present
<220> FEATURE:
<221> NAME/KEY: MISC_FEATURE
<222> LOCATION: (31)..(40)
<223> OTHER INFORMATION: This region may encompass 2 to 10 amino acids,
      wherein some positions may be absent
<220> FEATURE:
<221> NAME/KEY: MISC_FEATURE
<222> LOCATION: (41)..(60)
```

```
<223> OTHER INFORMATION: This region may encompass 8 to 20 amino acids
      including "KRNRNNIA" or "GPSSGAPPPS" or "GPSSGAPPPSK" or
      "HSQGTFTSDYSKYLD" or "HSQGTFTSDYSRYLDK" or "HGEGTFTSDLSKQMEEEAVK,"
      wherein some or all positions may be absent
<220> FEATURE:
<223> OTHER INFORMATION: See specification as filed for detailed
      description of substitutions and preferred embodiments

<400> SEQUENCE: 54

Xaa Xaa Xaa Gly Thr Phe Thr Ser Asp Xaa Xaa Xaa Xaa Xaa Xaa
1               5                   10                  15

Xaa Xaa Xaa Xaa Xaa Phe Xaa Xaa Trp Xaa Xaa Asn Xaa Xaa Xaa Xaa
                20                  25                  30

Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa
        50                  55                  60

<210> SEQ ID NO 55
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MISC_FEATURE
<222> LOCATION: (2)..(29)
<223> OTHER INFORMATION: This region may encompass 26 to 28 amino acids
      including "SQGTFTSDYSKYLDSRRAQDFVQWLMNT" or
      "SQGTFTSDYSKYLDEEAVRLFIEWLMNT" or "SQGTFTSDYSKYLDERRAQDFVAWLKNT"
      or "GQGTFTSDYSRYLEEEAVRLFIEWLKNG" or
      "GQGTFTSDYSRQMEEEAVRLFIEWLKNG"
<220> FEATURE:
<221> NAME/KEY: MISC_FEATURE
<222> LOCATION: (2)..(29)
<223> OTHER INFORMATION: Continued from above; or
      "GEGTFTSDLSRQMEEEAVRLFIEWAA" or "SQGTFTSDYSRQMEEEAVRLFIEWLMNG,"
      wherein some positions may be absent
<220> FEATURE:
<221> NAME/KEY: MISC_FEATURE
<222> LOCATION: (30)..(40)
<223> OTHER INFORMATION: This region may encompass 8 to 11 amino acids
      including "KRNRNNIA" or "GPSSGAPPPS" or "GPSSGAPPPSK," wherein
      some positions may be absent
<220> FEATURE:
<223> OTHER INFORMATION: See specification as filed for detailed
      description of substitutions and preferred embodiments

<400> SEQUENCE: 55

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa
            35                  40

<210> SEQ ID NO 56
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MISC_FEATURE
<222> LOCATION: (2)..(29)
<223> OTHER INFORMATION: This region may encompass 14 to 28 amino acids
      including "SQGTFTSDYSKYLDSRRAQDFVQWLMNT" or
      "SQGTFTSDYSKYLDEEAVRLFIEWLMNT" or "SQGTFTSDYSKYLDERRAQDFVAWLKNT"
      or "GQGTFTSDYSRYLEEEAVRLFIEWLKNG" or
      "GQGTFTSDYSRQMEEEAVRLFIEWLKNG"
<220> FEATURE:
<221> NAME/KEY: MISC_FEATURE
<222> LOCATION: (2)..(29)
<223> OTHER INFORMATION: Continued from above; or
      "GEGTFTSDLSRQMEEEAVRLFIEWAA" or "SQGTFTSDYSRQMEEEAVRLFIEWLMNG" or
      "GEGTFTSDLSRQMEEEAVRLFIEW" or "SQGTFTSDYSRYLD," wherein some
      positions may be absent
<220> FEATURE:
<221> NAME/KEY: MOD_RES
<222> LOCATION: (30)..(39)
<223> OTHER INFORMATION: Alanine, glycine, serine or not present
<220> FEATURE:
<221> NAME/KEY: MISC_FEATURE
<222> LOCATION: (30)..(39)
<223> OTHER INFORMATION: This region may encompass 2 to 10 amino acids,
      wherein some positions may be absent
<220> FEATURE:
<221> NAME/KEY: MISC_FEATURE
<222> LOCATION: (40)..(59)
<223> OTHER INFORMATION: This region may encompass 15 to 20 amino acids
      including "HSQGTFTSDYSKYLD" or "HSQGTFTSDYSRYLDK" or
      "HGEGTFTSDLSKQMEEEAVK," wherein some positions may be absent
<220> FEATURE:
<223> OTHER INFORMATION: See specification as filed for detailed
      description of substitutions and preferred embodiments

<400> SEQUENCE: 56

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa
    50                  55

<210> SEQ ID NO 57
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MOD_RES
<222> LOCATION: (16)..(16)
<223> OTHER INFORMATION: Serine, glutamic acid or arginine
<220> FEATURE:
<221> NAME/KEY: MOD_RES
<222> LOCATION: (17)..(17)
<223> OTHER INFORMATION: Arginine, glutamic acid or serine
<220> FEATURE:
<221> NAME/KEY: MOD_RES
<222> LOCATION: (18)..(18)
```

<223> OTHER INFORMATION: Arginine, alanine or valine
<220> FEATURE:
<221> NAME/KEY: MOD_RES
<222> LOCATION: (19)..(19)
<223> OTHER INFORMATION: Arginine, valine or serine
<220> FEATURE:
<221> NAME/KEY: MOD_RES
<222> LOCATION: (20)..(20)
<223> OTHER INFORMATION: Glutamine, arginine or lysine
<220> FEATURE:
<221> NAME/KEY: MOD_RES
<222> LOCATION: (26)..(26)
<223> OTHER INFORMATION: Isoleucine, valine or serine
<220> FEATURE:
<221> NAME/KEY: MOD_RES
<222> LOCATION: (27)..(27)
<223> OTHER INFORMATION: Methionine, arginine or glutamine
<220> FEATURE:
<221> NAME/KEY: MOD_RES
<222> LOCATION: (29)..(29)
<223> OTHER INFORMATION: Threonine, glycine or alanine
<220> FEATURE:
<221> NAME/KEY: MISC_FEATURE
<222> LOCATION: (30)..(40)
<223> OTHER INFORMATION: This region may encompass 8 to 11 amino acids
      including "KRNRNNIA" or "GPSSGAPPPS" or "GPSSGAPPPSK," wherein
      some positions may be absent
<220> FEATURE:
<223> OTHER INFORMATION: See specification as filed for detailed
      description of substitutions and preferred embodiments

<400> SEQUENCE: 57

Xaa Ser Gln Gly Thr Phe Thr Ser Asp Tyr Ser Lys Tyr Leu Asp Xaa
1               5                   10                  15

Xaa Xaa Xaa Xaa Leu Phe Val Gln Trp Xaa Xaa Asn Xaa Xaa Xaa Xaa
            20                  25                  30

Xaa Xaa Xaa Xaa Xaa Xaa Xaa Xaa
        35                  40

<210> SEQ ID NO 58
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MOD_RES
<222> LOCATION: (2)..(2)
<223> OTHER INFORMATION: Serine, Aib, Sar, d-alanine or d-serine
<220> FEATURE:
<221> NAME/KEY: MOD_RES
<222> LOCATION: (16)..(16)
<223> OTHER INFORMATION: Serine or glutamic acid
<220> FEATURE:
<221> NAME/KEY: MOD_RES
<222> LOCATION: (17)..(17)
<223> OTHER INFORMATION: Arginine or lysine
<220> FEATURE:
<221> NAME/KEY: MOD_RES
<222> LOCATION: (20)..(20)
<223> OTHER INFORMATION: Glutamine or lysine
<220> FEATURE:
<221> NAME/KEY: MOD_RES
<222> LOCATION: (21)..(21)
<223> OTHER INFORMATION: Aspartic acid or glutamic acid
<220> FEATURE:
<221> NAME/KEY: MOD_RES
<222> LOCATION: (24)..(24)

<223> OTHER INFORMATION: Glutamine, cysteine or lysine
<220> FEATURE:
<221> NAME/KEY: MOD_RES
<222> LOCATION: (30)..(30)
<223> OTHER INFORMATION: Cysteine, lysine or not present
<220> FEATURE:
<221> NAME/KEY: MISC_FEATURE
<222> LOCATION: (31)..(41)
<223> OTHER INFORMATION: This region may encompass 8 to 11 amino acids
      including "KRNRNNIA" or "GPSSGAPPPS" or "GPSSGAPPPSK," wherein
      some or all positions may be absent
<220> FEATURE:
<223> OTHER INFORMATION: See specification as filed for detailed
      description of substitutions and preferred embodiments

<400> SEQUENCE: 58

Xaa Xaa Gln Gly Thr Phe Thr Ser Asp Tyr Ser Lys Tyr Leu Asp Xaa
 1               5                  10                  15

Xaa Arg Ala Xaa Xaa Phe Val Xaa Trp Leu Met Asn Thr Xaa Xaa Xaa
             20                  25                  30

Xaa Xaa Xaa Xaa Xaa Xaa Xaa Xaa Xaa
         35                  40

<210> SEQ ID NO 59
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, 4-imidazoacetyl
      or tyrosine
<220> FEATURE:
<221> NAME/KEY: MOD_RES
<222> LOCATION: (2)..(2)
<223> OTHER INFORMATION: Aib(aminosiobutyric acid), glycine or serine
<220> FEATURE:
<221> NAME/KEY: MOD_RES
<222> LOCATION: (3)..(3)
<223> OTHER INFORMATION: Glutamic acid or glutamine
<220> FEATURE:
<221> NAME/KEY: MOD_RES
<222> LOCATION: (10)..(10)
<223> OTHER INFORMATION: Leucine or tyrosine
<220> FEATURE:
<221> NAME/KEY: MOD_RES
<222> LOCATION: (11)..(11)
<223> OTHER INFORMATION: Serine or alanine
<220> FEATURE:
<221> NAME/KEY: MOD_RES
<222> LOCATION: (12)..(12)
<223> OTHER INFORMATION: Lysine or arginine
<220> FEATURE:
<221> NAME/KEY: MOD_RES
<222> LOCATION: (13)..(13)
<223> OTHER INFORMATION: Glutamine or tyrosine
<220> FEATURE:
<221> NAME/KEY: MOD_RES
<222> LOCATION: (14)..(14)
<223> OTHER INFORMATION: Leucine or methionine
<220> FEATURE:
<221> NAME/KEY: MOD_RES
<222> LOCATION: (15)..(15)
<223> OTHER INFORMATION: Aspartic acid or glutamic acid
<220> FEATURE:
<221> NAME/KEY: MOD_RES
<222> LOCATION: (16)..(16)
<223> OTHER INFORMATION: Glutamic acid, alpha-methyl-glutamic acid or
      not present
<220> FEATURE:
<221> NAME/KEY: MOD_RES
<222> LOCATION: (17)..(17)

-continued

```
<223> OTHER INFORMATION: Glutamine, glutamic acid, lysine, arginine or
      not present
<220> FEATURE:
<221> NAME/KEY: MOD_RES
<222> LOCATION: (18)..(18)
<223> OTHER INFORMATION: Alanine, arginine or not present
<220> FEATURE:
<221> NAME/KEY: MOD_RES
<222> LOCATION: (19)..(19)
<223> OTHER INFORMATION: Alanine, valine or not present
<220> FEATURE:
<221> NAME/KEY: MOD_RES
<222> LOCATION: (20)..(20)
<223> OTHER INFORMATION: Lysine, glutamine, arginine, alpha-methyl-
      glutamic acid or not present
<220> FEATURE:
<221> NAME/KEY: MOD_RES
<222> LOCATION: (21)..(21)
<223> OTHER INFORMATION: Aspartic acid, glutamic acid, leucine or not
      present
<220> FEATURE:
<221> NAME/KEY: MISC_FEATURE
<222> LOCATION: (22)..(22)
<223> OTHER INFORMATION: May or may not be present
<220> FEATURE:
<221> NAME/KEY: MOD_RES
<222> LOCATION: (23)..(23)
<223> OTHER INFORMATION: Isoleucine, valine or not present
<220> FEATURE:
<221> NAME/KEY: MOD_RES
<222> LOCATION: (24)..(24)
<223> OTHER INFORMATION: Alanine, cysteine, glutamic acid, glutamine,
      alpha-methyl-glutamic acid or not present
<220> FEATURE:
<221> NAME/KEY: MISC_FEATURE
<222> LOCATION: (25)..(25)
<223> OTHER INFORMATION: May or may not be present
<220> FEATURE:
<221> NAME/KEY: MOD_RES
<222> LOCATION: (26)..(26)
<223> OTHER INFORMATION: Alanine, isoleucine, leucine, valine or not
      present
<220> FEATURE:
<221> NAME/KEY: MOD_RES
<222> LOCATION: (27)..(27)
<223> OTHER INFORMATION: Alanine, lysine, methionine, arginine or not
      present
<220> FEATURE:
<221> NAME/KEY: MISC_FEATURE
<222> LOCATION: (28)..(29)
<223> OTHER INFORMATION: May or may not be present
<220> FEATURE:
<221> NAME/KEY: MOD_RES
<222> LOCATION: (30)..(30)
<223> OTHER INFORMATION: Cysteine, lysine or not present
<220> FEATURE:
<221> NAME/KEY: MISC_FEATURE
<222> LOCATION: (31)..(40)
<223> OTHER INFORMATION: This region may encompass 2 to 10 residues,
      wherein some positions may not be present
<220> FEATURE:
<221> NAME/KEY: MISC_FEATURE
<222> LOCATION: (41)..(60)
<223> OTHER INFORMATION: This region may encompass 8 to 20 amino acids
      including "KRNRNNIA" or "GPSSGAPPPS" or "GPSSGAPPPSK" or
      "HSQGTFTSDYSKYLD" or "HSQGTFTSDYSRYLDK" or "HGEGTFTSDLSKQMEEEAVK,"
      wherein some or all positions may be absent
<220> FEATURE:
<223> OTHER INFORMATION: See specification as filed for detailed
      description of substitutions and preferred embodiments

<400> SEQUENCE: 59

Xaa Xaa Xaa Gly Thr Phe Thr Ser Asp Xaa Xaa Xaa Xaa Xaa Xaa Xaa
1               5                   10                  15

Xaa Xaa Xaa Xaa Xaa Phe Xaa Xaa Trp Xaa Xaa Asn Thr Xaa Gly Gly
            20                  25                  30
```

-continued

```
Gly Gly Gly Gly Gly Gly Gly Gly Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa
    50                  55                  60
```

CONJUGATE COMPRISING OXYNTOMODULIN AND AN IMMUNOGLOBULIN FRAGMENT, AND USE THEREOF

CROSS REFERENCE TO RELATED APPLICATIONS

This application is a divisional of U.S. application Ser. No. 14/126,914 filed Feb. 6, 2014, which issued as U.S. Pat. No. 9,731,031, which is a National Stage of International Application No. PCT/KR2012/004722 filed Jun. 15, 2012, claiming priority to Korean Patent Application No. 10-2011-0058852 filed Jun. 17, 2011, the contents of each of which are incorporated herein by reference in their entirety.

SEQUENCE LISTING

The instant application contains a Sequence Listing which has been submitted electronically in ASCII format and is hereby incorporated by reference in its entirety. The ASCII copy, created on Jun. 3, 2016, is named 106132.000242_SL.txt and is 40,672 bytes in size.

TECHNICAL FIELD

The present invention relates to a conjugate comprising oxyntomodulin and an immunoglobulin fragment, and the use thereof. More particularly, the present invention relates to a conjugate comprising oxyntomodulin, an immunoglobulin Fc region, and non-peptidyl polymer wherein the conjugate being obtainable by covalently linking oxyntomodulin to immunoglobulin Fc region via non-peptidyl polymer, and a pharmaceutical composition for the prevention or treatment of obesity comprising the conjugate.

BACKGROUND ART

Recently, economic growth and changes in lifestyle are leading to changes in eating habits. The main causes of rising overweight and obesity rates in contemporary people are consumption of high-calorie foods such as fast foods and lack of exercise. World Health Organization (WHO) estimates that more than 1 billion people worldwide are overweight and at least 300 million of them are clinically obese. In particular, 250,000 people die each year in Europe and more than 2.5 million people worldwide die each year as a result of being overweight (World Health Organization, Global Strategy on Diet, Physical Activity and Health, 2004).

Being overweight and obese increases blood pressure and cholesterol levels to cause occurrence or exacerbation of various diseases such as cardiovascular disease, diabetes, and arthritis, and are also main causes of rising incidence rates of arteriosclerosis, hypertension, hyperlipidemia or cardiovascular disease in children or adolescents as well as in adults.

Obesity is a severe condition that causes various diseases worldwide. It is thought to be overcome by individual efforts, and it is also believed that obese patients lack self-control. However, it is difficult to treat obesity, because obesity is a complex disorder involving appetite regulation and energy metabolism. For the treatment of obesity, abnormal actions associated with appetite regulation and energy metabolism should be treated together with efforts of obese patients. Many attempts have been made to develop drugs capable of treating the abnormal actions. As the result of these efforts, drugs such as Rimonabant (Sanofi-Aventis), Sibutramin (Abbott), CONTRAVE® (Takeda), and Orlistat (Roche) have been developed, but they have the disadvantages of serious adverse effects or very weak anti-obesity effects. For example, it was reported that Rimonabant (Sanofi-Aventis) shows a side-effect of central nerve disorder, Sibutramine (Abbott) and CONTRAVE® (Takeda) show cardiovascular side-effects, and Orlistat (Roche) shows only 4 kg of weight loss when taken for 1 year. Unfortunately, there are no therapeutic agents for obesity which can be safely prescribed for obese patients.

Many studies have been made to develop therapeutic agents for obesity which do not have the problems of the conventional anti-obesity drugs. Recently, glucagon derivatives have received much attention. Glucagon is produced by the pancreas when the level of glucose in the blood drops resulting from other medications or diseases, hormone or enzyme deficiencies. Glucagon stimulates glycogen breakdown in the liver, and facilitates glucose release to raise blood glucose levels to a normal range. In addition to the effect of increasing the blood glucose level, glucagon suppresses appetite and activates hormone-sensitive lipase (HSL) of adipocytes to facilitate lipolysis, thereby showing anti-obesity effects. One of the glucagon derivatives, glucagon like peptide-1 (GLP-1) is under development as a therapeutic agent for hyperglycemia in patients with diabetes, and it functions to stimulate insulin synthesis and secretion, to inhibit glucagon secretion, to slow gastric emptying, to increase glucose utilization, and to inhibit food intake. Exendin-4 is isolated from lizard venom that shares approximately 50% amino acid homology with GLP-1 and is also reported to activate the GLP-1 receptor, thereby ameliorating hyperglycemia in patients with diabetes. However, anti-obesity drugs including GLP-1 are reported to show side-effects such as vomiting and nausea.

As an alternative to GLP-1, therefore, much attention has been focused on oxyntomodulin, a peptide derived from a glucagon precursor, pre-glucagon that binds to the receptors of two peptides, GLP-1 and glucagon. Oxyntomodulin represents a potent anti-obesity therapy, because it inhibits food intake like GLP-1, promotes satiety, and has a lipolytic activity like glucagon.

Based on the dual function of the oxyntomodulin peptide, it has been actively studied as a drug for the treatment of obesity. For example, Korean Patent No. 925017 discloses a pharmaceutical composition including oxyntomodulin as an active ingredient for the treatment of overweight human, which is administered via an oral, parenteral, mucosal, rectal, subcutaneous, or transdermal route. However, it has been reported that this anti-obesity drug including oxyntomodulin has a short in vivo half-life and weak therapeutic efficacy, even though administered at a high dose three times a day. Thus, many efforts have been made to improve the in vivo half-life or therapeutic effect of oxyntomodulin on obesity by its modification.

For example, a dual agonist oxyntomodulin (Merck) is prepared by substituting L-serine with D-serine at position 2 of oxyntomodulin to increase a resistance to dipeptidyl peptidase-IV (DPP-IV) and by attaching a cholesterol moiety at the C-terminal to increase the blood half-life at the same time. ZP2929 (Zealand) is prepared by substituting L-serine with D-serine at position 2 to enhance resistance to DPP-IV, substituting arginine with alanine at position 17 to enhance resistance to protease, substituting methionine with lysine at position 27 to enhance oxidative stability, and substituting glutamine with aspartic acid and alanine at positions 20 and 24 and asparagine with serine at position 28 to enhance deamidation stability. However, even though the half-life of the dual agonist oxyntomodulin (Merck) was enhanced to show half-life 8-12 minutes longer than the native oxyntomodulin, it still has a very short in vivo half-life of 1.7 hr and its administration dose is also as high as several mg/kg. Unfortunately, oxyntomodulin or derivatives thereof have disadvantages of daily administration of high dose due to the short half-life and low efficacy.

DISCLOSURE

Technical Problem

Accordingly, the present inventors have made many efforts to develop a method for increasing the blood half-life of oxyntomodulin while maintaining its activity in vivo. As a result, they found that a conjugate prepared by linking a carrier to oxyntomodulin using a non-peptidyl polymer show improved blood half-life while maintaining the activity in vivo so as to exhibit excellent anti-obesity effects, thereby completing the present invention.

Technical Solution

An object of the present invention is to provide a conjugate comprising oxyntomodulin, an immunoglobulin Fc region, and non-peptidyl polymer wherein the conjugate being obtainable by covalently linking oxyntomodulin to immunoglobulin Fc region via non-peptidyl polymer.

Another object of the present invention is to provide a pharmaceutical composition for the prevention or treatment of obesity, comprising the conjugates.

Still another object of the present invention is to provide a method for preventing or treating obesity, comprising the step of administering the conjugate or the composition to a subject.

Still another object of the present invention is to provide use of the conjugate or the composition in the preparation of drugs for the prevention or treatment of obesity.

Advantageous Effects

The conjugate comprising oxyntomodulin and the immunoglobulin Fc of the present invention reduces food intake, suppresses gastric emptying, and facilitates lipolysis without side-effects, unlike native oxyntomodulin, and also shows excellent receptor-activating effects and long-term sustainability, compared to oxyntomodulin. Thus, it can be widely used in the treatment of obesity with safety and efficacy. Unlike native oxyntomodulin, the novel peptide of the present invention reduces food intake, suppresses gastric emptying, and facilitates lipolysis without side-effects, and also shows excellent receptor-activating effects. Thus, it can be widely used in the treatment of obesity with safety and efficacy.

BEST MODE

Figure 1:
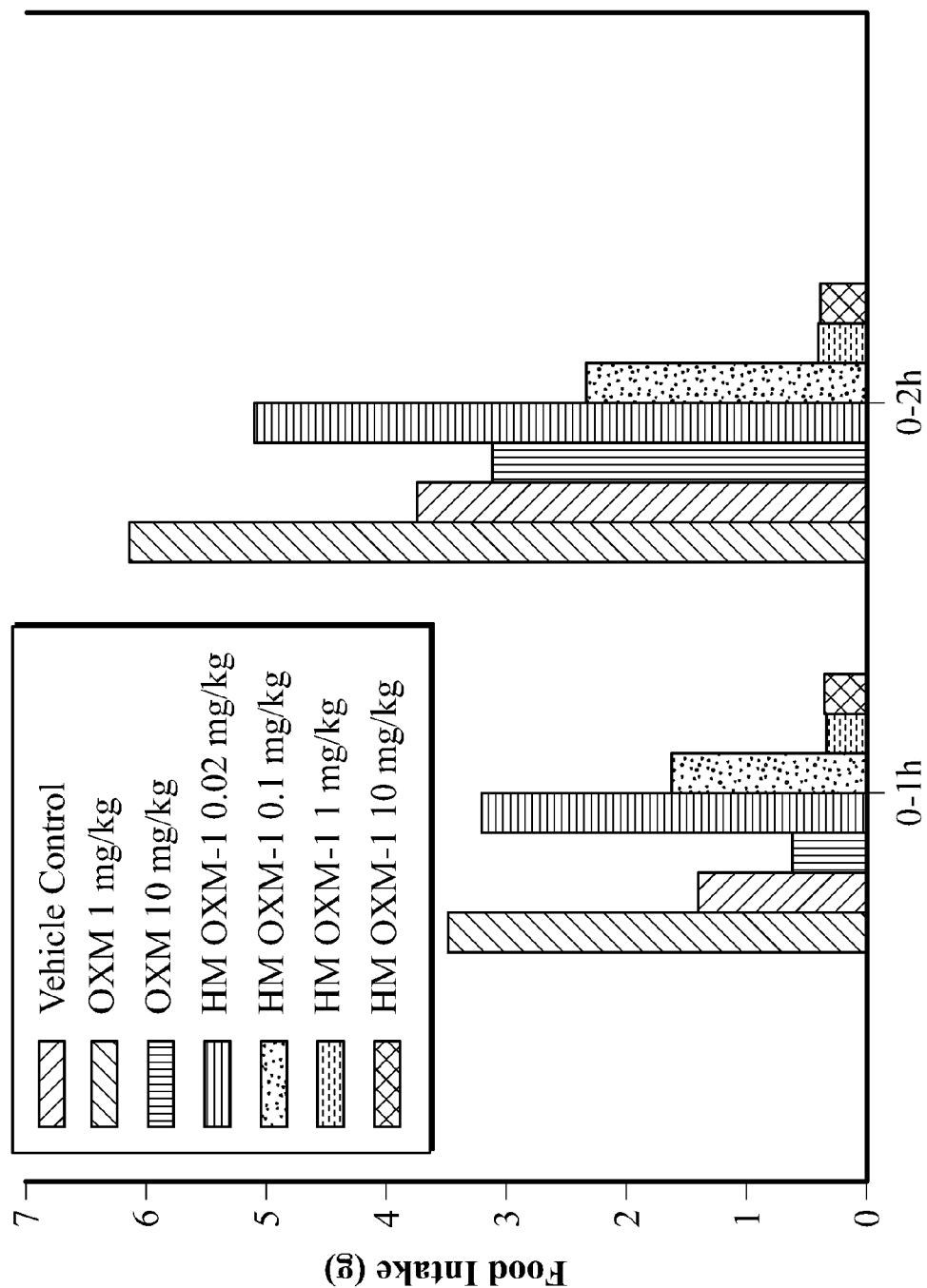
FIG. 1 is a graph showing changes in food intake according to administration dose of oxyntomodulin or oxyntomodulin derivative.

In one aspect to achieve the above objects, the present invention provides a conjugate comprising oxyntomodulin, an immunoglobulin Fc region, and non-peptidyl polymer wherein the conjugate being obtainable by covalently linking oxyntomodulin to immunoglobulin Fc region via non-peptidyl polymer.

As used herein, the term "conjugate" means a conjugate comprising oxyntomodulin and other factors. Other factors can be any substance which can induce increased stability in blood, suspend emission through the kidney, or other useful effects. In the present invention, the factors can be immunoglobulin Fc region. Preferably, the conjugate can be comprised of an oxyntomodulin, and an immunoglobulin Fc region, which are linked by a non-peptidyl polymer. The non-peptidyl polymer can link an oxyntomodulin and an immunoglobulin Fc region via covalent bonds. Two terminal ends of non-peptidyl polymer can be linked to an amine group or thiol group of the immunoglobulin Fc region and oxyntomodulin derivatives, respectively.

The conjugate of the present invention means to have an improved in-vivo duration of efficacy, compared to native oxyntomodulin, and the long-acting conjugate may include oxyntomodulin prepared by modification, substitution, addition, or deletion of the amino acid sequences of the native oxyntomodulin, oxyntomodulin conjugated to a biodegradable polymer such as polyethylene glycol (PEG), oxyntomodulin conjugated to a long-acting protein such as albumin or immunoglobulin, oxyntomodulin conjugated to fatty acid having the ability of binding to albumin in the body, or oxyntomodulin encapsulated in biodegradable nanoparticles, but the type of the long-acting conjugate is not limited thereto.

As used herein, the term "oxyntomodulin" means a peptide derived from a glucagon precursor, pre-glucagon, and includes a native oxyntomodulin, precursors, derivatives, fragments thereof, and variants thereof. Preferably, it can have the amino acid sequence of SEQ ID NO. 1 (HSQGTFTSDYSKYLDSRRAQDFVQWLMNTKRNRNNIA).

The term, "oxyntomodulin variant" is a peptide having one or more amino acid sequences different from those of native oxyntomodulin, and means a peptide that retains the function of activating the GLP-1 and glucagon receptors, and it may be prepared by any one of substitution, addition, deletion, and modification or by a combination thereof in a part of the amino acid sequences of the native oxyntomodulin.

The term, "oxyntomodulin derivative" includes peptides, peptide derivatives or peptide mimetics that are prepared by addition, deletion or substitution of amino acids of oxyntomodulin so as to activate both of the GLP-1 receptor and the glucagon receptor at a high level, compared to the native oxyntomodulin.

The term, "oxyntomodulin fragment" means a fragment having one or more amino acids added or deleted at the N-terminus or the C-terminus of the native oxyntomodulin, in which non-naturally occurring amino acids (for example, D-type amino acid) can be added, and has a function of activating both of the GLP-1 receptor and the glucagon receptor.

Each of the preparation methods for the variants, derivatives, and fragments of oxyntomodulin can be used individually or in combination. For example, the present invention includes a peptide that has one or more amino acids different from those of native peptide and deamination of the N-terminal amino acid residue, and has a function of activating both of the GLP-1 receptor and the glucagon receptor.

Amino acids mentioned herein are abbreviated according to the nomenclature rule of IUPAC-IUB as follows:

| Alanine | A | Arginine | R |
| Asparagine | N | Aspartic acid | D |
| Cysteine | C | Glutamic acid | E |
| Glutamine | Q | Glycine | G |
| Histidine | H | Isoleucine | I |
| Leucine | L | Lysine | K |
| Methionine | M | Phenylalanine | F |
| Proline | P | Serine | S |
| Threonine | T | Tryptophan | W |
| Tyrosine | Y | Valine | V |

In the present invention, the oxyntomodulin derivative encompasses any peptide that is prepared by substitutions, additions, deletions or post translational modifications (e.g., methylation, acylation, ubiquitination, intramolecular covalent bonding) in the amino acid sequence of oxyntomodulin (HSQGTFTSDYSKYLDSRRAQDFVQWLMNTKRNRNNIA, SEQ ID NO. 1) so as to activate the glucagon and GLP-1 receptors at the same time. Upon substitution or addition of amino acids, any of the 20 amino acids commonly found in human proteins, as well as atypical or non-naturally occurring amino acids can be used. Commercially available sources of atypical amino acids include SIGMA-ALDRICH®, CHEMPEP® Inc., and GENZYME® Pharmaceuticals. The peptides including these amino acids and atypical peptide sequences may be synthesized and purchased from commercial suppliers, for example, AMERICAN PEPTIDE COMPANY® or BACHEM® (USA) or Anygen (Korea).

In one specific embodiment, the oxyntomodulin derivative of the present invention is a novel peptide including the amino acids of the following Formula 1.

R1-X1-X2-GTFTSD-X3-X4-X5-X6-X7-X8-X9-X10-
X11-X12-X13-X14-X15-X16-X17-X18-X19-
X20-X21-X22-X23-X24-R2 (Formula 1) (SEQ ID NO: 54)

wherein R1 is histidine, desamino-histidyl, dimethyl-histidyl (N-dimethyl-histidyl), beta-hydroxyimidazopropionyl, 4-imidazoacetyl, beta-carboxy imidazopropionyl or tyrosine;

X1 is Aib (aminosiobutyric acid), d-alanine, glycine, Sar (N-methylglycine), serine, or d-serine;

X2 is glutamic acid or glutamine;

X3 is leucine or tyrosine;

X4 is serine or alanine;

X5 is lysine or arginine;

X6 is glutamine or tyrosine;

X7 is leucine or methionine;

X8 is aspartic acid or glutamic acid;

X9 is glutamic acid, serine, alpha-methyl-glutamic acid or is deleted;

X10 is glutamine, glutamic acid, lysine, arginine, serine or is deleted;

X11 is alanine, arginine, valine or is deleted;

X12 is alanine, arginine, serine, valine or is deleted;

X13 is lysine, glutamine, arginine, alpha-methyl-glutamic acid or is deleted;

X14 is aspartic acid, glutamic acid, leucine or is deleted;

X15 is phenylalanine or is deleted;

X16 is isoleucine, valine or is deleted;

X17 is alanine, cysteine, glutamic acid, lysine, glutamine, alpha-methyl-glutamic acid or is deleted;

X18 is tryptophan or is deleted;

X19 is alanine, isoleucine, leucine, serine, valine or is deleted;

X20 is alanine, lysine, methionine, glutamine, arginine or is deleted;

X21 is asparagine or is deleted;

X22 is alanine, glycine, threonine or is deleted;

X23 is cysteine, lysine or is deleted;

X24 is a peptide having 2 to 10 amino acids consisting of combinations of alanine, glycine and serine, or is deleted; and R2 is KRNRNNIA (SEQ ID NO: 35), GPSSGAPPPS (SEQ ID NO: 36), GPSSGAPPPSK (SEQ ID NO: 37), HSQGTFTSDYSKYLD (SEQ ID NO: 38), HSQGTFTSDYSRYLDK (SEQ ID NO: 39), HGEGTFTSDLSKQMEEEAVK (SEQ ID NO: 40) or is deleted (excluded if the amino acid sequence of Formula 1 is identical to that of SEQ ID NO. 1).

In order to enhance the activity of the wild-type oxyntomodulin for the glucagon receptor and the GLP-1 receptor, the peptide of the present invention may be substituted with 4-imidazoacetyl where the alpha carbon of histidine at position 1 of amino acid sequence represented by SEQ ID NO. 1 is deleted, desamino-histidyl where the N-terminal amino group is deleted, dimethyl-histidyl (N-dimethyl-histidyl) where the N-terminal amino group is modified with two methyl groups, beta-hydroxy imidazopropionyl where the N-terminal amino group is substituted with a hydroxyl group, or beta-carboxy imidazopropionyl where the N-terminal amino group is substituted with a carboxyl group. In addition, the GLP-1 receptor-binding region may be substituted with amino acids that enhance hydrophobic and ionic bonds or combinations thereof. A part of the oxyntomodulin sequence may be substituted with the amino acid sequence of GLP-1 or Exendin-4 to enhance the activity on GLP-1 receptor.

Further, a part of the oxyntomodulin sequence may be substituted with a sequence stabilizing alpha helix. Preferably, amino acids at positions 10, 14, 16, 20, 24 and 28 of the amino acid sequence of Formula 1 may be substituted with amino acids or amino acid derivatives consisting of Tyr(4-Me), Phe, Phe(4-Me), Phe(4-Cl), Phe(4-CN), Phe(4-NO₂), Phe(4-NH₂), Phg, Pal, Nal, Ala(2-thienyl) and Ala (benzothienyl) that are known to stabilize alpha helix, and there are no limitations on the type and number of alpha helix-stabilizing amino acid or amino acid derivatives to be inserted. Preferably, amino acids at positions 10 and 14, 12 and 16, 16 and 20, 20 and 24, and 24 and 28 may be also substituted with glutamic acid or lysine, respectively so as to form rings, and there is no limitation on the number of rings to be inserted. Most preferably, the peptide may be a peptide having an amino acid sequence selected from the following Formulae 1 to 6.

In one specific embodiment, the oxyntomodulin derivative of the present invention is a novel peptide including the amino acid sequence of the following Formula 2 where the amino acid sequence of oxyntomodulin is substituted with that of exendin or GLP-1.

R1-A-R3 (Formula 2) (SEQ ID NO: 55)

In another specific embodiment, the oxyntomodulin derivative of the present invention is a novel peptide including the amino acid sequence of the following Formula 3, which is prepared by linking a part of the amino acid sequence of oxyntomodulin and a part of the amino acid sequence of exendin or GLP-1 via a proper amino acid linker.

R1-B-C-R4 (Formula 3) (SEQ ID NO: 56)

In still another specific embodiment, the oxyntomodulin derivative of the present invention is a novel peptide including the amino acid sequence of the following Formula 4, wherein a part of the amino acid sequence of oxyntomodulin is substituted with an amino acid capable of enhancing the binding affinity to GLP-1 receptor, for example, Leu at position 26 which binds with GLP-1 receptor by hydrophobic interaction is substituted with the hydrophobic residue, Ile or Val.

R1-SQGTFTSDYSKYLD-D1-D2-D3-D4-D5-
LFVQW-D6-D7-N-D8-R3 (Formula 4) (SEQ ID NO: 57)

In still another specific embodiment, the oxyntomodulin derivative of the present invention is a novel peptide including the following Formula 5, wherein a part of the amino acid sequence is deleted, added, or substituted with other amino acid in order to enhance the activities of native oxyntomodulin on GLP-1 receptor and glucagon receptor.

R1-E1-QGTFTSDYSKYLD-E2-E3-RA-E4-E5-FV-
E6-WLMNT-E7-R5 (Formula 5) (SEQ ID NO: 58)

In Formulae 2 to 5, R1 is the same as in the description of Formula 1;

A is selected from the group consisting of SQGTFTSDYSKYLDSRRAQDFVQWLMNT (SEQ ID NO: 41), SQGTFTSDYSKYLDEEAVRLFIEWLMNT (SEQ ID NO. 42), SQGTFTSDYSKYLDERRAQDFVAWLKNT (SEQ ID NO. 43), GQGTFTSDYSRYLEEEAVRLFIEWLKNG (SEQ ID NO. 44), GQGTFTSDYSRQMEEEAVRLFIEWLKNG (SEQ ID NO. 45), GEGTFTSDLSRQMEEEAVRLFIEWAA (SEQ ID NO. 46), and SQGTFTSDYSRQMEEEAVRLFIEWLMNG (SEQ ID NO. 47);

B is selected from the group consisting of SQGTFTSDYSKYLDSRRAQDFVQWLMNT (SEQ ID NO. 41), SQGTFTSDYSKYLDEEAVRLFIEWLMNT (SEQ ID NO. 42), SQGTFTSDYSKYLDERRAQDFVAWLKNT (SEQ ID NO. 43), GQGTFTSDYSRYLEEEAVRLFIEWLKNG (SEQ ID NO. 44), GQGTFTSDYSRQMEEEAVRLFIEWLKNG (SEQ ID NO. 45), GEGTFTSDLSRQMEEEAVRLFIEWAA (SEQ ID NO. 46), SQGTFTSDYSRQMEEEAVRLFIEWLMNG (SEQ ID NO. 47), GEGTFTSDLSRQMEEEAVRLFIEW (SEQ ID NO. 48), and SQGTFTSDYSRYLD (SEQ ID NO. 49);

C is a peptide having 2 to 10 amino acids consisting of combinations of alanine, glycine and serine;

D1 is serine, glutamic acid or arginine;
D2 is arginine, glutamic acid or serine;
D3 is arginine, alanine or valine;
D4 is arginine, valine or serine;
D5 is glutamine, arginine or lysine;
D6 is isoleucine, valine or serine;
D7 is methionine, arginine or glutamine;
D8 is threonine, glycine or alanine;
E1 is serine, Aib, Sar, d-alanine or d-serine;
E2 is serine or glutamic acid;
E3 is arginine or lysine;
E4 is glutamine or lysine;
E5 is aspartic acid or glutamic acid;
E6 is glutamine, cysteine or lysine;
E7 is cysteine, lysine or is deleted;
R3 is KRNRNNIA (SEQ ID NO. 35), GPSSGAPPPS (SEQ ID NO. 36) or GPSSGAPPPSK (SEQ ID NO. 37);
R4 is HSQGTFTSDYSKYLD (SEQ ID NO. 38), HSQGTFTSDYSRYLDK (SEQ ID NO. 39) or HGEGTFTSDLSKQMEEEAVK (SEQ ID NO. 40); and,
R5 is KRNRNNIA (SEQ ID NO. 35), GPSSGAPPPS (SEQ ID NO. 36), GPSSGAPPPSK (SEQ ID NO. 37) or is deleted (excluded if the amino acid sequences of Formulae 2 to 5 are identical to that of SEQ ID NO. 1).

Preferably, the oxyntomodulin derivative of the present invention may be a noverl peptide of the following Formula 6.

R1-X1-X2-GTFTSD-X3-X4-X5-X6-X7-X8-X9-X10-X11-X12-X13-X14-X15-X16-X17-X18-X19-X20-X21-X22-X23-X24-R2 (Formula 6) (SEQ ID NO: 59)

wherein R1 is histidine, desamino-histidyl, 4-imidazoacetyl or tyrosine;
X1 is Aib(aminosiobutyric acid), glycine or serine;
X2 is glutamic acid or glutamine;
X3 is leucine or tyrosine;
X4 is serine or alanine;
X5 is lysine or arginine;
X6 is glutamine or tyrosine;
X7 is leucine or methionine;
X8 is aspartic acid or glutamic acid;
X9 is glutamic acid, alpha-methyl-glutamic acid or is deleted;
X10 is glutamic acid, glutamic acid, lysine, arginine or is deleted;
X11 is alanine, arginine or is deleted;
X12 is alanine, valine or is deleted;
X13 is lysine, glutamine, arginine, alpha-methyl-glutamic acid or is deleted;
X14 is aspartic acid, glutamic acid, leucine or is deleted;
X15 is phenylalanine or is deleted;
X16 is isoleucine, valine or is deleted;
X17 is alanine, cysteine, glutamic acid, glutamine, alpha-methyl-glutamic acid or is deleted;
X18 is tryptophan or is deleted;
X19 is alanine, isoleucine, leucine, valine or is deleted;
X20 is alanine, lysine, methionine, arginine or is deleted;
X21 is asparagine or is deleted;
X22 is threonine or is deleted;
X23 is cysteine, lysine or is deleted;
X24 is a peptide having 2 to 10 amino acids consisting of glycine or is deleted; and
R2 is KRNRNNIA (SEQ ID NO. 35), GPSSGAPPPS (SEQ ID NO. 36), GPSSGAPPPSK (SEQ ID NO. 37), HSQGTFTSDYSKYLD (SEQ ID NO. 38), HSQGTFTSDYSRYLDK (SEQ ID NO. 39), HGEGTFTSDLSKQMEEEAVK (SEQ ID NO. 40) or is deleted (excluded if the amino acid sequence of Formula 6 is identical to that of SEQ ID NO. 1)

More preferably, the oxyntomodulin derivative of the present invention may be selected from the group consisting of the peptides of SEQ ID NOs. 2 to 34. Much more preferably, the oxyntomodulin derivative of the present invention may be an oxyntomodulin derivative described in Table 1 of Example 2-1.

Oxyntomodulin has the activities of two peptides, GLP-1 and glucagon. GLP-1 decreases blood glucose, reduces food intake, and suppresses gastric emptying, and glucagon increases blood glucose, facilitate lipolysis and decreases body-weight by increasing energy metabolisms. The different biological effects of the two peptides can cause undesired effects like increasing blood glucose if glucagon shows a more dominant effect than GLP-1, or causing nausea and vomiting if GLP-1 shows more dominant effect than glucagon. For example, the conjugate that was produced in Example 10 below showed greater affinity to GLP-1 receptor than the one produced in Example 12, but the efficacy of the former was lower than the latter as shown in the in vivo experiment in Example 18. This might be due to the increased efficacy of the conjugates in relation to the glucagon receptor in Example 12 in spite of its low efficacy in relation to the GLP-1 receptor. Therefore, the oxyntomodulin derivatives and their conjugates of the present invention are not limited to those derivatives which show for unconditional increase of activities. For example, the amino acids can be modified at positions 1 and 11 of oxyntomodulin, which are known to suppress the activity of glucagon, to control the activity ratio between glucagon and GLP-1.

The conjugates of the present invention can induce increased stability in blood, suspend emission through the kidney, and change affinity to receptors by linking a carrier to oxyntomodulin via a covalent bond or forming microsphere. The carrier that can form a conjugate containing oxyntomodulin can be selected from the group consisting of albumin, transferrin, antibodies, antibody fragments, elastin, heparin, polysaccharide such as chitin, fibronectin and most favorably immunoglobulin Fc region, all of which can increase the blood half-life of the conjugates when bound to oxyntomodulin.

The term "immunoglobulin Fc region" as used herein, refers to a protein that contains the heavy-chain constant region 2 (CH2) and the heavy-chain constant region 3 (CH3) of an immunoglobulin, excluding the variable regions of the heavy and light chains, the heavy-chain constant region 1

(CH1) and the light-chain constant region 1 (CL1) of the immunoglobulin. It may further include a hinge region at the heavy-chain constant region. Also, the immunoglobulin Fc region of the present invention may contain a part or all of the Fc region including the heavy-chain constant region 1 (CH1) and/or the light-chain constant region 1 (CL1), except for the variable regions of the heavy and light chains, as long as it has a physiological function substantially similar to or better than the native protein. Also, the immunoglobulin Fc region may be a fragment having a deletion in a relatively long portion of the amino acid sequence of CH2 and/or CH3. That is, the immunoglobulin Fc region of the present invention may comprise 1) a CH1 domain, a CH2 domain, a CH3 domain and a CH4 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), and 6) a dimer of each domain of the heavy-chain constant regions and the light-chain constant region.

The immunoglobulin Fc region of the present invention includes a native amino acid sequence, and a sequence derivative (mutant) thereof. An amino acid sequence derivative is a sequence that is different from the native amino acid sequence due to a deletion, an insertion, a non-conservative or conservative substitution or combinations thereof of one or more amino acid residues. For example, in an IgG Fc, amino acid residues known to be important in binding, at positions 214 to 238, 297 to 299, 318 to 322, or 327 to 331, may be used as a suitable target for modification.

Also, other various derivatives are possible, including one in which a region capable of forming a disulfide bond is deleted, or certain amino acid residues are eliminated at the N-terminal end of a native Fc form or a methionine residue is added thereto. Further, to remove effector functions, a deletion may occur in a complement-binding site, such as a C1q-binding site and an ADCC (antibody dependent cell mediated cytotoxicity) site. Techniques of preparing such sequence derivatives of the immunoglobulin Fc region are disclosed in WO 97/34631 and WO 96/32478.

Amino acid exchanges in proteins and peptides, which do not generally alter the activity of the proteins or peptides, are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in both directions. In addition, the Fc region, if desired, may be modified by phosphorylation, sulfation, acrylation, glycosylation, methylation, farnesylation, acetylation, amidation, and the like.

The aforementioned Fc derivatives are derivatives that have a biological activity identical to the Fc region of the present invention or improved structural stability, for example, against heat, pH, or the like.

In addition, these Fc regions may be obtained from native forms isolated from humans and other animals including cows, goats, pigs, mice, rabbits, hamsters, rats and guinea pigs, or may be recombinants or derivatives thereof, obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)2 fragments. These fragments may be subjected, for example, to size exclusion chromatography to isolate Fc or pF'c. Preferably, a human-derived Fc region is a recombinant immunoglobulin Fc region that is obtained from a microorganism.

In addition, the immunoglobulin Fc region of the present invention may be in the form of having native sugar chains, increased sugar chains compared to a native form or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method using a microorganism. The removal of sugar chains from an Fc region results in a sharp decrease in binding affinity to the C1q part of the first complement component C1 and a decrease or loss in antibody-dependent cell-mediated cytotoxicity or complement-dependent cytotoxicity, thereby not inducing unnecessary immune responses in-vivo. In this regard, an immunoglobulin Fc region in a deglycosylated or aglycosylated form may be more suitable to the object of the present invention as a drug carrier.

As used herein, the term "deglycosylation" refers to enzymatically removing sugar moieties from an Fc region, and the term "aglycosylation" means that an Fc region is produced in an unglycosylated form by a prokaryote, preferably E. coli.

Meanwhile, the immunoglobulin Fc region may be derived from humans or other animals including cows, goats, pigs, mice, rabbits, hamsters, rats and guinea pigs, and preferably from humans.

In addition, the immunoglobulin Fc region may be an Fc region that is derived from IgG, IgA, IgD, IgE and IgM, or that is made by combinations thereof or hybrids thereof. Preferably, it is derived from IgG or IgM, which are among the most abundant proteins in human blood, and most preferably from IgG, which is known to enhance the half-lives of ligand-binding proteins.

On the other hand, the term "combination", as used herein, means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

The term non-peptidyl polymer, refers to a biocompatible polymer including two or more repeating units linked to each other by any covalent bond excluding a peptide bond. In the present invention, the non-peptidyl polymer may be interchangeably used with the non-peptidyl linker.

The non-peptidyl polymer useful in the present invention may be selected from the group consisting of a biodegradable polymer, a lipid polymer, chitin, hyaluronic acid, and a combination thereof, and preferably, the biodegradable polymer may be polyethylene glycol, polypropylene glycol, ethylene glycol-propylene glycol copolymer, polyoxyethylated polyol, polyvinyl alcohol, polysaccharide, dextran, polyvinyl ethyl ether, polylactic acid (PLA) or polylactic-glycolic acid (PLGA), and more preferably, is polyethylene glycol (PEG). In addition, derivatives thereof known in the art and derivatives easily prepared by a method known in the art may be included in the scope of the present invention.

The peptide linker which is used in the fusion protein obtained by a conventional in frame fusion method has drawbacks in that it is easily in-vivo cleaved by a proteolytic enzyme, and thus a sufficient effect of increasing the serum half-life of the active drug by a carrier cannot be obtained as expected. However, in the present invention, the polymer having resistance to the proteolytic enzyme can be used to maintain the serum half-life of the peptide being similar to that of the carrier. Therefore, any non-peptidyl polymer can be used without limitation, as long as it is a polymer having the aforementioned function, that is, a polymer having resistance to the in-vivo proteolytic enzyme. The non-peptidyl polymer has a molecular weight in the range of 1 to 100 kDa, and preferably of 1 to 20 kDa. The non-peptidyl polymer of the present invention, linked to the immunoglobulin Fc region, may be one polymer or a combination of different types of polymers.

The non-peptidyl polymer used in the present invention has a reactive group capable of binding to the immunoglobulin Fc region and protein drug. The non-peptidyl polymer has a reactive group at both ends, which is preferably selected from the group consisting of a reactive aldehyde, a propionaldehyde, a butyraldehyde, a maleimide and a succinimide derivative. The succinimide derivative may be succinimidyl propionate, hydroxy succinimidyl, succinimidyl carboxymethyl, or succinimidyl carbonate. In particular, when the non-peptidyl polymer has a reactive aldehyde group at both ends thereof, it is effective in linking at both ends with a physiologically active polypeptide and an immunoglobulin with minimal non-specific reactions. A final product generated by reductive alkylation by an aldehyde bond is much more stable than that linked by an amide bond. The aldehyde reactive group selectively binds to an N-terminus at a low pH, and binds to a lysine residue to form a covalent bond at a high pH, such as pH 9.0. The reactive groups at both ends of the non-peptidyl polymer may be the same or different. For example, the non-peptidyl polymer may possess a maleimide group at one end, and an aldehyde group, a propionaldehyde group or a butyraldehyde group at the other end. When a polyethylene glycol having a reactive hydroxy group at both ends thereof is used as the non-peptidyl polymer, the hydroxy group may be activated to various reactive groups by known chemical reactions, or a polyethylene glycol having a commercially available modified reactive group may be used so as to prepare the long acting conjugate of the present invention.

The conjugate of the present invention, can be which both ends of the non-peptidyl polymer having two reactive terminal groups are linked to an amine group or thiol group of the immunoglobulin Fc region and oxyntomodulin derivatives, respectively.

The non-peptidyl polymer has a reactive group at both ends, which is preferably selected from the group consisting of a reactive aldehyde group, a propionaldehyde group, a butyraldehyde group, a maleimide group and a succinimide derivative. The succinimide derivative may be succinimidyl propionate, hydroxy succinimidyl, succinimidyl carboxymethyl, or succinimidyl carbonate.

The two reactive terminal groups of the non-peptidyl polymer may be the same as or different from each other. For example, the non-peptide polymer may possess a maleimide group at one end and an aldehyde group, a propionaldehyde group or a butyraldehyde group at the other end. For example, when the non-peptidyl polymer has a reactive aldehyde group at a terminal group, and a maleimide group at the other terminal group, it is effective in linking at both ends with a physiologically active polypeptide and an immunoglobulin with minimal non-specific reactions. According to Examples of the present invention, conjugates were prepared by linking the oxyntomodulin or derivative thereof and the immunoglobulin Fc region via a covalent bond using PEG that is a non-peptidyl polymer including the propionaldehyde group alone or both the maleimides group and the aldehyde group.

The conjugates of the present invention show excellent activity on GLP-1 receptor and glucagon receptor, compared to native oxyntomodulin, and the blood half-life is increased by linking with the Fc region so as to maintain in vivo activity for a long period of time.

In still another aspect, the present invention provides a pharmaceutical composition for the prevention or treatment of obesity comprising the peptide.

As used herein, the term "prevention" means all of the actions by which the occurrence of the disease is restrained or retarded. In the present invention, "prevention" means that the occurrence of obesity from such factors as an increase in body weight or body fat is restrained or retarded by administration of the conjugates of the present invention.

As used herein, the term "treatment" means all of the actions by which the symptoms of the disease have been alleviated, improved or ameliorated. In the present invention, "treatment" means that the symptoms of obesity are alleviated, improved or ameliorated by administration of the conjugates of the present invention, resulting in a reduction in body weight or body fat.

As used herein, the term "obesity" implies accumulation of an excess amount of adipose tissue in the body, and a body mass index (body weight (kg) divided by the square of the height (m)) above 25 is to be regarded as obesity. Obesity is usually caused by an energy imbalance, when the amount of dietary intake exceeds the amount of energy expended for a long period of time. Obesity is a metabolic disease that affects the whole body, and increases the risk for diabetes, hyperlipidemia, sexual dysfunction, arthritis, and cardiovascular diseases, and in some cases, is associated with incidence of cancer.

Figure 12:
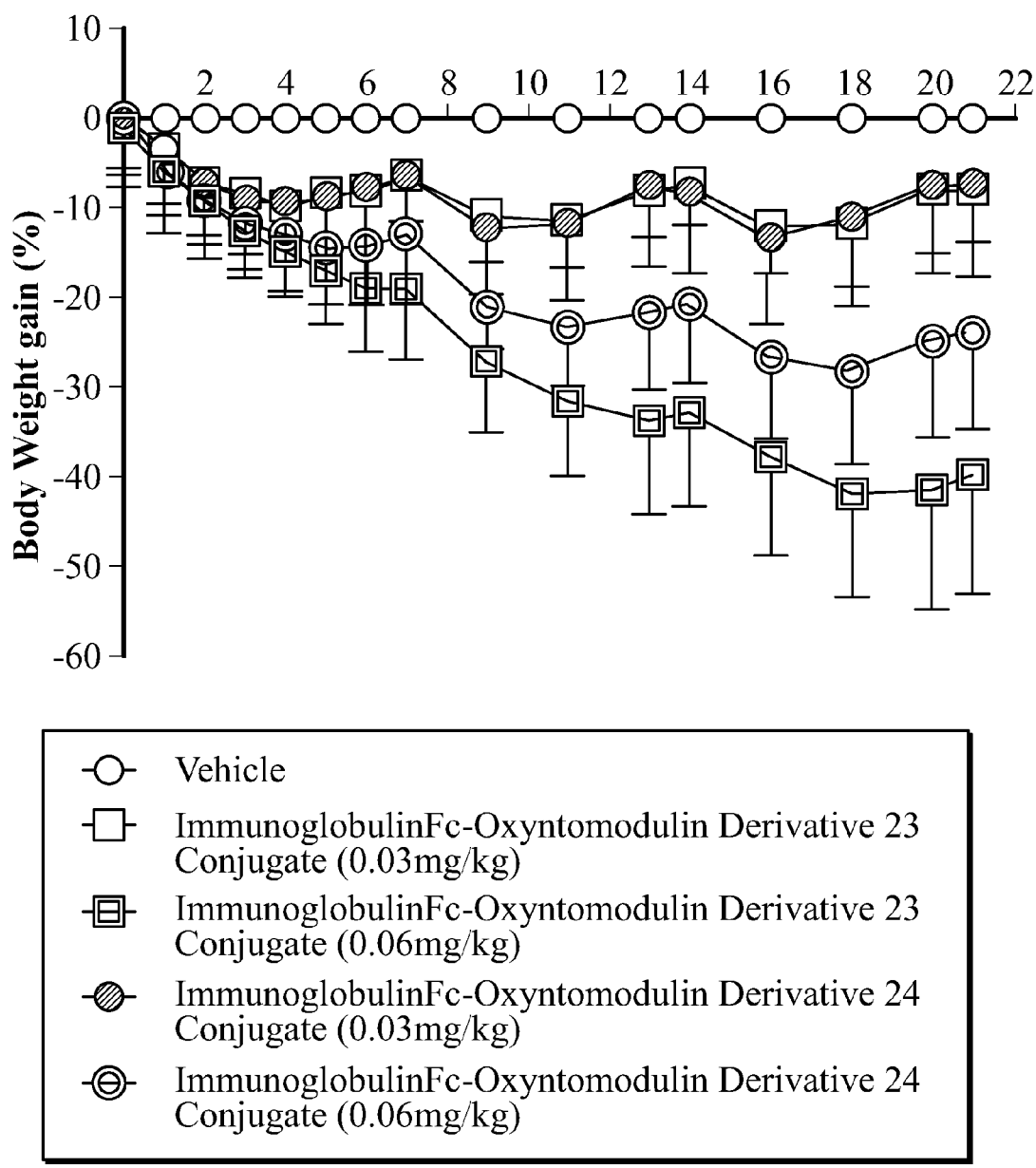
FIG. 12 is a graph showing changes in body weight of mice according to the type and administration dose of oxyntomodulin derivative-immunoglobulin Fc conjugates.

The conjugates of the present invention, which are prepared by linking oxyntomodulin or a derivative thereof with the immunoglobulin Fc region, show excellent binding affinity to glucagon and GLP-1 receptors (Table 3) and excellent resistance to in-vivo proteolytic enzymes so as to exhibit the in vivo activity for a long period of time, thereby showing excellent anti-obesity effects such as reductions in body weight (FIG. 12).

The pharmaceutical composition of the present invention may further include a pharmaceutically acceptable carrier, excipient, or diluent. As used herein, the term "pharmaceutically acceptable" means that the composition is sufficient to achieve the therapeutic effects without deleterious side effects, and may be readily determined depending on the type of the diseases, the patient's age, body weight, health conditions, gender, and drug sensitivity, administration route, administration mode, administration frequency, duration of treatment, drugs used in combination or coincident with the composition of this invention, and other factors known in medicine.

The pharmaceutical composition including the derivative of the present invention may further include a pharmaceutically acceptable carrier. For oral administration, the carrier may include, but is not limited to, a binder, a lubricant, a disintegrant, an excipient, a solubilizer, a dispersing agent, a stabilizer, a suspending agent, a colorant, and a flavorant. For injectable preparations, the carrier may include a buffering agent, a preserving agent, an analgesic, a solubilizer, an isotonic agent, and a stabilizer. For preparations for topical administration, the carrier may include a base, an excipient, a lubricant, and a preserving agent.

The composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into an ampule as a single dosage form or a multidose container. The pharmaceutical composition may also be formulated into solutions, suspensions, tablets, pills, capsules and long-acting preparations.

On the other hand, examples of the carrier, the excipient, and the diluent suitable for the pharmaceutical formulations include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, flavorants, and antiseptics.

Further, the pharmaceutical composition of the present invention may have any formulation selected from the group consisting of tablets, pills, powders, granules, capsules, suspensions, liquids for internal use, emulsions, syrups, sterile aqueous solutions, non-aqueous solvents, lyophilized formulations and suppositories.

Further, the composition may be formulated into a single dosage form suitable for the patient's body, and preferably is formulated into a preparation useful for peptide drugs according to the typical method in the pharmaceutical field so as to be administered by an oral or parenteral route such as through skin, intravenous, intramuscular, intra-arterial, intramedullary, intramedullary, intraventricular, pulmonary, transdermal, subcutaneous, intraperitoneal, intranasal, intracolonic, topical, sublingual, vaginal, or rectal administration, but is not limited thereto.

The composition may be used by blending with a variety of pharmaceutically acceptable carriers such as physiological saline or organic solvents. In order to increase the stability or absorptivity, carbohydrates such as glucose, sucrose or dextrans, antioxidants such as ascorbic acid or glutathione, chelating agents, low molecular weight proteins or other stabilizers may be used.

The administration dose and frequency of the pharmaceutical composition of the present invention are determined by the type of active ingredient, together with various factors such as the disease to be treated, administration route, patient's age, gender, and body weight, and disease severity.

The total effective dose of the composition of the present invention may be administered to a patient in a single dose, or may be administered for a long period of time in multiple doses according to a fractionated treatment protocol. In the pharmaceutical composition of the present invention, the content of active ingredient may vary depending on the disease severity. Preferably, the total daily dose of the peptide of the present invention may be approximately 0.0001 μg to 500 mg per 1 kg of body weight of a patient. However, the effective dose of the peptide is determined considering various factors including patient's age, body weight, health conditions, gender, disease severity, diet, and secretion rate, in addition to administration route and treatment frequency of the pharmaceutical composition. In view of this, those skilled in the art may easily determine an effective dose suitable for the particular use of the pharmaceutical composition of the present invention. The pharmaceutical composition according to the present invention is not particularly limited to the formulation, and administration route and mode, as long as it shows the effects of the present invention.

The pharmaceutical composition of the present invention shows excellent in-vivo duration of efficacy and titer, thereby remarkably reducing the number and frequency of administration thereof.

Moreover, the pharmaceutical composition may be administered alone or in combination or coincident with other pharmaceutical formulations showing prophylactic or therapeutic effects on obesity. The pharmaceutical formulations showing prophylactic or therapeutic effects on obesity are not particularly limited, and may include a GLP-1 receptor agonist, a leptin receptor agonist, a DPP-IV inhibitor, a Y5 receptor antagonist, a Melanin-concentrating hormone (MCH) receptor antagonist, a Y2/3 receptor agonist, a MC3/4 receptor agonist, a gastric/pancreatic lipase inhibitor, a 5HT2c agonist, a β3A receptor agonist, an Amylin receptor agonist, a Ghrelin antagonist, and/or a Ghrelin receptor antagonist.

In still another aspect, the present invention provides a method for preventing or treating obesity, comprising the step of administering to a subject the conjugate or the pharmaceutical composition including the same.

As used herein, the term "administration" means introduction of an amount of a predetermined substance into a patient by a certain suitable method. The composition of the present invention may be administered via any of the common routes, as long as it is able to reach a desired tissue, for example, but is not limited to, intraperitoneal, intravenous, intramuscular, subcutaneous, intradermal, oral, topical, intranasal, intrapulmonary, or intrarectal administration. However, since peptides are digested upon oral administration, active ingredients of a composition for oral administration should be coated or formulated for protection against degradation in the stomach.

In the present invention, the term "subject" is those suspected of having obesity, which means mammals including human, mouse, and livestock having obesity or having the possibility of obesity. However, any subject to be treated with the peptide or the pharmaceutical composition of the present invention is included without limitation. The pharmaceutical composition including the peptide of the present invention is administered to a subject suspected of having obesity, thereby treating the subject effectively. The obesity is as described above.

The therapeutic method of the present invention may include the step of administering the composition including the peptide at a pharmaceutically effective amount. The total daily dose should be determined through appropriate medical judgment by a physician, and administered once or several times. With respect to the objects of the present invention, the specific therapeutically effective dose level for any particular patient may vary depending on various factors well known in the medical art, including the kind and degree of the response to be achieved, concrete compositions according to whether other agents are used therewith or not, the patient's age, body weight, health condition, gender, and diet, the time and route of administration, the secretion rate of the composition, the time period of therapy, other drugs used in combination or coincident with the composition of this invention, and like factors well known in the medical arts.

In still another aspect, the present invention provides a use of the conjugate or the pharmaceutical composition including the same in the preparation of drugs for the prevention or treatment of obesity.

MODE FOR INVENTION

Hereinafter, the present invention will be described in more detail with reference to the following Examples. However, these Examples are for illustrative purposes only, and the invention is not intended to be limited by these Examples.

Example 1. Production of In Vitro Activated Cell Line

Example 1-1: Production of Cell Line Showing cAMP Response to GLP-1

PCR was performed using a region corresponding to ORF (Open Reading Frame) in cDNA (OriGene Technologies, Inc. USA) of human GLP-1 receptor gene as a template, and the following forward and reverse primers including each of the HindIII and EcoRI restriction sites so as to obtain a PCR product.

```
Forward primer:
                                 (SEQ ID NO. 50)
5'-CCCGGCCCCCGCGGCCGCTATTCGAAATAC-3

Reverse primer:
                                 (SEQ ID NO. 51)
5'-GAACGGTCCGGAGGACGTCGACTCTTAAGATAG-3'
```

The PCR product was cloned into the known animal cell expression vector x0GC/dhfr to prepare a recombinant vector x0GC/GLP1R.

CHO DG44 cell line cultured in DMEM/F12 (10% FBS) medium was transfected with the recombinant vector x0GC/GLP1R using LIPOFECTAMINE® (INVITROGEN®, USA), and cultured in a selection medium containing 1 mg/mL G418 and 10 nM methotraxate. Single clone cell lines were selected therefrom by a limit dilution technique, and a cell line showing excellent cAMP response to GLP-1 in a concentration-dependent manner was finally selected therefrom.

Example 1-2: Production of Cell Line Showing cAMP Response to Glucagon

PCR was performed using a region corresponding to ORF in cDNA (OriGene Technologies, Inc. USA) of human glucagon receptor gene as a template, and the following forward and reverse primers including each of the EcoRI and XhoI restriction sites so as to obtain a PCR product.

```
Forward primer:
                                 (SEQ ID NO. 52)
5'-CAGCGACACCGACCGTCCCCCCGTACTTAAGGCC-3'

Reverse primer:
                                 (SEQ ID NO. 53)
5'-CTAACCGACTCTCGGGGAAGACTGAGCTCGCC-3'
```

The PCR product was cloned into the known animal cell expression vector x0GC/dhfr to prepare a recombinant vector x0GC/GCGR.

CHO DG44 cell line cultured in DMEM/F12 (10% FBS) medium was transfected with the recombinant vector x0GC/GCGR using LIPOFECTAMINE®, and cultured in a selection medium containing 1 mg/mL G418 and 10 nM methotraxate. Single clone cell lines were selected therefrom by a limit dilution technique, and a cell line showing excellent cAMP response to glucagon in a concentration-dependent manner was finally selected therefrom.

Example 2. Test on In Vitro Activity of Oxyntomodulin Derivatives

Example 2-1: Synthesis of Oxyntomodulin Derivatives

In order to measure in vitro activities of oxyntomodulin derivatives, oxyntomodulin derivatives having the following amino acid sequences were synthesized (Table 1).

TABLE 1

| Oxyntomodulin and oxyntomodulin derivatives | |
|---|---|
| SEQ ID NO. | Amino acid sequence |
| SEQ ID NO. 1 | HSQGTFTSDYSKYLDSRRAQDFVQWLMNTKRNRNNIA |
| SEQ ID NO. 2 | CA-SQGTFTSDYSKYLDEEAVRLFIEWLMNTKRNRNNIA |
| SEQ ID NO. 3 | CA-SQGTFTSDYSKYLDERRAQDFVAWLKNTGPSSGAPPPS |
| SEQ ID NO. 4 | CA-GQGTFTSDYSRYLEEEAVRLFIEWLKNGGPSSGAPPPS |
| SEQ ID NO. 5 | CA-GQGTFTSDYSRQMEEEAVRLFIEWLKNGGPSSGAPPPS |
| SEQ ID NO. 6 | CA-GEGTFTSDLSRQMEEEAVRLFIEWAAHSQGTFTSDYSKYLD |
| SEQ ID NO. 7 | CA-SQGTFTSDYSRYLDEEAVRLFIEWLMNTK |
| SEQ ID NO. 8 | CA-SQGTFTSDLSRQLEEEAVRLFIEWLMNK |
| SEQ ID NO. 9 | CA-GQGTFTSDYSRYLDEEAVXLFIEWLMNTKRNRNNIA |
| SEQ ID NO. 10 | CA-SQGTFTSDYSRQMEEEAVRLFIEWLMNGGPSSGAPPPSK |
| SEQ ID NO. 11 | CA-GEGTFTSDLSRQMEEEAVRLFIEWAAHSQGTFTSDYSRYLDK |

TABLE 1-continued

Oxyntomodulin and oxyntomodulin derivatives

| SEQ ID NO. | Amino acid sequence |
|---|---|
| SEQ ID NO. 12 | CA-SQGTFTSDYSRYLDGGGHGEGTFTSDLSKQMEEEAVK |
| SEQ ID NO. 13 | CA-SQGTFTSDYSRYLDXEAVXLFIEWLMNTK |
| SEQ ID NO. 14 | CA-GQGTFTSDYSRYLDEEAVXLFIXWLMNTKRNRNNIA |
| SEQ ID NO. 15 | CA-GQGTFTSDYSRYLDEEAVRLFIXWLMNTKRNRNNIA |
| SEQ ID NO. 16 | CA-SQGTFTSDLSRQLEGGGHSQGTFTSDLSRQLEK |
| SEQ ID NO. 17 | CA-SQGTFTSDYSRYLDEEAVRLFIEWIRNTKRNRNNIA |
| SEQ ID NO. 18 | CA-SQGTFTSDYSRYLDEEAVRLFIEWIRNGGPSSGAPPPSK |
| SEQ ID NO. 19 | CA-SQGTFTSDYSRYLDEEAVKLFIEWIRNTKRNRNNIA |
| SEQ ID NO. 20 | CA-SQGTFTSDYSRYLDEEAVKLFIEWIRNGGPSSGAPPPSK |
| SEQ ID NO. 21 | CA-SQGTFTSDYSRQLEEEAVRLFIEWVRNTKRNRNNIA |
| SEQ ID NO. 22 | DA-SQGTFTSDYSKYLDEKRAKEFVQWLMNTK |
| SEQ ID NO. 23 | HAibQGTFTSDYSKYLDEKRAKEFVCWLMNT |
| SEQ ID NO. 24 | HAibQGTFTSDYSKYLDEKRAKEFVQWLMNTC |
| SEQ ID NO. 25 | HAibQGTFTSDYSKYLDEKRAKEFVQWLMNTC |
| SEQ ID NO. 26 | HAibQGTFTSDYSKYLDEKRAKEFVQWLMNTC |
| SEQ ID NO. 27 | HAibQGTFTSDYSKYLDEQAAKEFICWLMNT |
| SEQ ID NO. 28 | HAibQGTFTSDYSKYLDEKRAKEFVQWLMNT |
| SEQ ID NO. 29 | H(d)SQGTFTSDYSKYLDSRRAQDFVQWLMNTKRNRNNIA |
| SEQ ID NO. 30 | CA-SQGTFTSDYSKYLDSRRAQDFVQWLMNTKRNRNNIA |
| SEQ ID NO. 31 | CA-(d)SQGTFTSDYSKYLDSRRAQDFVQWLMNTKRNRNNIA |
| SEQ ID NO. 32 | CA-AibQGTFTSDYSKYLDEKRAKEFVQWLMNTC |
| SEQ ID NO. 33 | HAibQGTFTSDYAKYLDEKRAKEFVQWLMNTC |
| SEQ ID NO. 34 | YAibQGTFTSDYSKYLDEKRAKEFVQWLMNTC |

In Table 1, amino acids in bold and underlined represent ring formation, and amino acids represented by X mean a non-native amino acid, alpha-methyl-glutamic acid. In addition, CA represents 4-imidazoacetyl, and DA represents desamino-histidyl.

Example 2-2: Test on In Vitro Activity of Oxyntomodulin Derivatives

In order to measure anti-obesity efficacies of the oxyntomodulin derivatives synthesized in Example 2-1, cell activity was measured in vitro using the cell lines prepared in Examples 1-1 and 1-2.

The cell lines were those prepared by transfecting CHO (Chinese Hamster Ovary) to express human GLP-1 receptor gene and glucagon receptor gene, respectively. Thus, they are suitable to measure GLP-1 and glucagon activities. Therefore, the activity of each oxyntomodulin derivative was measured using each transformed cell line.

Specifically, each cell line was sub-cultured twice or three time a week, and aliquoted in each well of a 96-well plate at a density of $1\times10^5$, followed by cultivation for 24 hours.

The cultured cells were washed with KRB buffer and suspended in 40 ml of KRB buffer containing 1 mM IBMX, and left at room temperature for 5 minutes. Oxyntomodulin (SEQ ID NO. 1) and oxyntomodulin derivatives (represented by SEQ ID NOs. 2-6, 8, 10-13, 17, 18, 23-25, 27, 28 and 32-34) were diluted from 1000 nM to 0.02 nM by 5-fold serial dilution, and each 40 mL thereof was added to the cells, and cultured at 37° C. for 1 hour in a $CO_2$ incubator. Then, 20 mL of cell lysis buffer was added for cell lysis, and the cell lysates were applied to a cAMP assay kit (Molecular Device, USA) to measure cAMP concentrations. $EC_{50}$ values were calculated therefrom, and compared to each other. $EC_{50}$ values are shown in the following Table 2.

TABLE 2

Comparison of in vitro activities for GLP-1 receptor and glucagon receptor between oxyntomodulin and oxyntomodulin derivatives

| | $EC_{50}$(nM) | |
|---|---|---|
| SEQ ID NO. | CHO/GLP-1R | CHO/GCGR |
| SEQ ID NO. 1 | 50-210 | 10-43 |
| SEQ ID NO. 2 | 51.8 | 12.8 |
| SEQ ID NO. 3 | >1,000 | 637.7 |
| SEQ ID NO. 4 | 5.5 | >1,000 |

TABLE 2-continued

Comparison of in vitro activities for GLP-1 receptor and glucagon receptor between oxyntomodulin and oxyntomodulin derivatives

| SEQ ID NO. | EC$_{50}$(nM) | |
|---|---|---|
| | CHO/GLP-1R | CHO/GCGR |
| SEQ ID NO. 5 | 5.9 | >1,000 |
| SEQ ID NO. 6 | 500.1 | >1,000 |
| SEQ ID NO. 8 | 419.6 | >1,000 |
| SEQ ID NO. 10 | >1,000 | >1,000 |
| SEQ ID NO. 11 | >1,000 | >1,000 |
| SEQ ID NO. 12 | >1,000 | >1,000 |
| SEQ ID NO. 13 | >1,000 | >1,000 |
| SEQ ID NO. 17 | 97.9 | >1,000 |
| SEQ ID NO. 18 | 96.3 | >1,000 |
| SEQ ID NO. 23 | 2.46 | 5.8 |
| SEQ ID NO. 24 | 1.43 | 6.95 |
| SEQ ID NO. 25 | 1.9 | 1.3 |
| SEQ ID NO. 27 | 2.8-5.5 | 3.1-5.6 |
| SEQ ID NO. 28 | 3.1 | 0.3 |
| SEQ ID NO. 32 | 14.25 | 17.3 |
| SEQ ID NO. 33 | 2.20 | 80.2 |
| SEQ ID NO. 34 | 12.5 | 1.0 |

As shown in Table 2, there were oxyntomodulin derivatives showing excellent in vitro activities and different ratios of activities on GLP-1 receptor and glucagon receptor, compared to native oxyntomodulin of SEQ ID NO. 1.

It is known that oxyntomodulin activates both the GLP-1 receptor and glucagon receptor to suppress appetite, facilitate lipolysis, and promote satiety, thereby showing anti-obesity effects. The oxyntomodulin derivatives according to the present invention show higher in vitro activities on both the GLP-1 receptor and glucagon receptor than the wild-type oxyntomodulin, and therefore can be used as a therapeutic agent for obesity with higher efficacies than the known oxyntomodulin.

Example 3. Test on In Vivo Activity of Oxyntomodulin Derivatives

In order to measure in vivo therapeutic activity of oxyntomodulin derivatives, changes in food intake by administration of oxyntomodulin derivatives were examined in ob/ob mouse using native oxyntomodulin as a control.

Specifically, obese diabetic ob/ob mice, commonly used to test the efficacies of therapeutic agents for obesity and diabetes, were fasted for 16 hours, and administered with 1 or 10 mg/kg of oxyntomodulin, or 0.02, 0.1, 1 or 10 mg/kg of the oxyntomodulin derivative of SEQ ID NO. 2. Then, food intake was examined for 2 hours (FIG. 1). FIG. 1 is a graph showing changes in food intake according to administration dose of oxyntomodulin or oxyntomodulin derivative. As shown in FIG. 1, administration of 1 mg/kg of oxyntomodulin derivative showed more excellent inhibitory effects on food intake than administration of 10 mg/kg of oxyntomodulin.

Taken together, the oxyntomodulin derivatives of the present invention have much higher anti-obesity effects than the wild-type oxyntomodulin, even though administered at a lower dose, indicating improvement in the problems of the wild-type oxyntomodulin that shows lower anti-obesity effects and should be administered at a high dose three times a day.

Figure 2A:
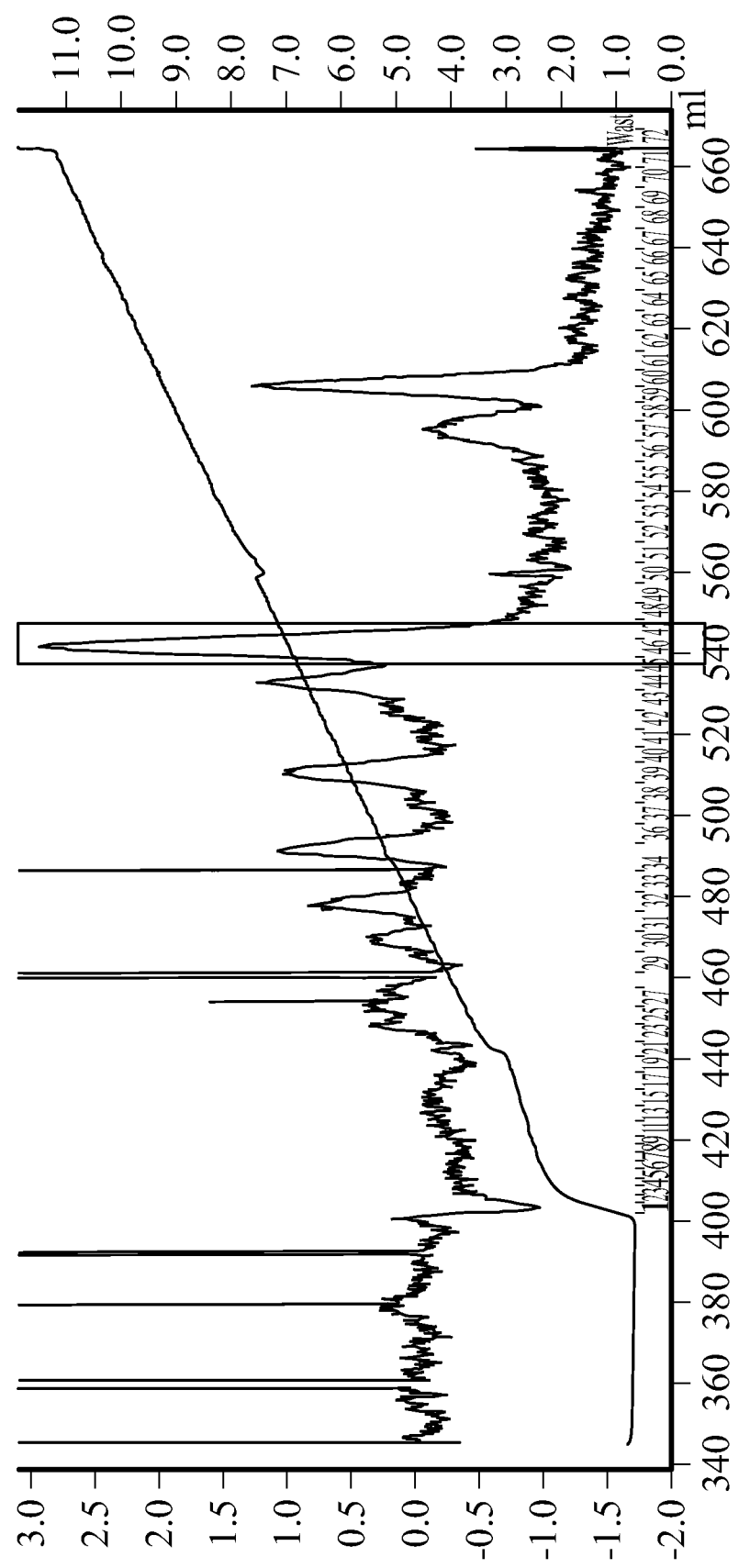
FIG. 2a is a graph showing the result of purifying mono-PEGylated oxyntomodulin through a SOURCE S purification column.
Figure 2B:
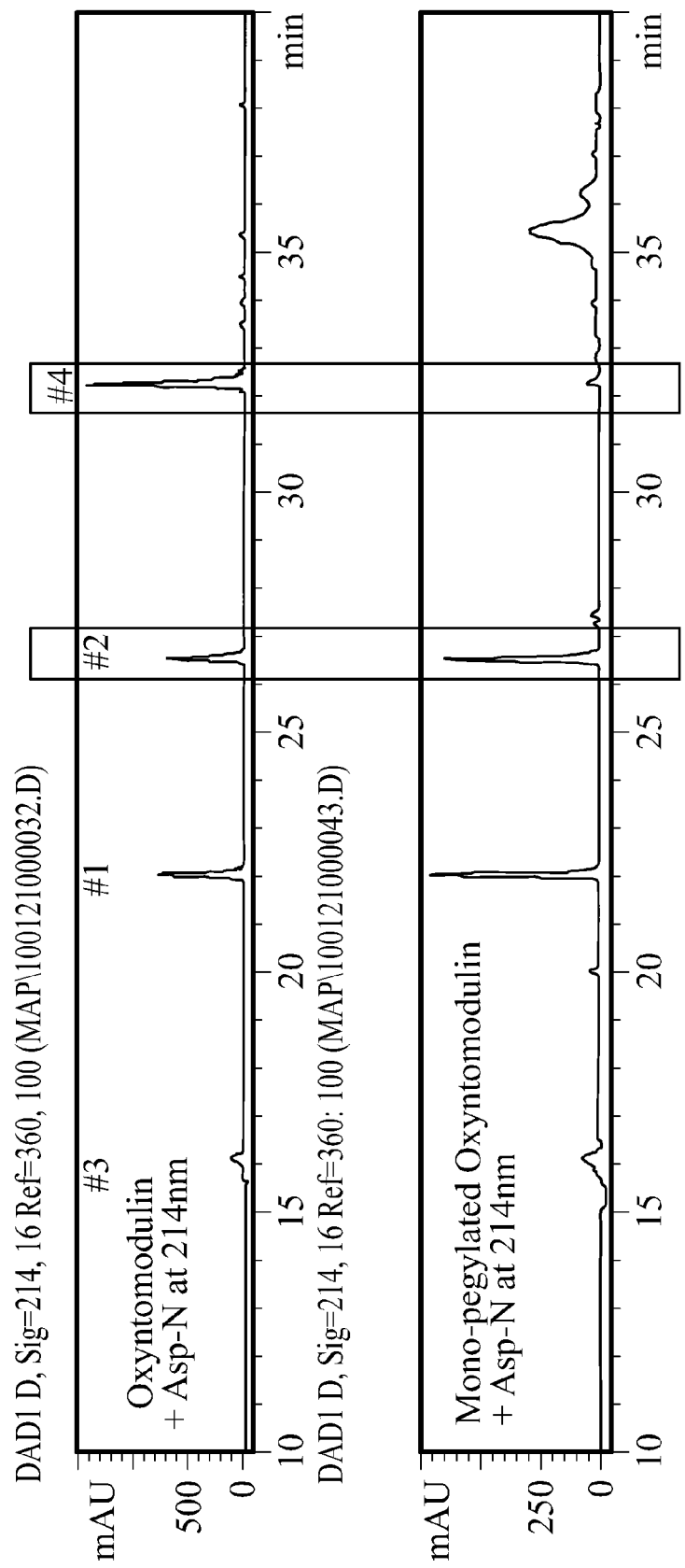
FIG. 2b is a graph showing the result of peptide mapping of purified mono-PEGylated oxyntomodulin.

Example 4: Preparation of Conjugates Including Oxyntomodulin and Immunoglobulin Fc Firstly, for PEGylation of lysine residue at position 30 of the amino acid sequence of oxyntomodulin (SEQ ID NO. 1) with 3.4 K PropionALD(2) PEG (PEG with two propylaldehyde groups, NOF, Japan), the oxyntomodulin and 3.4 K PropionALD(2) PEG were reacted at a molar ratio of 1:12 with the protein concentration of 5 mg/ml at 4° C. for 4.5 hours. At this time, the reaction was conducted in a solvent mixture of 100 mM Na-Borate buffer (pH 9.0) and 45% isopropanol, and 20 mM sodium cyanoborohydride (cyanoborohydride (SCB, NaCNBH$_3$), NaCNBH$_3$) was added thereto as a reducing agent. After completion of the reaction, the reaction mixture was applied to a SOURCE S (XK16, Amersham Biosciences) to purify oxyntomodulin having mono-pegylated lysine (column: SOURCE S (XK16, Amersham Biosciences), flow rate: 2.0 ml/min, gradient: A 0→3% 1 min B→40% 222 min B (A: 20 mM Na-citrate, pH 3.0+45% ethanol, B: A+1M KCl)) (FIG. 2a). FIG. 2a is a graph showing the result of purifying mono-PEGylated oxyntomodulin through a SOURCE S purification column. Mono-PEGylation of the eluted peaks was examined by SDS-PAGE, and lysine selectivity was examined by peptide mapping using Asp-N protease (FIG. 2b). FIG. 2b is a graph showing the result of peptide mapping of purified mono-PEGylated oxyntomodulin.

Figure 2C:
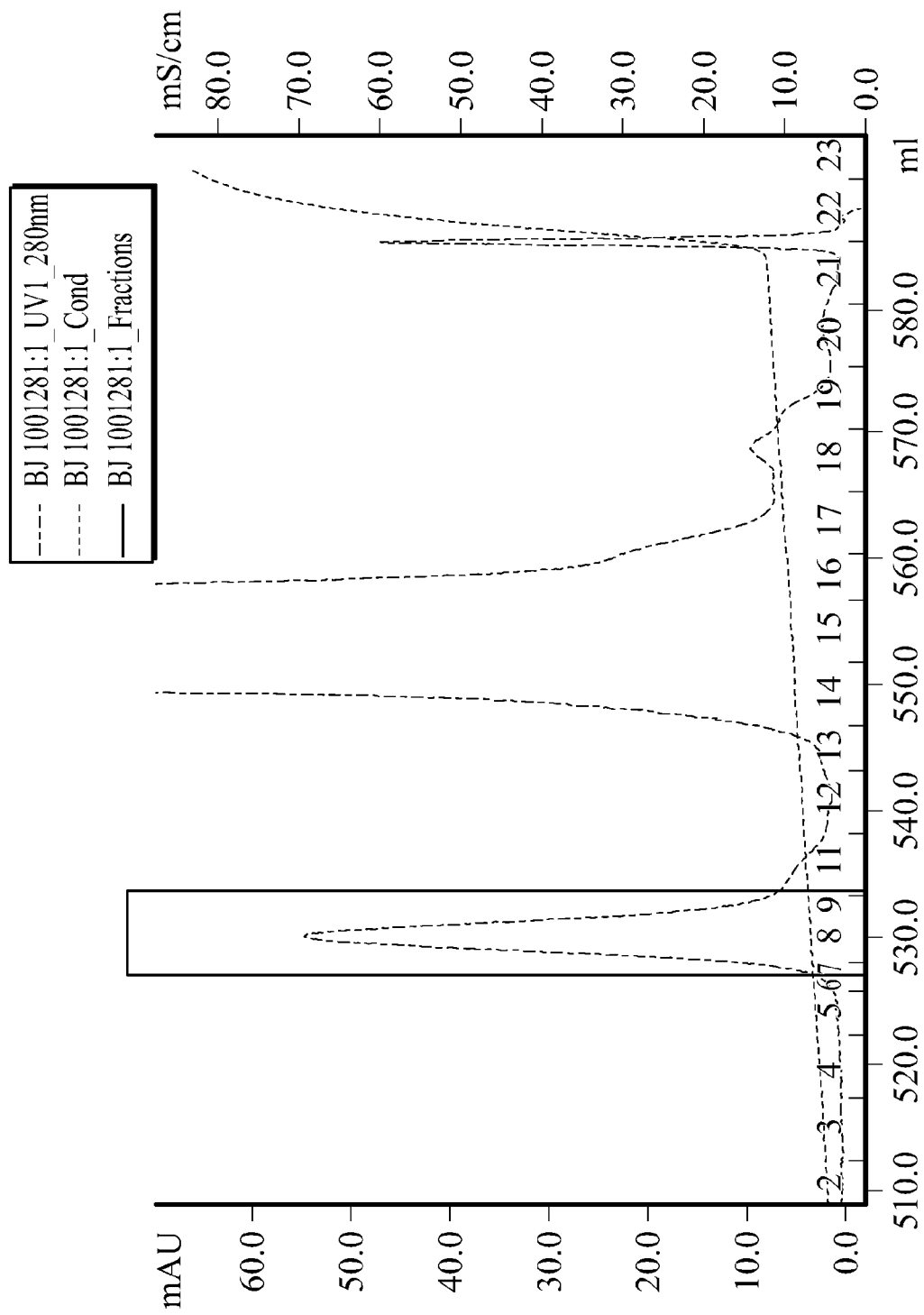
FIG. 2c is a graph showing the result of purifying conjugates including oxyntomodulin and immunoglobulin Fc through a SOURCE 15Q purification column.

Next, the purified mono-PEGylated oxyntomodulin and immunoglobulin Fc were reacted at a molar ratio of 1:10 with the protein concentration of 20 mg/ml at 4° C. for 16 hours. At this time, the reaction was conducted in 100 mM potassium phosphate buffer (pH 6.0) and 20 mM SCB was added thereto as a reducing agent. After completion of the reaction, the reaction mixture was applied to a SOURCE 15Q purification column to purify conjugates including oxyntomodulin and immunoglobulin Fc (column: SOURCE 15Q (XK16, Amersham Biosciences), flow rate: 2.0 ml/min, gradient: A 0→20% 100 min B (A: 20 mM Tris-HCl, pH 7.5, B: A+1M NaCl)) (FIG. 2c). FIG. 2c is a graph showing the result of purifying conjugates including oxyntomodulin and immunoglobulin Fc.

Figure 3A:
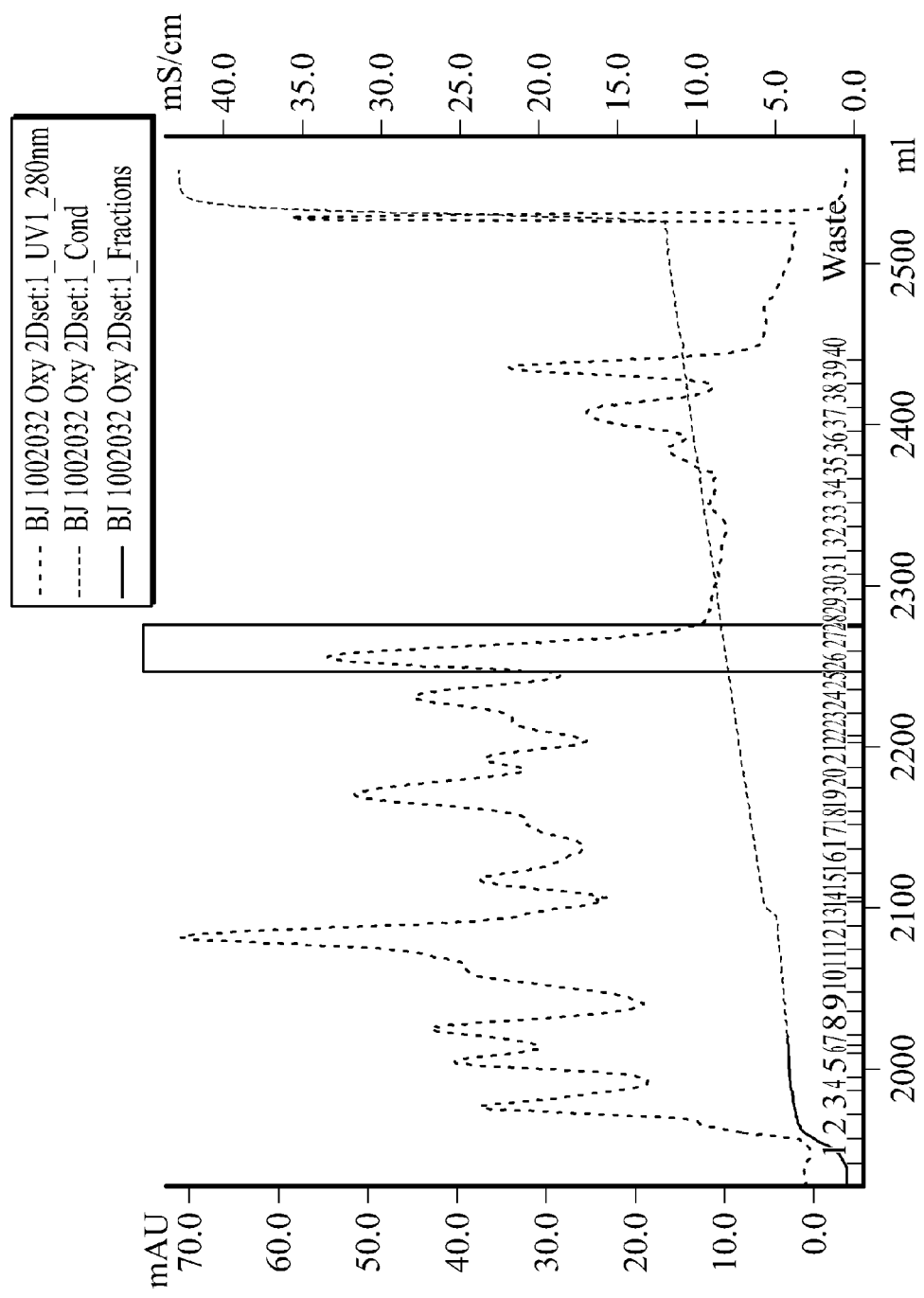
FIG. 3a is a graph showing the result of purifying a mono-PEGylated oxyntomodulin derivative (SEQ ID NO. 29) through a SOURCE S purification column.

Example 5: Preparation of Conjugates Including Oxyntomodulin Derivative (SEQ ID NO. 29) and Immunoglobulin Fc Firstly, for PEGylation of lysine residue at position 30 of the amino acid sequence of oxyntomodulin derivative (SEQ ID NO. 29) with 3.4 K PropionALD(2) PEG, the oxyntomodulin derivative (SEQ ID NO. 29) and 3.4 K PropionALD(2) PEG were reacted at a molar ratio of 1:12 with the protein concentration of 5 mg/ml at 4° C. for 4.5 hours. At this time, the reaction was conducted in a solvent mixture of 100 mM Na-Borate buffer (pH 9.0) and 45% isopropanol, and 20 mM SCB was added thereto as a reducing agent. After completion of the reaction, the reaction mixture was applied to a SOURCE S to purify the oxyntomodulin derivative having mono-pegylated lysine (Column: SOURCE S, flow rate: 2.0 ml/min, gradient: A 0→3% 1 min B→40% 222 min B (A: 20 mM Na-citrate, pH 3.0+45% ethanol, B: A+1M KCl)) (FIG. 3a). FIG. 3a is a graph showing the result of purifying a mono-PEGylated oxyntomodulin derivative (SEQ ID NO. 29) through a SOURCE S purification column.

Figure 3B:
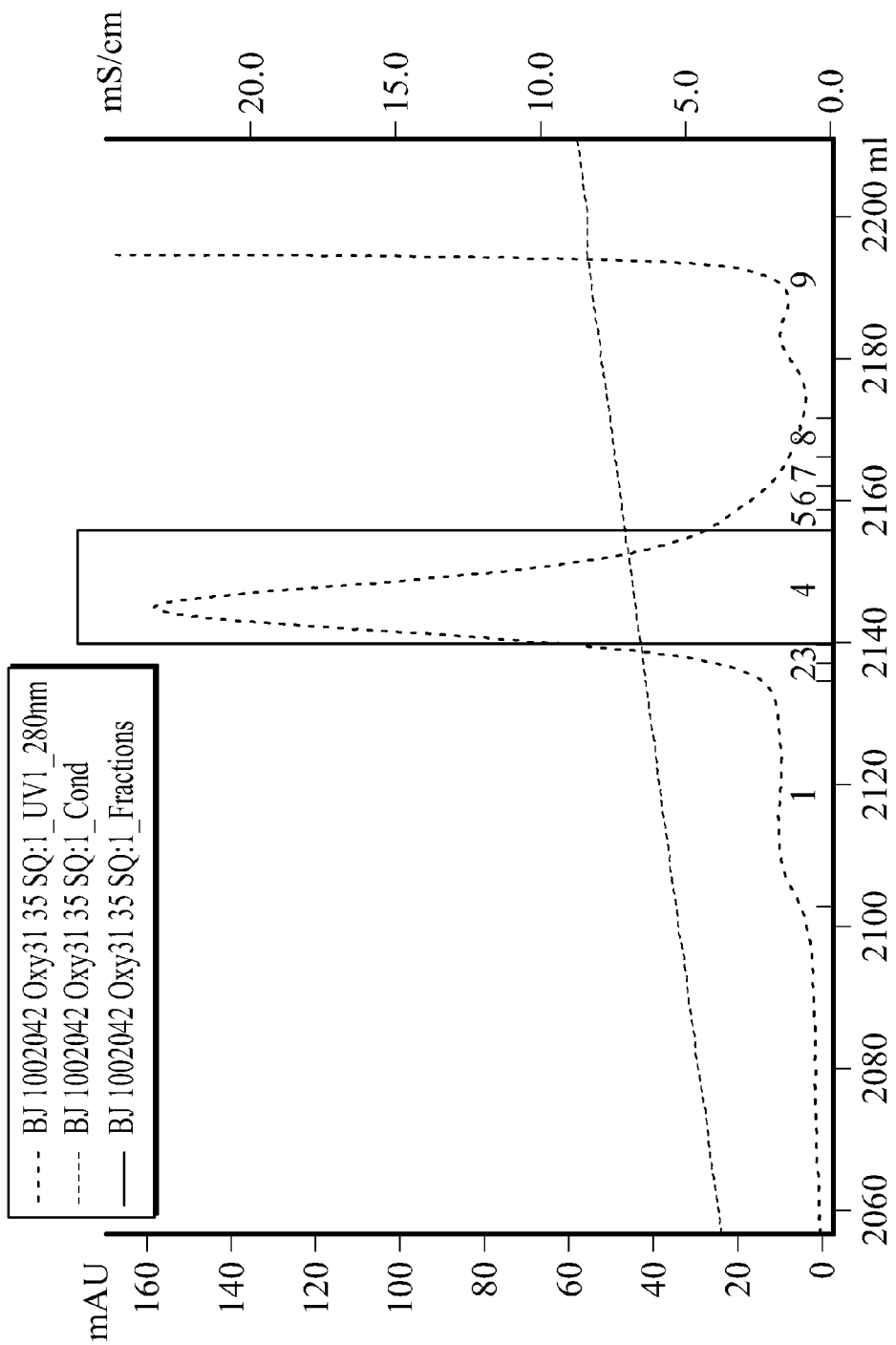
FIG. 3b is a graph showing the result of purifying conjugates including oxyntomodulin derivative (SEQ ID NO. 29) and immunoglobulin Fc through a SOURCE 15Q purification column.

Next, the purified mono-PEGylated oxyntomodulin derivative (SEQ ID NO. 29) and immunoglobulin Fc were reacted at a molar ratio of 1:10 with the protein concentration of 20 mg/ml at 4° C. for 16 hours. At this time, the reaction was conducted in 100 mM potassium phosphate buffer (pH 6.0) and 20 mM SCB was added thereto as a reducing agent. After completion of the reaction, the reaction mixture was applied to a SOURCE 15Q purification column to purify conjugates including oxyntomodulin derivative (SEQ ID NO. 29) and immunoglobulin Fc (column: SOURCE 15Q, flow rate: 2.0 ml/min, gradient: A 0→20% 100 min B (A: 20 mM Tris-HCl, pH 7.5, B: A+1M NaCl)) (FIG. 3b). FIG. 3b is a graph showing the result of purifying conjugates including oxyntomodulin derivative (SEQ ID NO. 29) and immunoglobulin Fc.

Figure 4A:
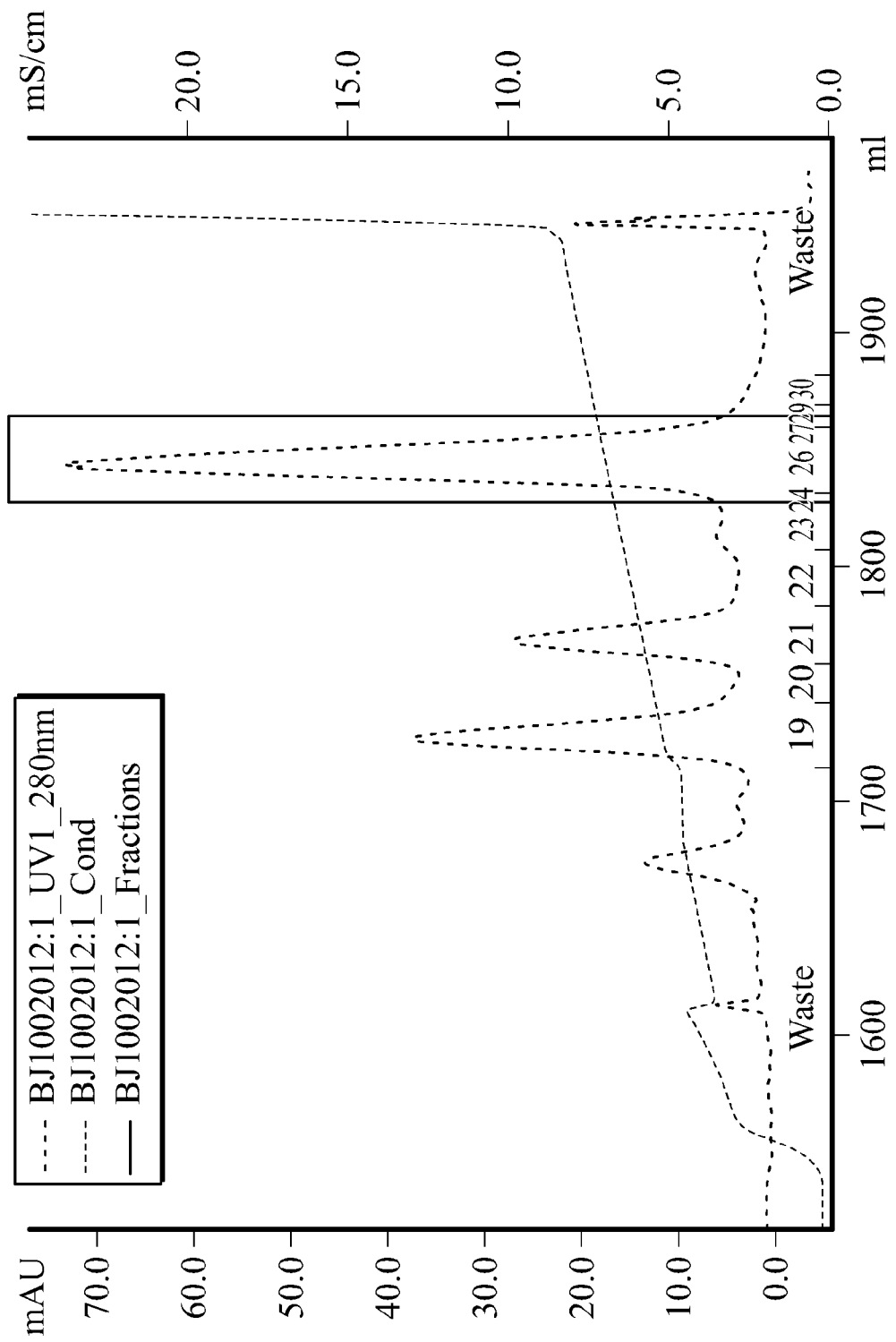
FIG. 4a is a graph showing the result of purifying a mono-PEGylated oxyntomodulin derivative (SEQ ID NO. 30) through a SOURCE S purification column.
Figure 4B:
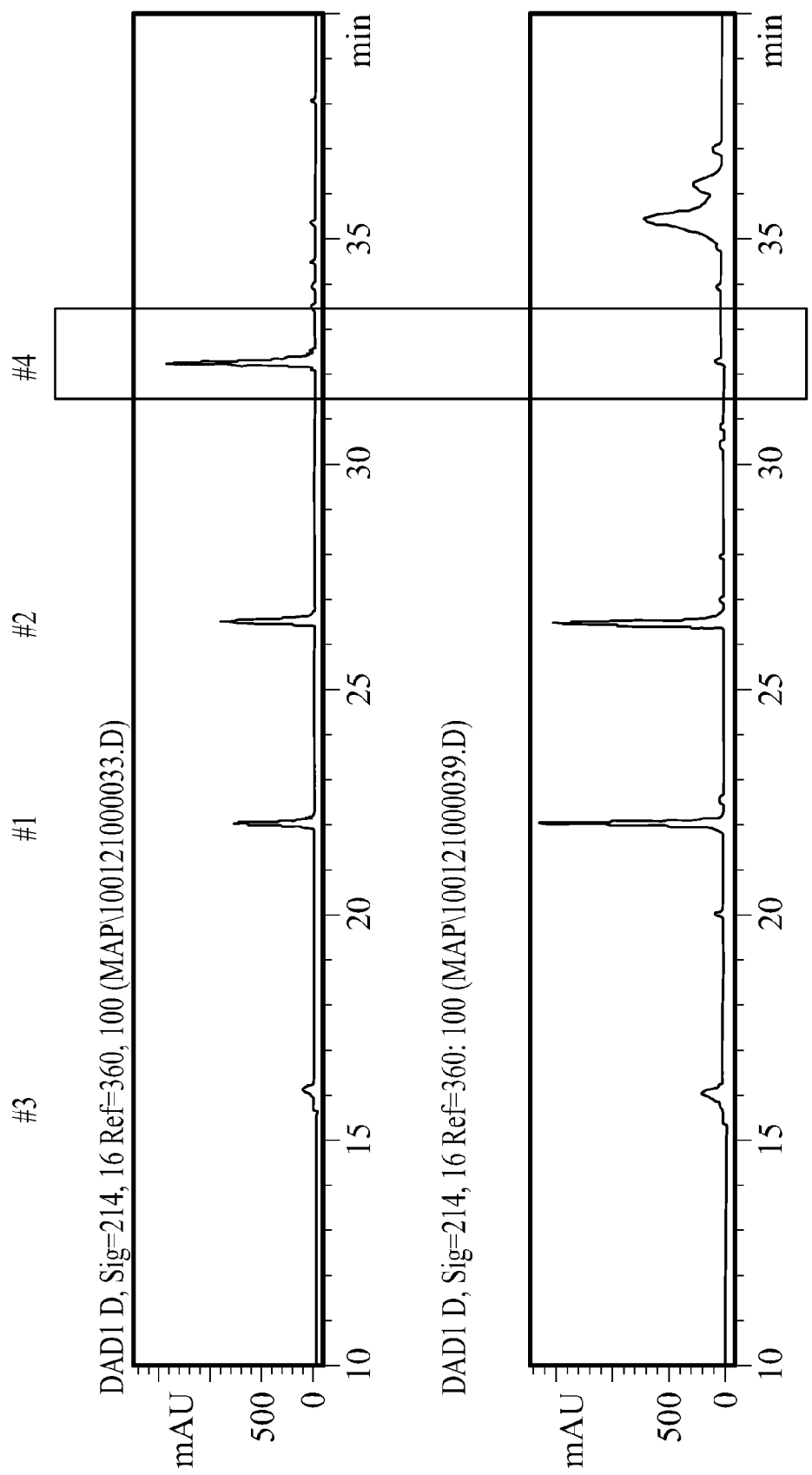
FIG. 4b is a graph showing the result of peptide mapping of purified mono-PEGylated oxyntomodulin derivative (SEQ ID NO. 30).

Example 6: Preparation of Conjugates Including Oxyntomodulin Derivative (SEQ ID NO. 30) and Immunoglobulin Fc Firstly, for PEGylation of lysine residue at position 30 of the amino acid sequence of oxyntomodulin derivative (SEQ ID NO. 30) with 3.4 K PropionALD(2) PEG, the oxyntomodulin derivative (SEQ ID NO. 30) and 3.4 K PropionALD(2) PEG were reacted at a molar ratio of 1:15 with the protein concentration of 3 mg/ml at 4° C. for 4.5 hours. At this time, the reaction was conducted in a solvent mixture of 100 mM HEPES buffer (pH 7.5) and 45% isopropanol, and 20 mM SCB was added thereto as a reducing agent. After completion of the reaction, the reaction mixture was applied to a SOURCE Spurification column to purify the oxyntomodulin derivative having mono-pegylated lysine (Column: SOURCE S, flow rate: 2.0 ml/min, gradient: A 0→3% 1 min B→40% 222 min B (A: 20 mM Na-citrate, pH 3.0+45% ethanol, B: A+1M KCl)) (FIG. 4a). FIG. 4a is a graph showing the result of purifying a mono-PEGylated oxyntomodulin derivative (SEQ ID NO. 30) through a SOURCE S purification column. Mono-PEGylation of the eluted peaks was examined by SDS-PAGE, and lysine selectivity was examined by peptide mapping using Asp-N protease (FIG. 4b). FIG. 4b is a graph showing the result of peptide mapping of purified mono-PEGylated oxyntomodulin derivative (SEQ ID NO. 30).

Figure 4C:
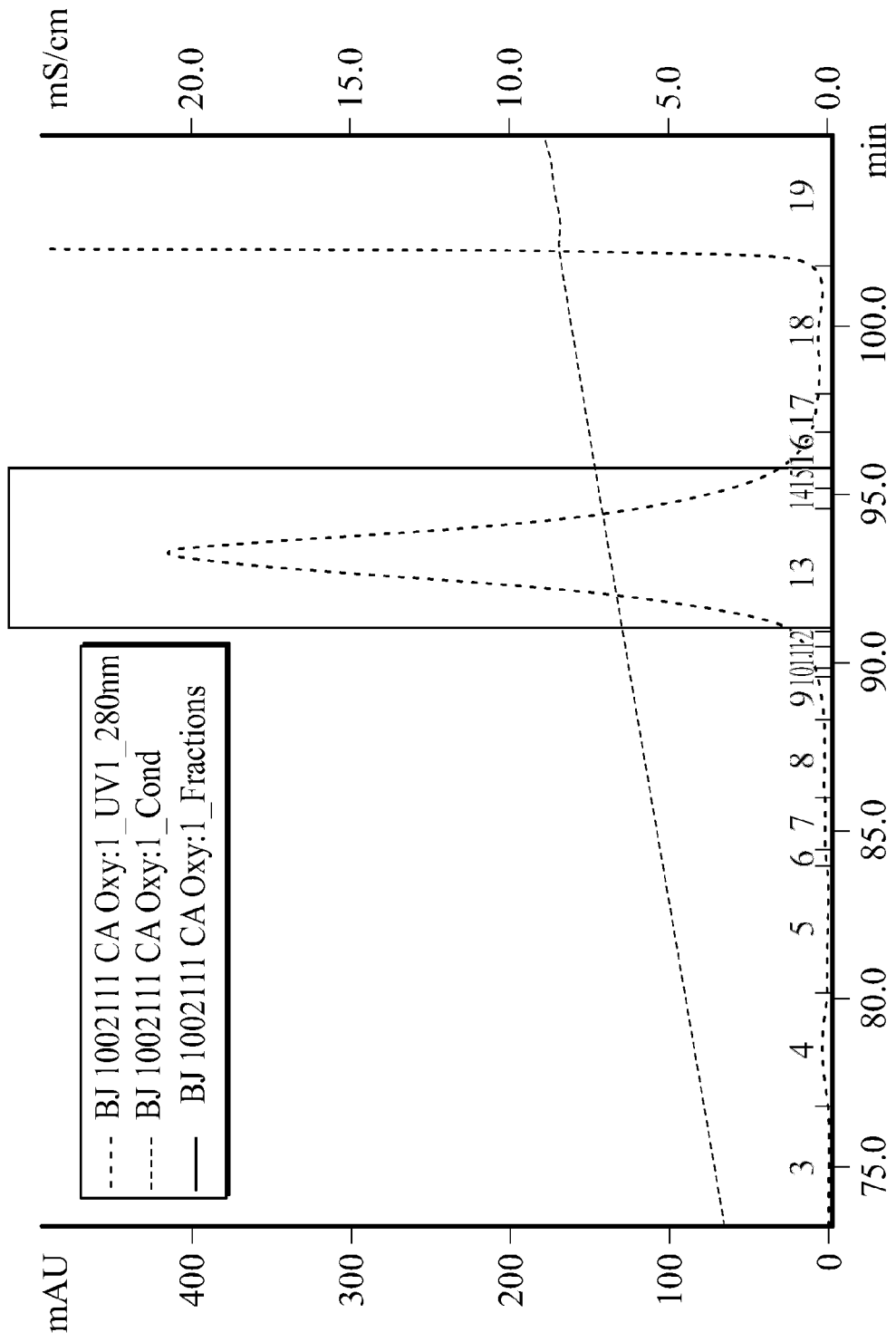
FIG. 4c is a graph showing the result of purifying conjugates including oxyntomodulin derivative (SEQ ID NO. 30) and immunoglobulin Fc through a SOURCE 15Q purification column.

Next, the purified mono-PEGylated oxyntomodulin derivative (SEQ ID NO. 30) and immunoglobulin Fc were reacted at a molar ratio of 1:10 with the protein concentration of 20 mg/ml at 4° C. for 16 hours. At this time, the reaction was conducted in 100 mM potassium phosphate buffer (pH 6.0) and 20 mM SCB was added thereto as a reducing agent. After completion of the reaction, the reaction mixture was applied to a SOURCE 15Q purification column to purify conjugates including oxyntomodulin derivative (SEQ ID NO. 30) and immunoglobulin Fc (column: SOURCE 15Q, flow rate: 2.0 ml/min, gradient: A 0→20% 100 min B (A: 20 mM Tris-HCl, pH 7.5, B: A+1M NaCl)) (FIG. 4c). FIG. 4c is a graph showing the result of purifying conjugates including oxyntomodulin derivative (SEQ ID NO. 30) and immunoglobulin Fc.

Figure 5A:
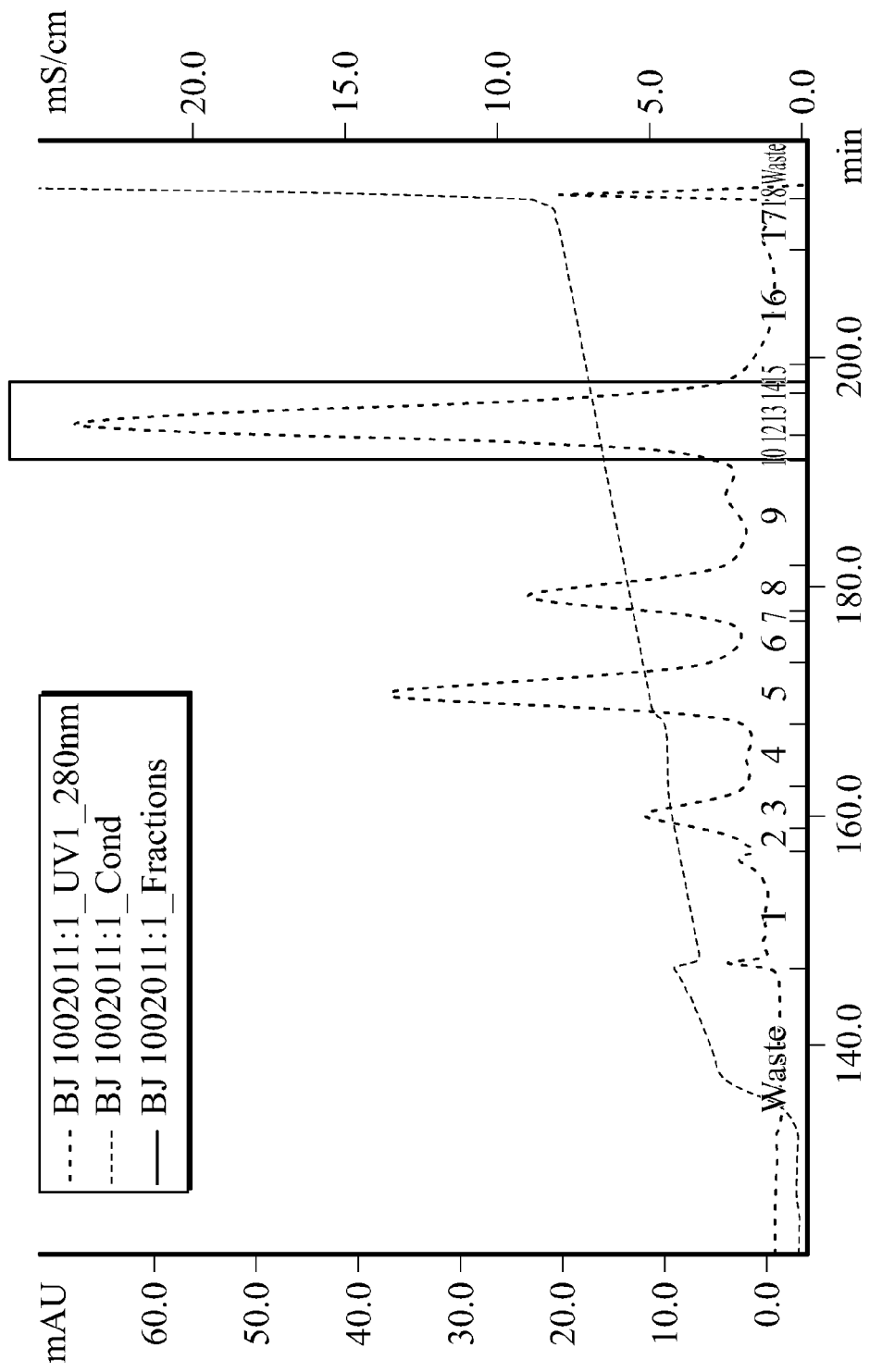
FIG. 5a is a graph showing the result of purifying a mono-PEGylated oxyntomodulin derivative (SEQ ID NO. 31) through a SOURCE S purification column.

Example 7: Preparation of Conjugates Including Oxyntomodulin Derivative (SEQ ID NO. 31) and Immunoglobulin Fc Firstly, for PEGylation of lysine residue at position 30 of the amino acid sequence of oxyntomodulin derivative (SEQ ID NO. 31) with 3.4 K PropionALD(2) PEG, the oxyntomodulin derivative (SEQ ID NO. 31) and 3.4 K PropionALD(2) PEG were reacted at a molar ratio of 1:15 with the protein concentration of 3 mg/ml at 4° C. for 4.5 hours. At this time, the reaction was conducted in a solvent mixture of 100 mM HEPES buffer (pH 7.5) and 45% isopropanol, and 20 mM SCB was added thereto as a reducing agent. After completion of the reaction, the reaction mixture was applied to a SOURCE Spurification column to purify the oxyntomodulin derivative having mono-pegylated lysine (Column: SOURCE S, flow rate: 2.0 ml/min, gradient: A 0→3% 1 min B→40% 222 min B (A: 20 mM Na-citrate, pH 3.0+45% ethanol, B: A+1M KCl)) (FIG. 5a). FIG. 5a is a graph showing the result of purifying a mono-PEGylated oxyntomodulin derivative (SEQ ID NO. 31) through a SOURCE S purification column.

Figure 5B:
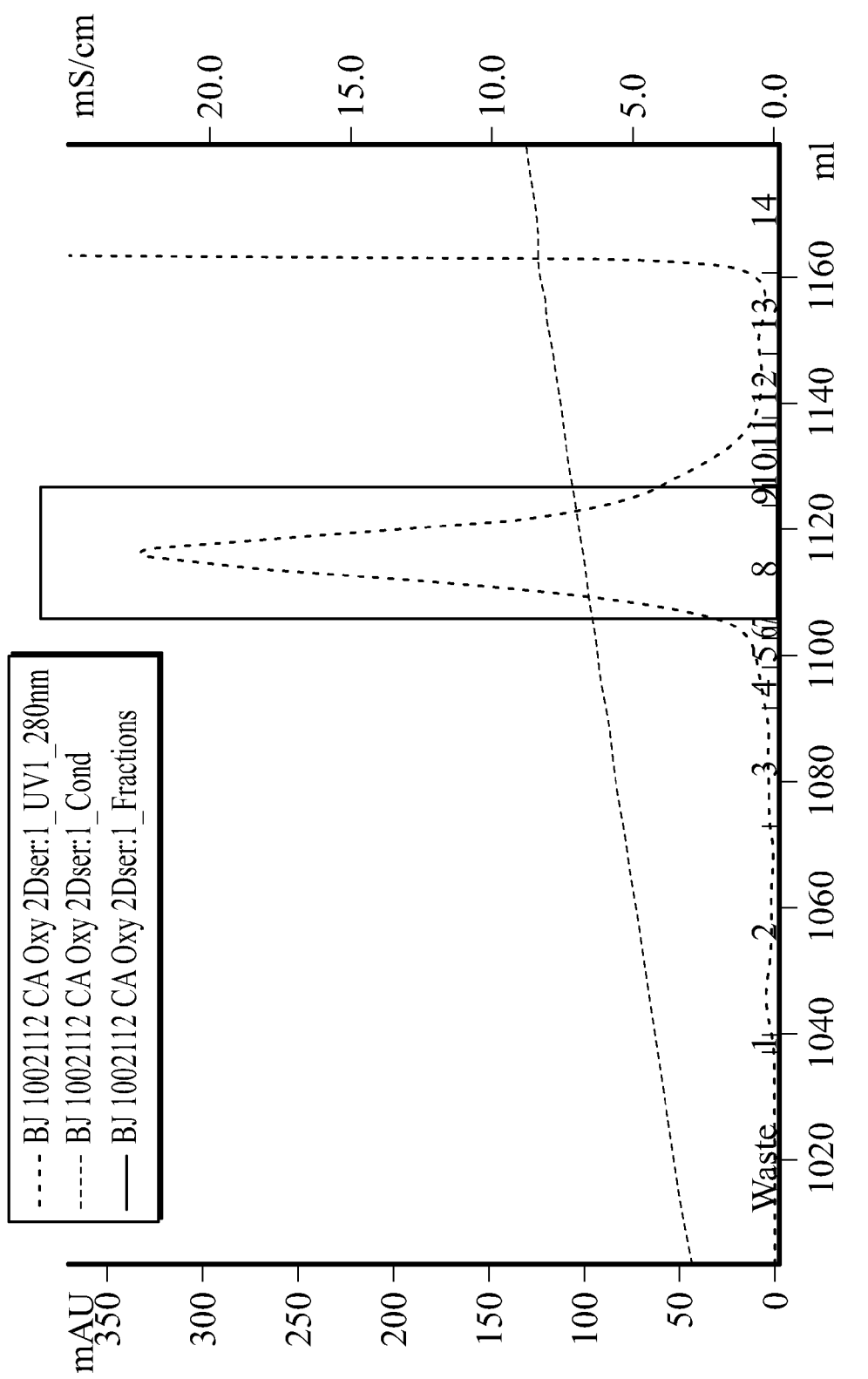
FIG. 5b is a graph showing the result of purifying conjugates including oxyntomodulin derivative (SEQ ID NO. 31) and immunoglobulin Fc through a SOURCE 15Q purification column.

Next, the purified mono-PEGylated oxyntomodulin derivative (SEQ ID NO. 31) and immunoglobulin Fc were reacted at a molar ratio of 1:10 with the protein concentration of 20 mg/ml at 4° C. for 16 hours. At this time, the reaction was conducted in 100 mM potassium phosphate buffer (pH 6.0) and 20 mM SCB was added thereto as a reducing agent. After completion of the reaction, the reaction mixture was applied to a SOURCE 15Q purification column to purify conjugates including oxyntomodulin derivative (SEQ ID NO. 31) and immunoglobulin Fc (column: SOURCE 15Q, flow rate: 2.0 ml/min, gradient: A 0→20% 100 min B (A: 20 mM Tris-HCl, pH 7.5, B: A+1M NaCl)) (FIG. 5b). FIG. 5b is a graph showing the result of purifying conjugates including oxyntomodulin derivative (SEQ ID NO. 31) and immunoglobulin Fc.

Figure 6A:
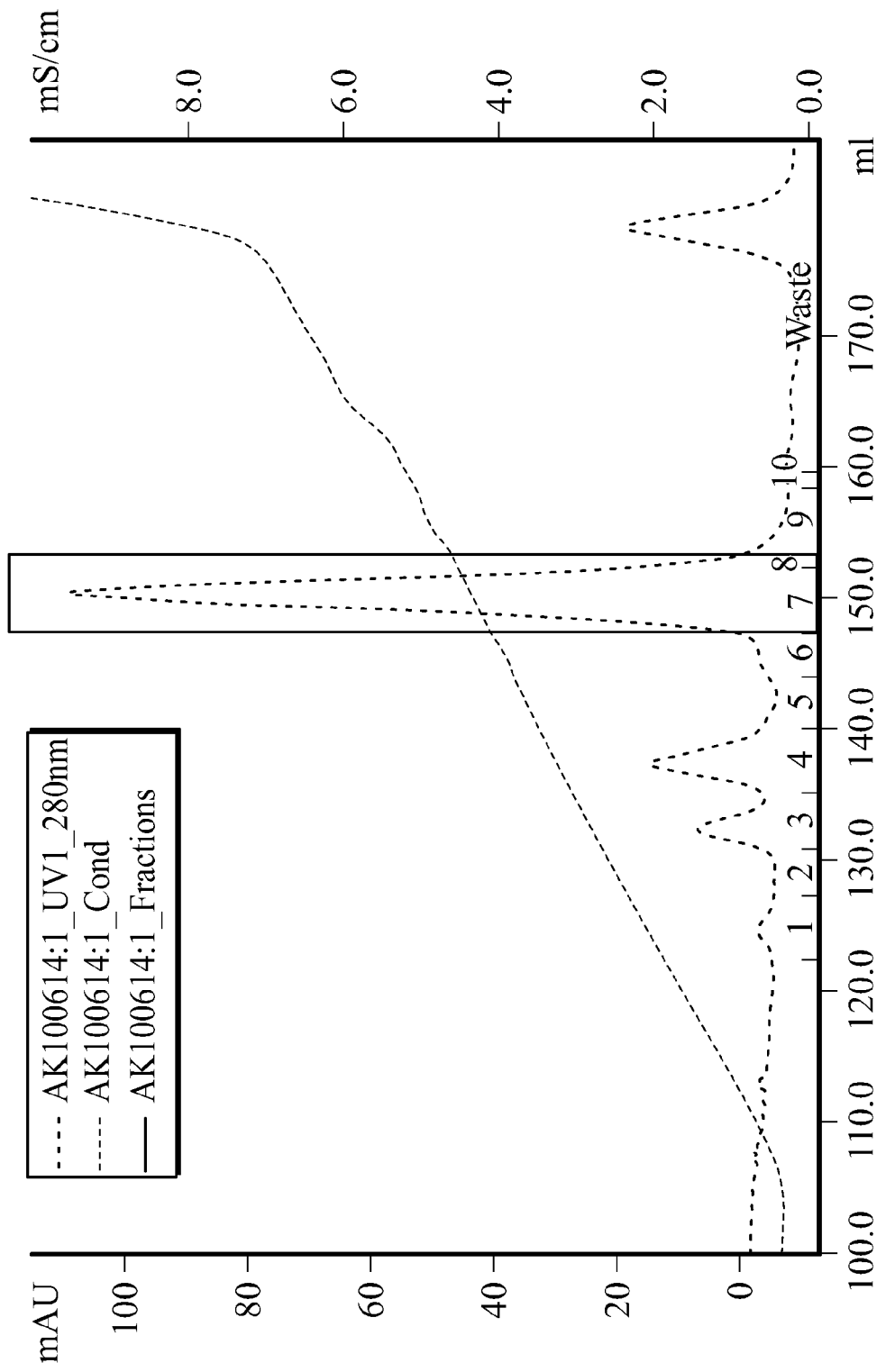
FIG. 6a is a graph showing the result of purifying a mono-PEGylated oxyntomodulin derivative (SEQ ID NO. 2) through a SOURCE S purification column.
Figure 6B:
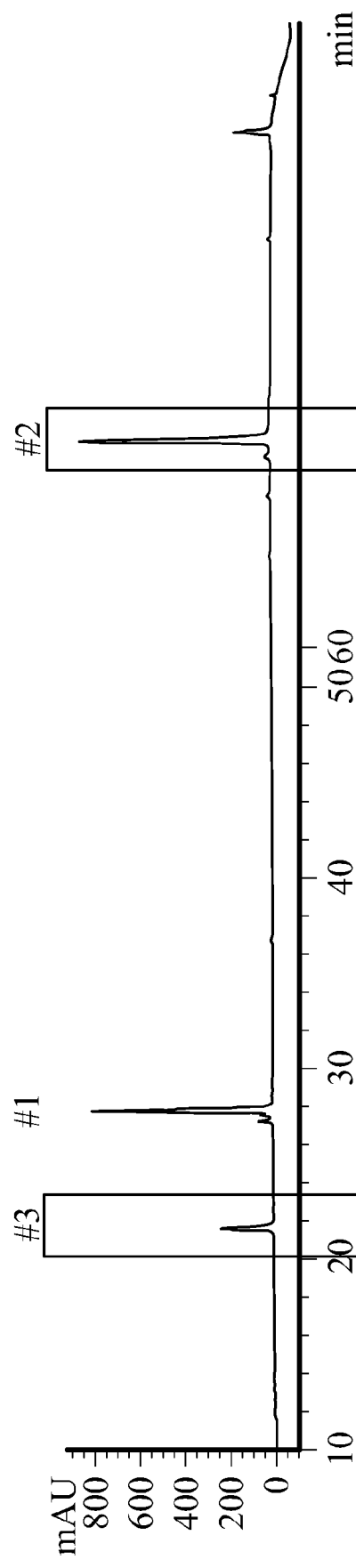
FIG. 6b is a graph showing the result of peptide mapping of purified mono-PEGylated oxyntomodulin derivative (SEQ ID NO. 2).
Figure 6B:
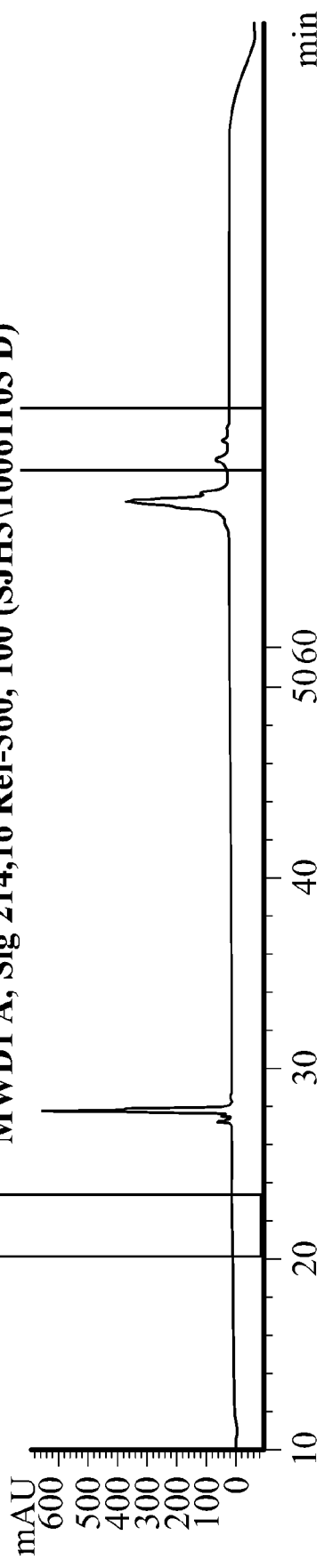

Example 8: Preparation of Conjugates Including Oxyntomodulin Derivative (SEQ ID NO. 2) and Immunoglobulin Fc Firstly, for PEGylation of lysine residue at position 30 of the amino acid sequence of oxyntomodulin derivative (SEQ ID NO. 2) with 3.4 K PropionALD(2) PEG, the oxyntomodulin derivative (SEQ ID NO. 2) and 3.4 K PropionALD(2) PEG were reacted at a molar ratio of 1:10 with the protein concentration of 3 mg/ml at 4° C. for 4 hours. At this time, the reaction was conducted in a solvent mixture of 100 mM HEPES buffer (pH 7.5) and 45% isopropanol, and 20 mM SCB was added thereto as a reducing agent. After completion of the reaction, the reaction mixture was applied to a SOURCE Spurification column to purify the oxyntomodulin derivative having mono-pegylated lysine (Column: SOURCE S, flow rate: 2.0 ml/min, gradient: A 0→3% 1 min B→40% 222 min B (A: 20 mM Na-citrate, pH 3.0+45% ethanol, B: A+1M KCl)) (FIG. 6a). FIG. 6a is a graph showing the result of purifying a mono-PEGylated oxyntomodulin derivative (SEQ ID NO. 2) through a SOURCE S purification column. Mono-PEGylation of the eluted peaks was examined by SDS-PAGE, and lysine selectivity was examined by peptide mapping using Asp-N protease (FIG. 6b). FIG. 6b is a graph showing the result of peptide mapping of purified mono-PEGylated oxyntomodulin derivative (SEQ ID NO. 2).

Figure 6C:
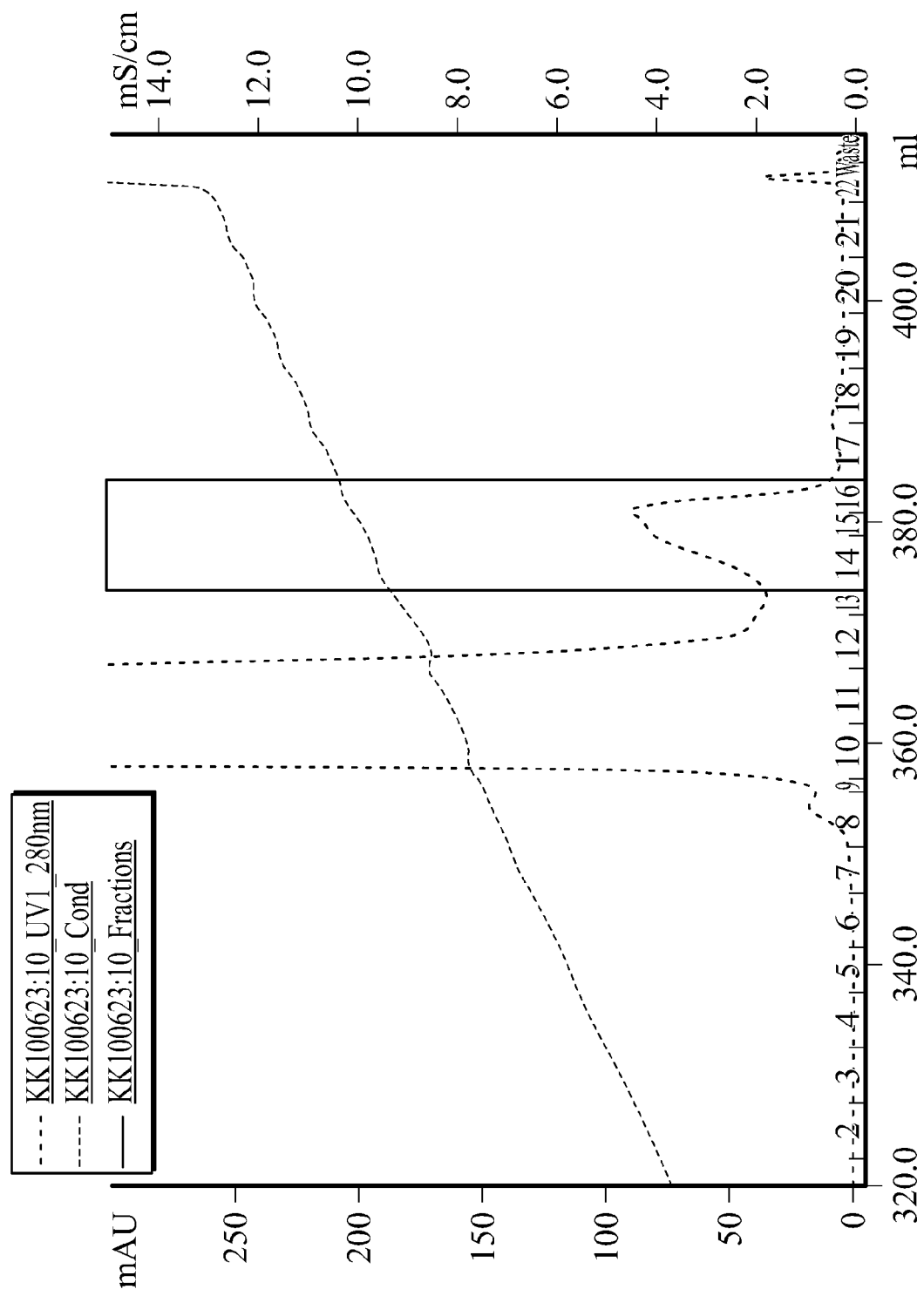
FIG. 6c is a graph showing the result of purifying conjugates including oxyntomodulin derivative (SEQ ID NO. 2) and immunoglobulin Fc through a SOURCE 15Q purification column.
Figure 6D:
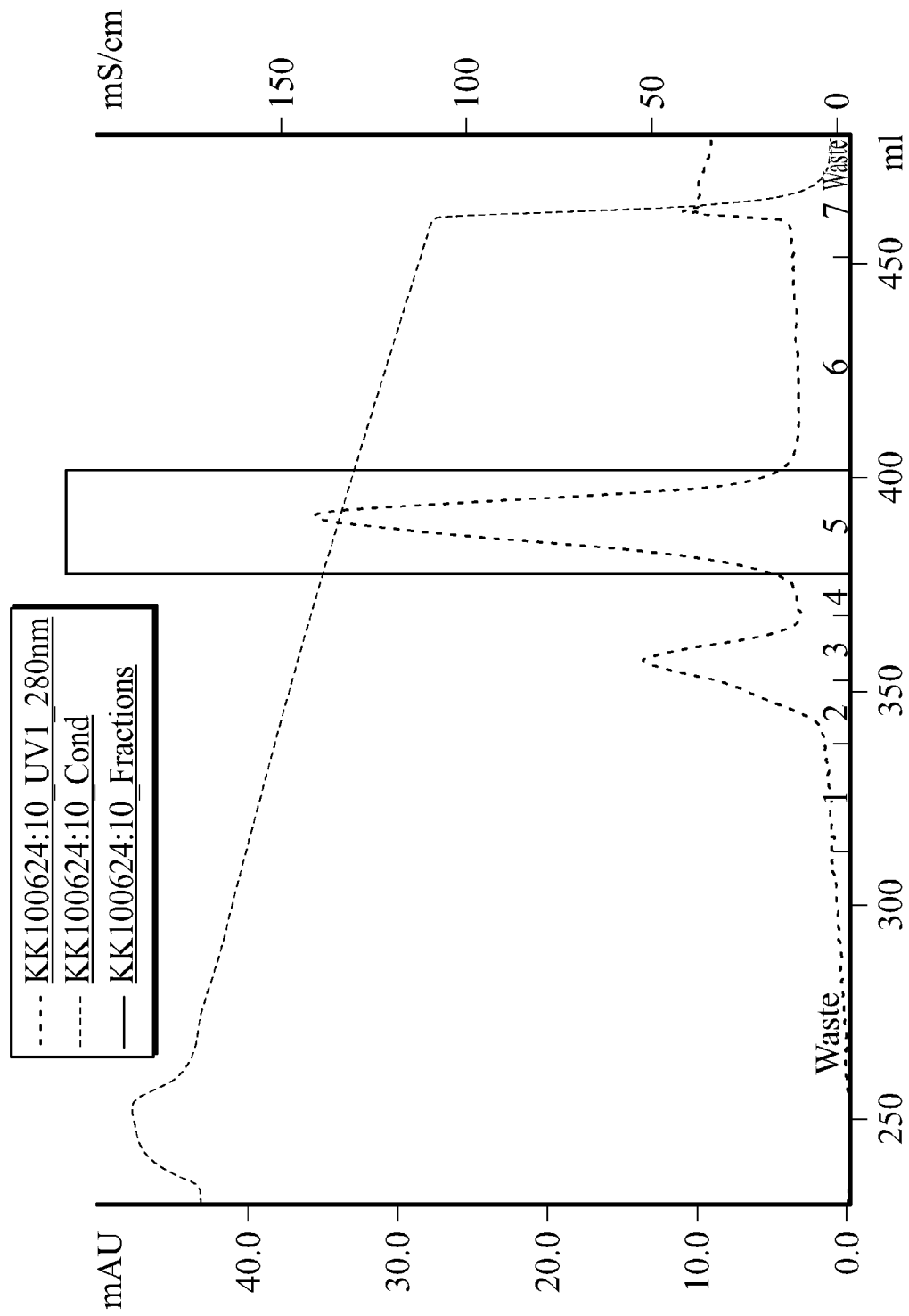
FIG. 6d is a graph showing the result of purifying conjugates including oxyntomodulin derivative (SEQ ID NO. 2) and immunoglobulin Fc through a Source ISO purification column.

Next, the purified mono-PEGylated oxyntomodulin derivative (SEQ ID NO. 2) and immunoglobulin Fc were reacted at a molar ratio of 1:8 with the protein concentration of 20 mg/ml at 4° C. for 16 hours. At this time, the reaction was conducted in 100 mM potassium phosphate buffer (pH 6.0) and 20 mM SCB was added thereto as a reducing agent. After completion of the reaction, the reaction mixture was applied to a SOURCE 15Q purification column (Column: SOURCE 15Q, flow rate: 2.0 ml/min, gradient: A 0→4% 1 min B→20% 80 min B (A: 20 mM Tris-HCl, pH 7.5, B: A+1M NaCl)) (FIG. 6c) and a Source ISO purification column (Column: SOURCE ISO (XK16, Amersham Biosciences), flow rate: 2.0 ml/min, gradient: A 0→100% 100 min B, (A: 20 mM Tris-HCl, pH 7.5, B: A+1.3M AS))(FIG. 6d) to purify conjugates including oxyntomodulin derivative (SEQ ID NO. 2) and immunoglobulin Fc. FIG. 6c is a graph showing the result of purifying conjugates including oxyntomodulin derivative (SEQ ID NO. 2) and immunoglobulin Fc through a Source ISO purification column, and FIG. 6d is a graph showing the result of purifying conjugates including oxyntomodulin derivative (SEQ ID NO. 2) and immunoglobulin Fc through a Source ISO purification column.

Figure 7A:
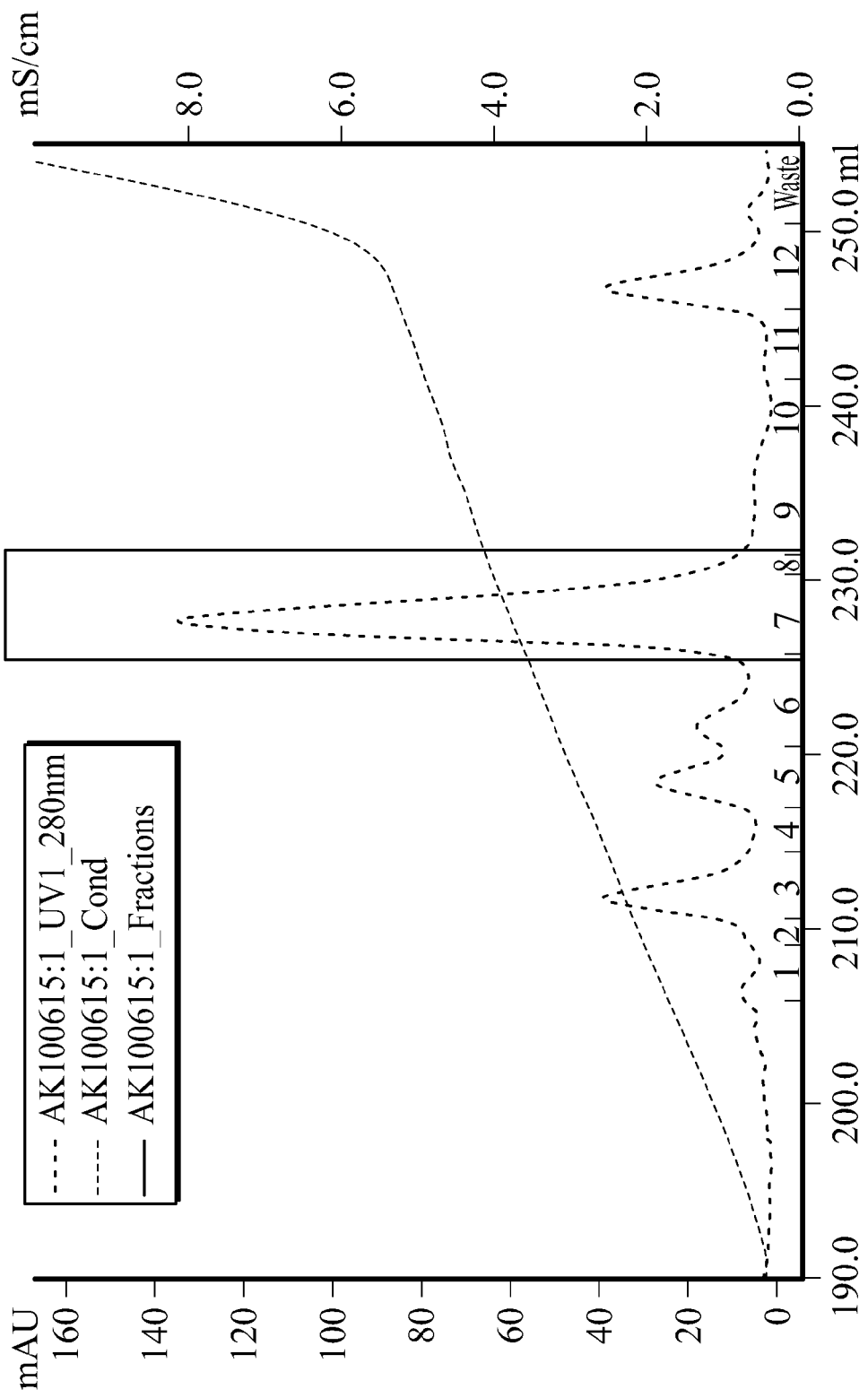
FIG. 7a is a graph showing the result of purifying a mono-PEGylated oxyntomodulin derivative (SEQ ID NO. 3) through a SOURCE S purification column.
Figure 7B:
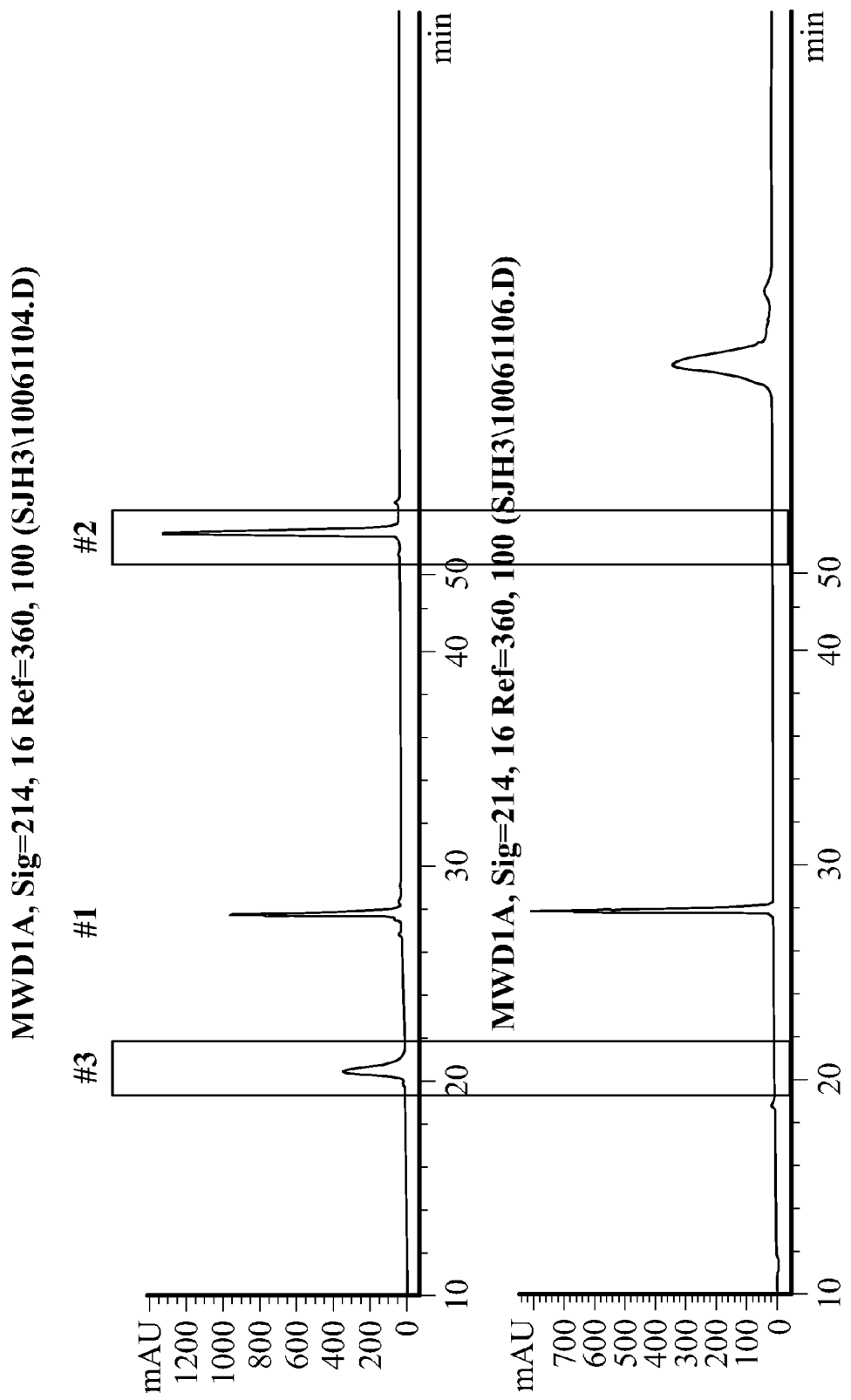
FIG. 7b is a graph showing the result of peptide mapping of purified mono-PEGylated oxyntomodulin derivative (SEQ ID NO. 3).

Example 9: Preparation of Conjugates Including Oxyntomodulin Derivative (SEQ ID NO. 3) and Immunoglobulin Fc Firstly, for PEGylation of lysine residue at position 27 of the amino acid sequence of oxyntomodulin derivative (SEQ ID NO. 3) with 3.4 K PropionALD(2) PEG, the oxyntomodulin derivative (SEQ ID NO. 3) and 3.4 K PropionALD (2) PEG were reacted at a molar ratio of 1:10 with the protein concentration of 3 mg/ml at 4° C. for 4 hours. At this time, the reaction was conducted in a solvent mixture of 100 mM HEPES buffer (pH 7.5) and 45% isopropanol, and 20 mM SCB was added thereto as a reducing agent. After completion of the reaction, the reaction mixture was applied to a SOURCE Spurification column to purify the oxyntomodulin derivative having mono-pegylated lysine (Column: SOURCE S, flow rate: 2.0 ml/min, gradient: A 0→3% 1 min B→40% 222 min B (A: 20 mM Na-citrate, pH 3.0+45% ethanol, B: A+1M KCl)) (FIG. 7a). FIG. 7a is a graph showing the result of purifying a mono-PEGylated oxyntomodulin derivative (SEQ ID NO. 3) through a SOURCE S purification column. Mono-PEGylation of the eluted peaks was examined by SDS-PAGE, and lysine selectivity was examined by peptide mapping using Asp-N protease (FIG. 7b). FIG. 7b is a graph showing the result of peptide mapping of purified mono-PEGylated oxyntomodulin derivative (SEQ ID NO. 3).

Figure 7C:
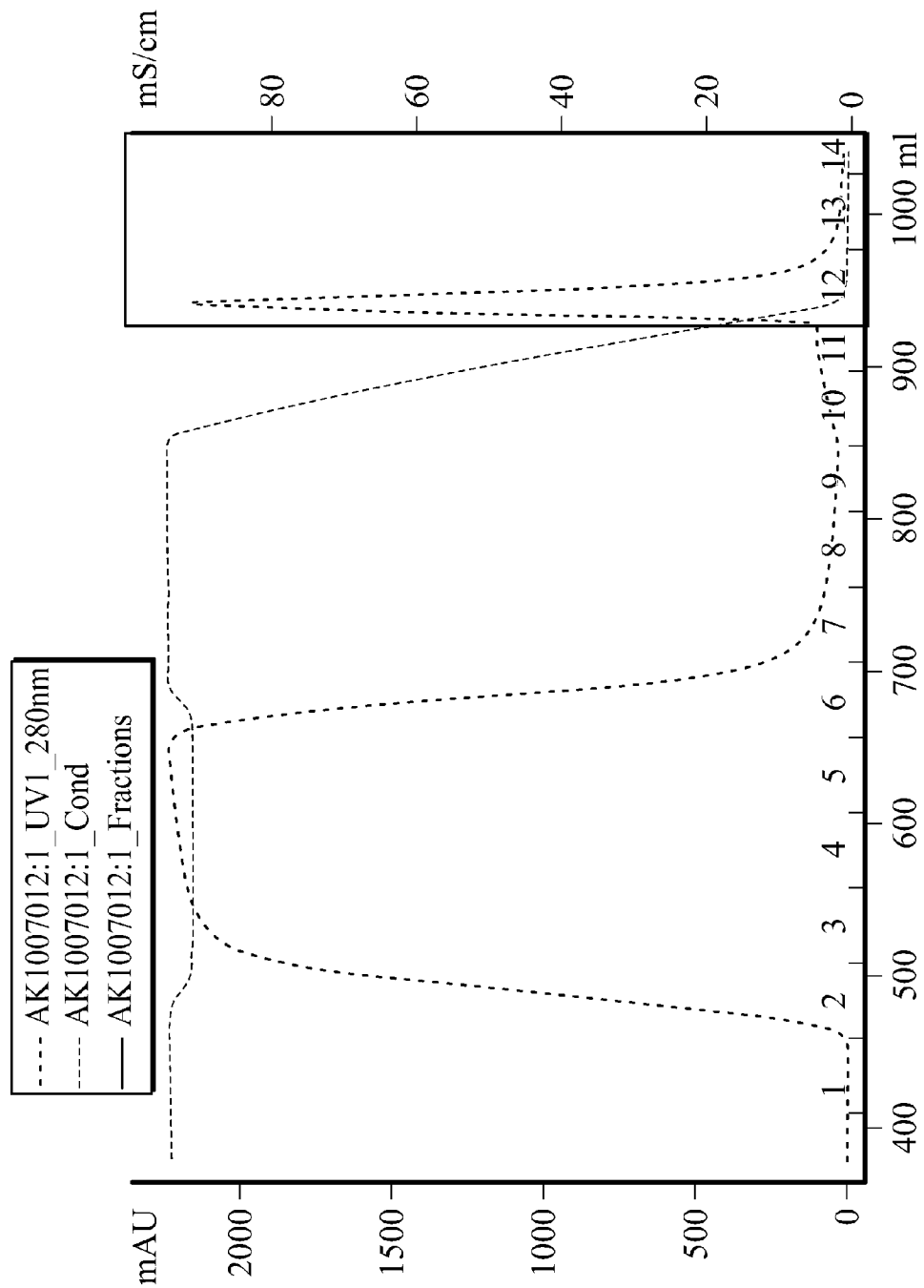
FIG. 7c is a graph showing the result of purifying conjugates including oxyntomodulin derivative (SEQ ID NO. 3) and immunoglobulin Fc through a Butyl FF purification column.
Figure 7D:
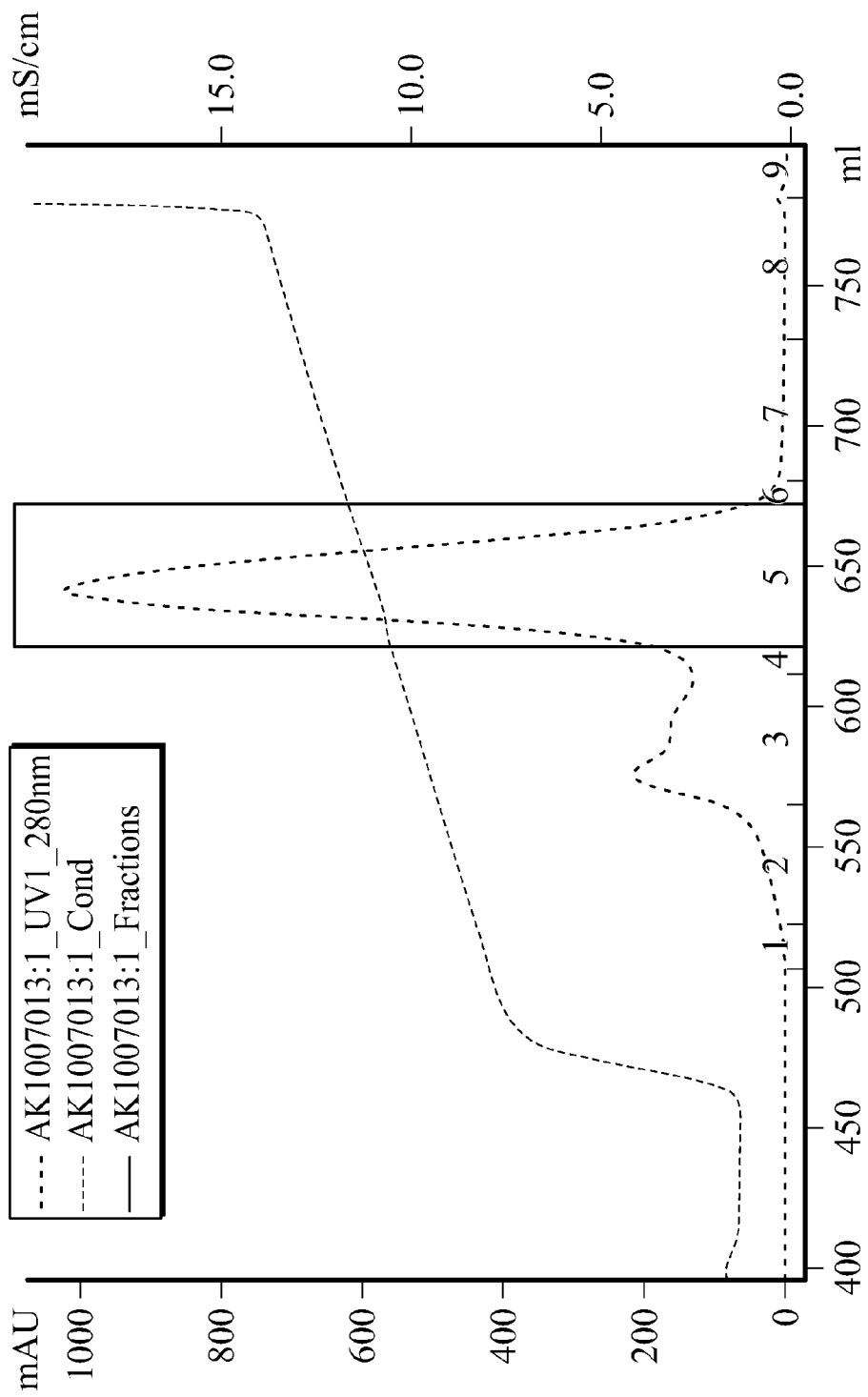
FIG. 7d is a graph showing the result of purifying conjugates including oxyntomodulin derivative (SEQ ID NO. 3) and immunoglobulin Fc through a Source 15Q purification column.

Next, the purified mono-PEGylated oxyntomodulin derivative (SEQ ID NO. 3) and immunoglobulin Fc were reacted at a molar ratio of 1:8 with the protein concentration of 20 mg/ml at 4° C. for 16 hours. At this time, the reaction was conducted in 100 mM potassium phosphate buffer (pH 6.0) and 20 mM SCB was added thereto as a reducing agent. After completion of the reaction, the reaction mixture was applied to a Butyl FF purification column (Column: Butyl FF(XK16, Amersham Biosciences), flow rate: 2.0 ml/min, gradient: B 0→100% 5 min A (A: 20 mM Tris-HCl, pH 7.5, B: A+1.5M NaCl)) (FIG. 7c) and a SOURCE 15Q purification column (Column: SOURCE 15Q, flow rate: 2.0 ml/min, gradient: A 0→4% 1 min B→20% 80 min B (A: 20 mM Tris-HCl, pH 7.5, B: A+1M NaCl)) (FIG. 7d) to purify conjugates including oxyntomodulin derivative (SEQ ID NO. 3) and immunoglobulin Fc. FIG. 7c is a graph showing the result of purifying conjugates including oxyntomodulin derivative (SEQ ID NO. 3) and immunoglobulin Fc through a Butyl FF purification column, and FIG. 7d is a graph showing the result of purifying conjugates including oxyntomodulin derivative (SEQ ID NO. 3) and immunoglobulin Fc through a SOURCE 15Q purification column.

Figure 8A:
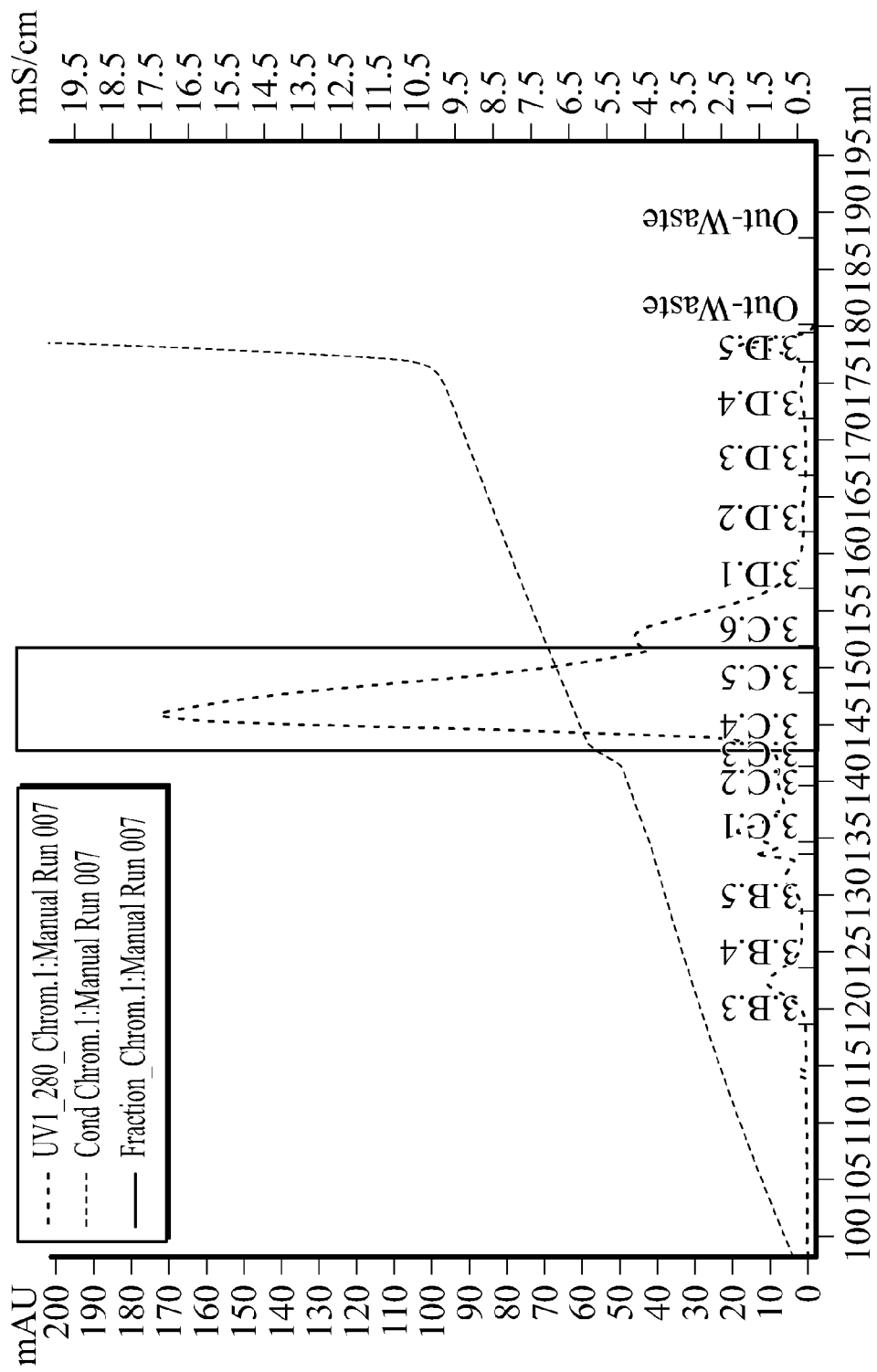
FIG. 8a is a graph showing the result of purifying a mono-PEGylated oxyntomodulin derivative (SEQ ID NO. 23) through a SOURCE S purification column.

Example 10: Preparation of Conjugates Including Oxyntomodulin Derivative (SEQ ID NO. 23) and Immunoglobulin Fc Firstly, for PEGylation of cysteine residue at position 24 of the amino acid sequence of oxyntomodulin derivative (SEQ ID NO. 23) with MAL-10K-ALD PEG (NOF., Japan), the oxyntomodulin derivative (SEQ ID NO. 23) and MAL-10K-ALD PEG were reacted at a molar ratio of 1:3 with the protein concentration of 3 mg/ml at room temperature for 3 hours. At this time, the reaction was conducted in 50 mM Tris buffer (pH 8.0) and 45% isopropanol, and 1M guanidine was added thereto. After completion of the reaction, the reaction mixture was applied to a SOURCE Spurification column to purify the oxyntomodulin derivative having mono-pegylated cysteine (column: SOURCE S, flow rate: 2.0 ml/min, gradient: A 0→100% 50 min B (A: 20 mM Na-citrate, pH 3.0+45% ethanol, B: A+1M KCl)) (FIG. 8a). FIG. 8a is a graph showing the result of purifying a mono-PEGylated oxyntomodulin derivative (SEQ ID NO. 23) through a SOURCE S purification column.

Figure 8B:
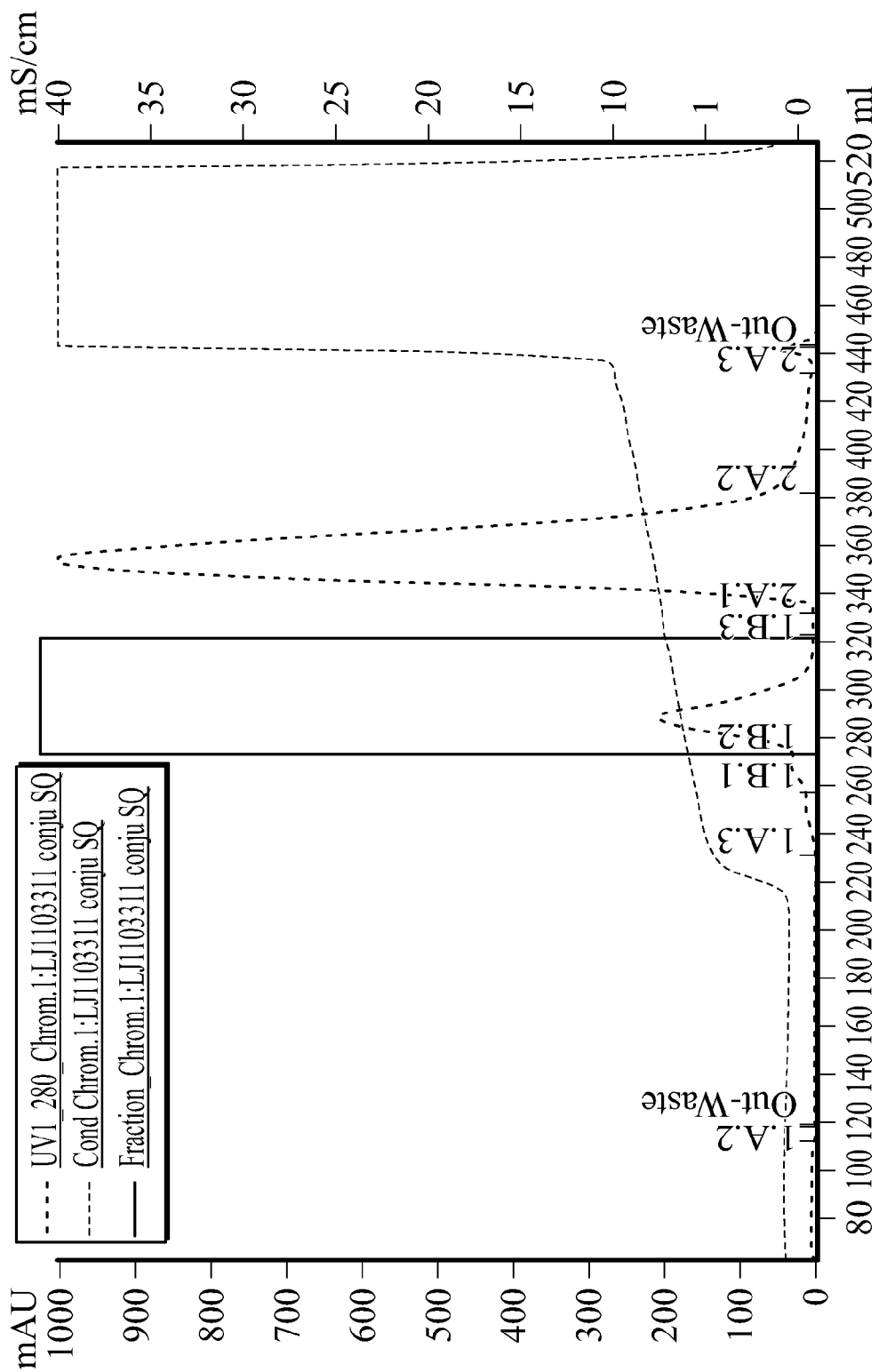
FIG. 8b is a graph showing the result of purifying conjugates including oxyntomodulin derivative (SEQ ID NO. 23) and immunoglobulin Fc through a Source 15Q purification column.
Figure 8C:
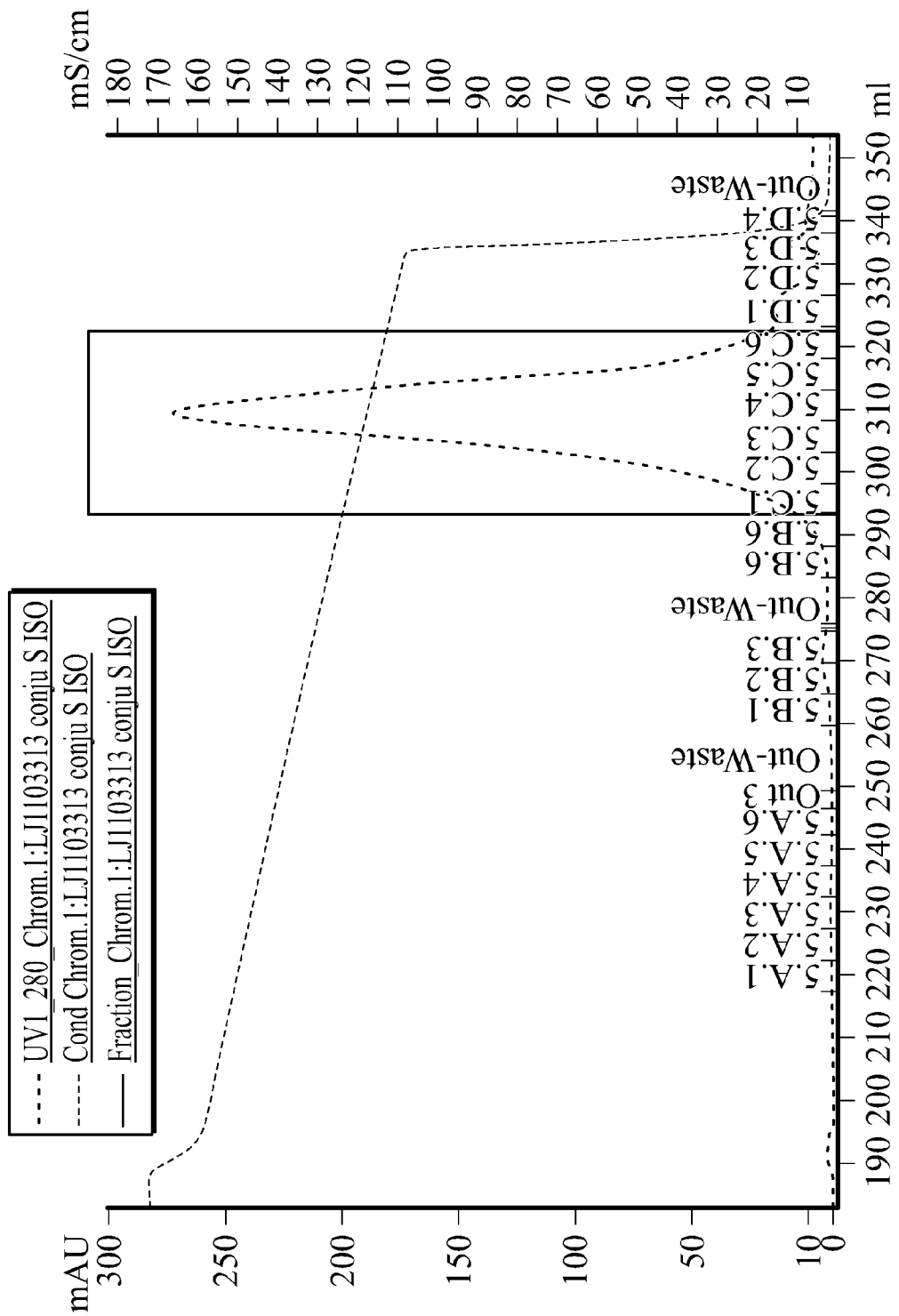
FIG. 8c is a graph showing the result of purifying conjugates including oxyntomodulin derivative (SEQ ID NO. 23) and immunoglobulin Fc through a SOURCE ISO purification column.

Next, the purified mono-PEGylated oxyntomodulin derivative (SEQ ID NO. 23) and immunoglobulin Fc were reacted at a molar ratio of 1:5 with the protein concentration of 20 mg/ml at 4° C. for 16 hours. At this time, the reaction was conducted in 100 mM potassium phosphate buffer (pH 6.0) and 20 mM SCB was added thereto as a reducing agent. After completion of the reaction, the reaction mixture was applied to a SOURCE 15Q purification column (column: SOURCE 15Q, flow rate: 2.0 ml/min, gradient: A 0→4% 1 min B→20% 80 min B (A: 20 mM Tris-HCl, pH 7.5, B: A+1M NaCl)) (FIG. 8b) and a Source ISO purification column (column: SOURCE ISO, flow rate: 2.0 ml/min, gradient: B 0→100% 100 min A, (A: 20 mM Tris-HCl, pH 7.5, B: A+1.1M AS)) (FIG. 8c) to purify conjugates including oxyntomodulin derivative (SEQ ID NO. 23) and immunoglobulin Fc. FIG. 8b is a graph showing the result of purifying conjugates including oxyntomodulin derivative (SEQ ID NO. 23) and immunoglobulin Fc through a SOURCE 15Q purification column, and FIG. 8c is a graph showing the result of purifying conjugates including oxyntomodulin derivative (SEQ ID NO. 23) and immunoglobulin Fc through a Source ISO purification column.

Figure 9A:
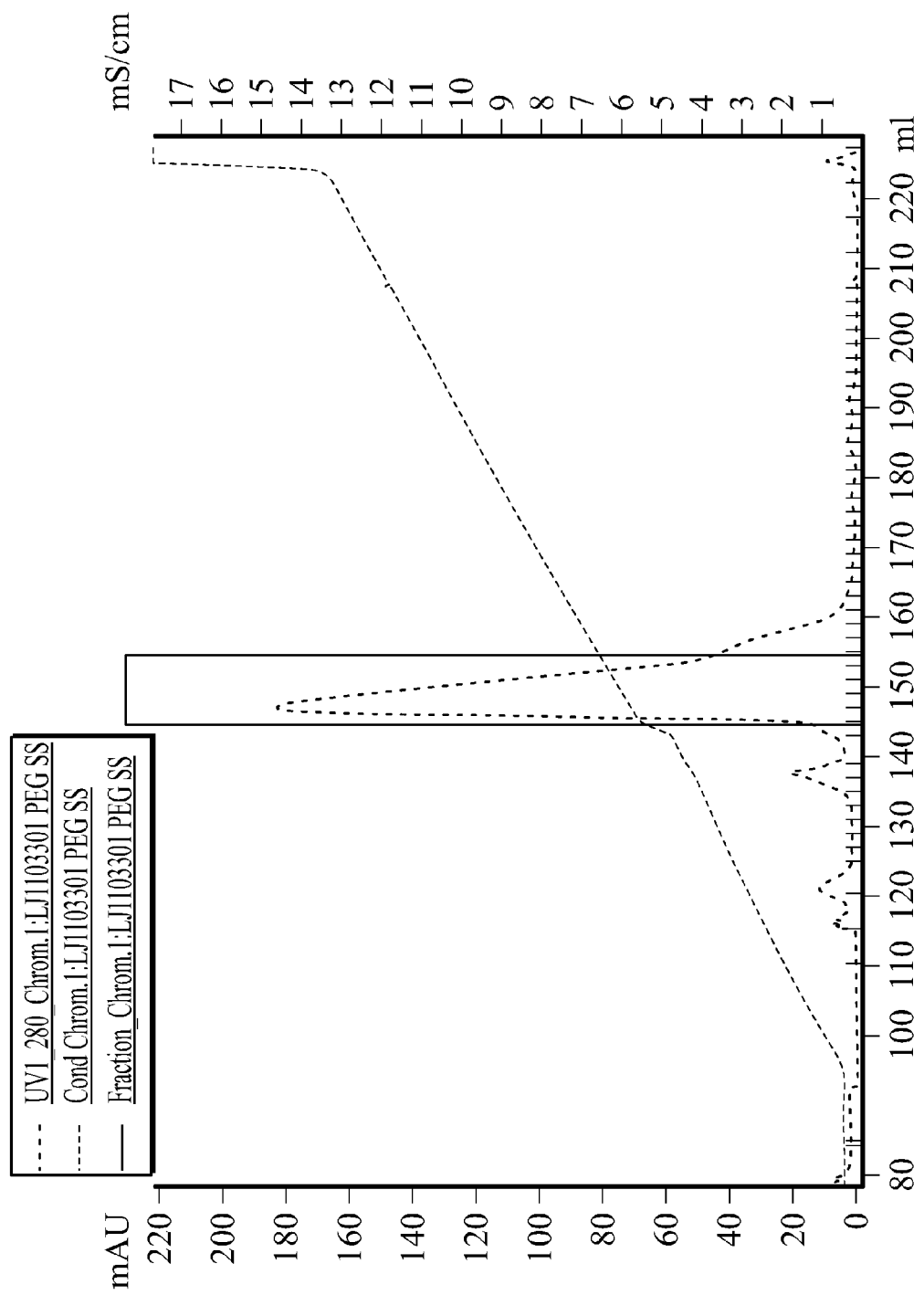
FIG. 9a is a graph showing the result of purifying a mono-PEGylated oxyntomodulin derivative (SEQ ID NO. 24) through a SOURCE S purification column.

Example 11: Preparation of Conjugates Including Oxyntomodulin Derivative (SEQ ID NO. 24) and Immunoglobulin Fc Firstly, for PEGylation of cysteine residue at position 30 of the amino acid sequence of oxyntomodulin derivative (SEQ ID NO. 24) with MAL-10K-ALD PEG, the oxyntomodulin derivative (SEQ ID NO. 24) and MAL-10K-ALD PEG were reacted at a molar ratio of 1:3 with the protein concentration of 3 mg/ml at room temperature for 3 hours. At this time, the reaction was conducted in 50 mM Tris buffer (pH 8.0) and 45% isopropanol, and 1M guanidine was added thereto. After completion of the reaction, the reaction mixture was applied to a SOURCE Spurification column to purify the oxyntomodulin derivative having mono-pegylated cysteine (column: SOURCE S, flow rate: 2.0 ml/min, gradient: A 0→100% 50 min B (A: 20 mM Na-citrate, pH 3.0+45% ethanol, B: A+1M KCl)) (FIG. 9a). FIG. 9a is a graph showing the result of purifying a mono-PEGylated oxyntomodulin derivative (SEQ ID NO. 24) through a SOURCE S purification column.

Figure 9B:
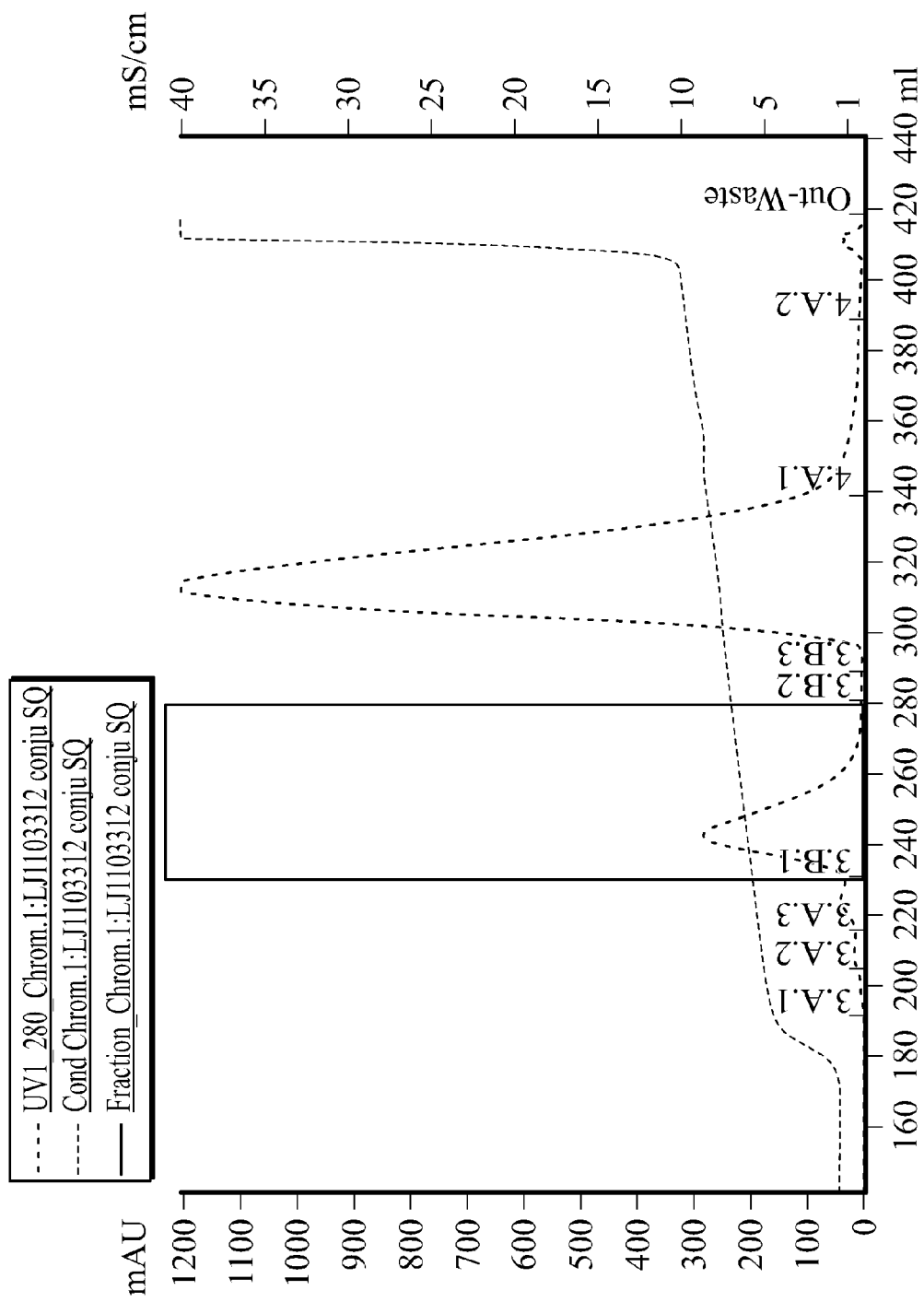
FIG. 9b is a graph showing the result of purifying conjugates including oxyntomodulin derivative (SEQ ID NO. 24) and immunoglobulin Fc through a Source 15Q purification column.
Figure 9C:
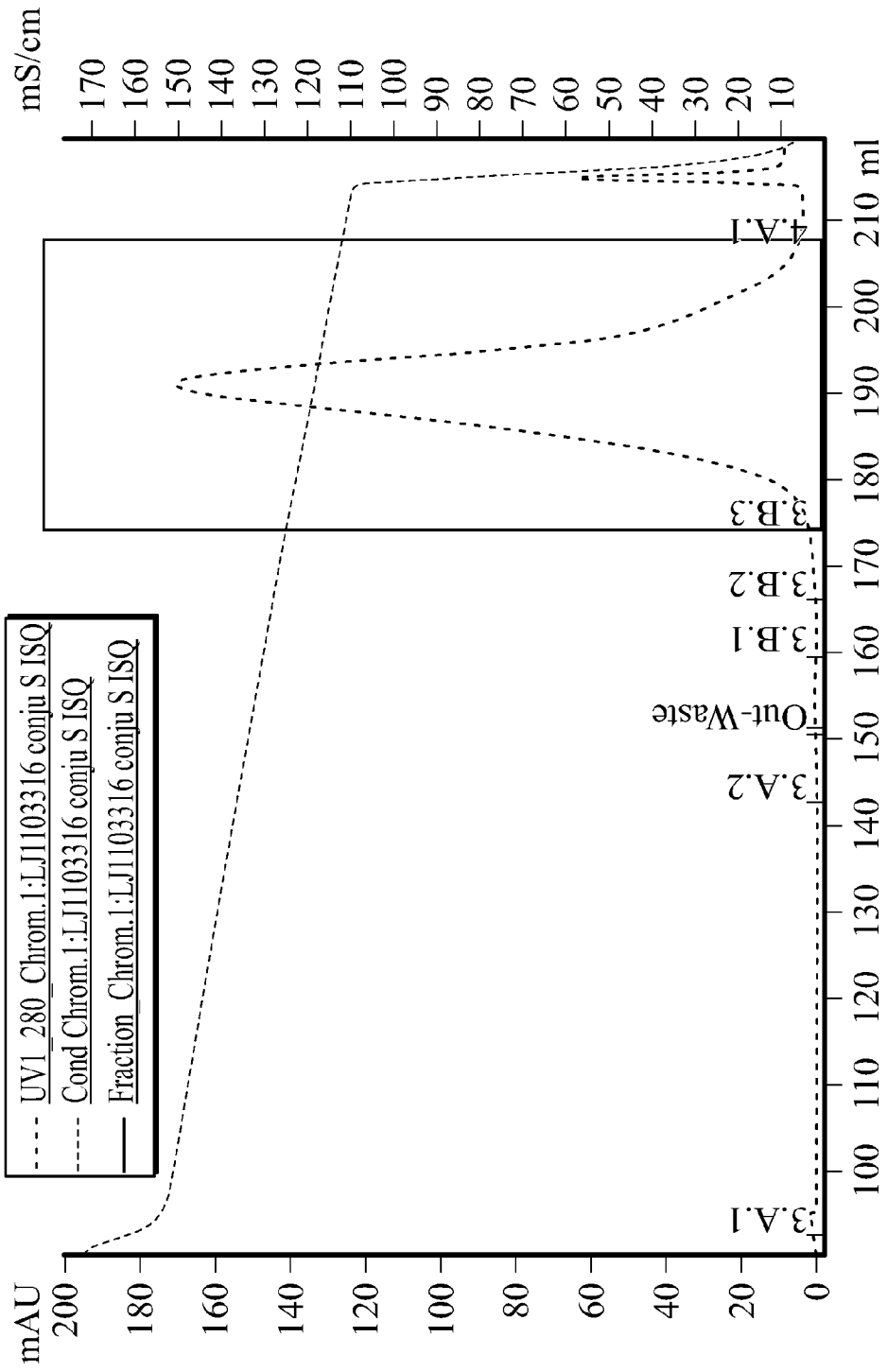
FIG. 9c is a graph showing the result of purifying conjugates including oxyntomodulin derivative (SEQ ID NO. 24) and immunoglobulin Fc through a SOURCE ISO purification column.

Next, the purified mono-PEGylated oxyntomodulin derivative (SEQ ID NO. 24) and immunoglobulin Fc were reacted at a molar ratio of 1:5 with the protein concentration of 20 mg/ml at 4° C. for 16 hours. At this time, the reaction was conducted in 100 mM potassium phosphate buffer (pH 6.0) and 20 mM SCB was added thereto as a reducing agent. After completion of the reaction, the reaction mixture was applied to a SOURCE 15Q purification column (column: SOURCE 15Q, flow rate: 2.0 ml/min, gradient: A 0→4% 1 min B→20% 80 min B (A: 20 mM Tris-HCl, pH 7.5, B: A+1M NaCl)) (FIG. 9b) and a Source ISO purification column (column: SOURCE ISO, flow rate: 2.0 ml/min, gradient: B 0→100% 100 min A, (A: 20 mM Tris-HCl, pH 7.5, B: A+1.1M AS)) (FIG. 9c) to purify conjugates including oxyntomodulin derivative (SEQ ID NO. 24) and immunoglobulin Fc. FIG. 9b is a graph showing the result of purifying conjugates including oxyntomodulin derivative (SEQ ID NO. 24) and immunoglobulin Fc through a SOURCE 15Q purification column, and FIG. 9c is a graph showing the result of purifying conjugates including oxyntomodulin derivative (SEQ ID NO. 24) and immunoglobulin Fc through a Source ISO purification column.

Figure 10A:
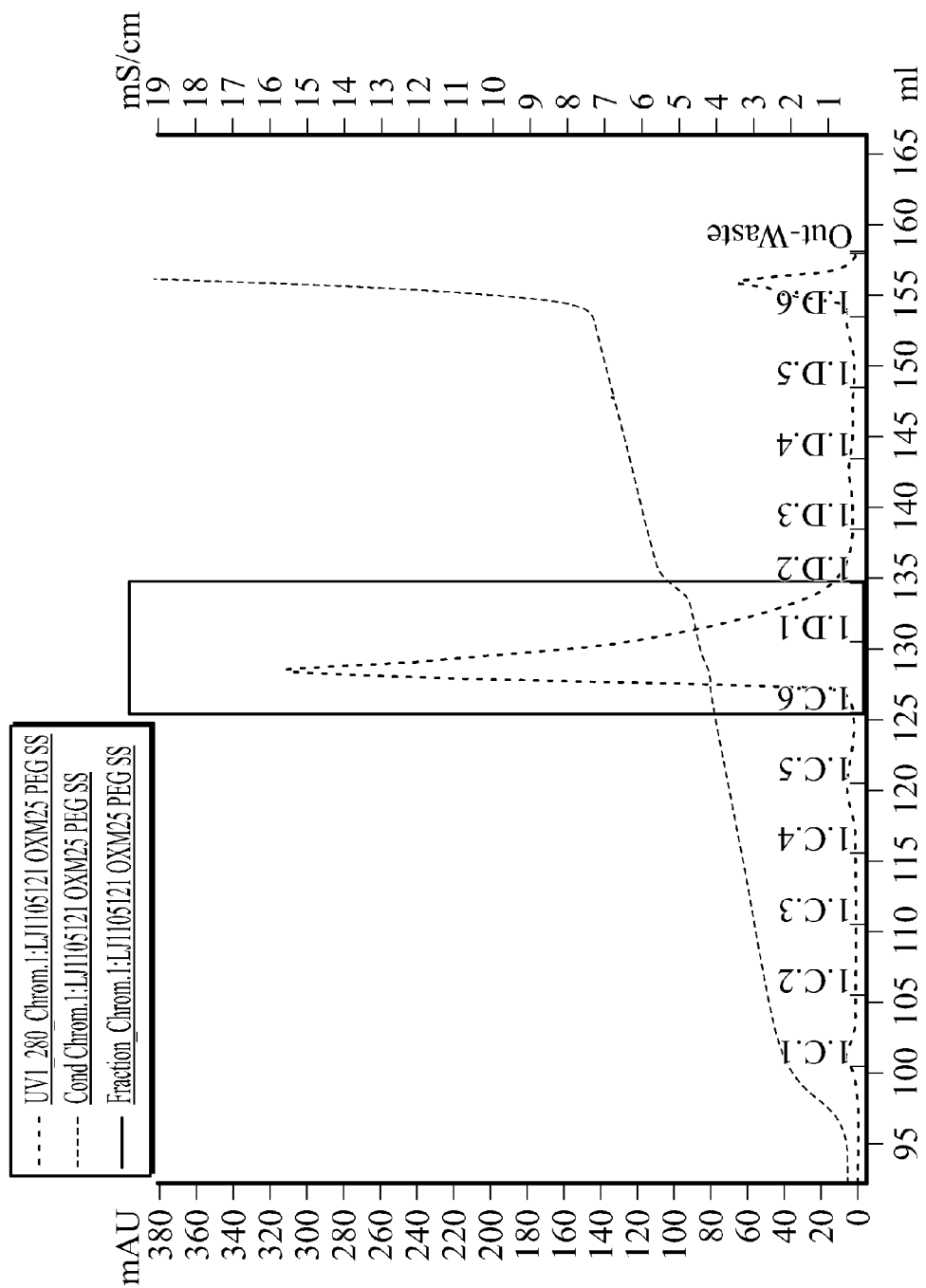
FIG. 10a is a graph showing the result of purifying a mono-PEGylated oxyntomodulin derivative (SEQ ID NO. 25) through a SOURCE S purification column.

Example 12: Preparation of Conjugates Including Oxyntomodulin Derivative (SEQ ID NO. 25) and Immunoglobulin Fc Firstly, for PEGylation of cysteine residue at position 30 of the amino acid sequence of oxyntomodulin derivative (SEQ ID NO. 25) with MAL-10K-ALD PEG, the oxyntomodulin derivative (SEQ ID NO. 25) and MAL-10K-ALD PEG were reacted at a molar ratio of 1:3 with the protein concentration of 3 mg/ml at room temperature for 3 hours. At this time, the reaction was conducted in 50 mM Tris buffer (pH 8.0) and 1M guanidine was added thereto. After completion of the reaction, the reaction mixture was applied to a SOURCE Spurification column to purify the oxyntomodulin derivative having mono-pegylated cysteine (column: SOURCE S, flow rate: 2.0 ml/min, gradient: A 0→100% 50 min B (A: 20 mM Na-citrate, pH 3.0+45% ethanol, B: A+1M KCl)) (FIG. 10a). FIG. 10a is a graph showing the result of purifying a mono-PEGylated oxyntomodulin derivative (SEQ ID NO. 25) through a SOURCE S purification column.

Figure 10B:
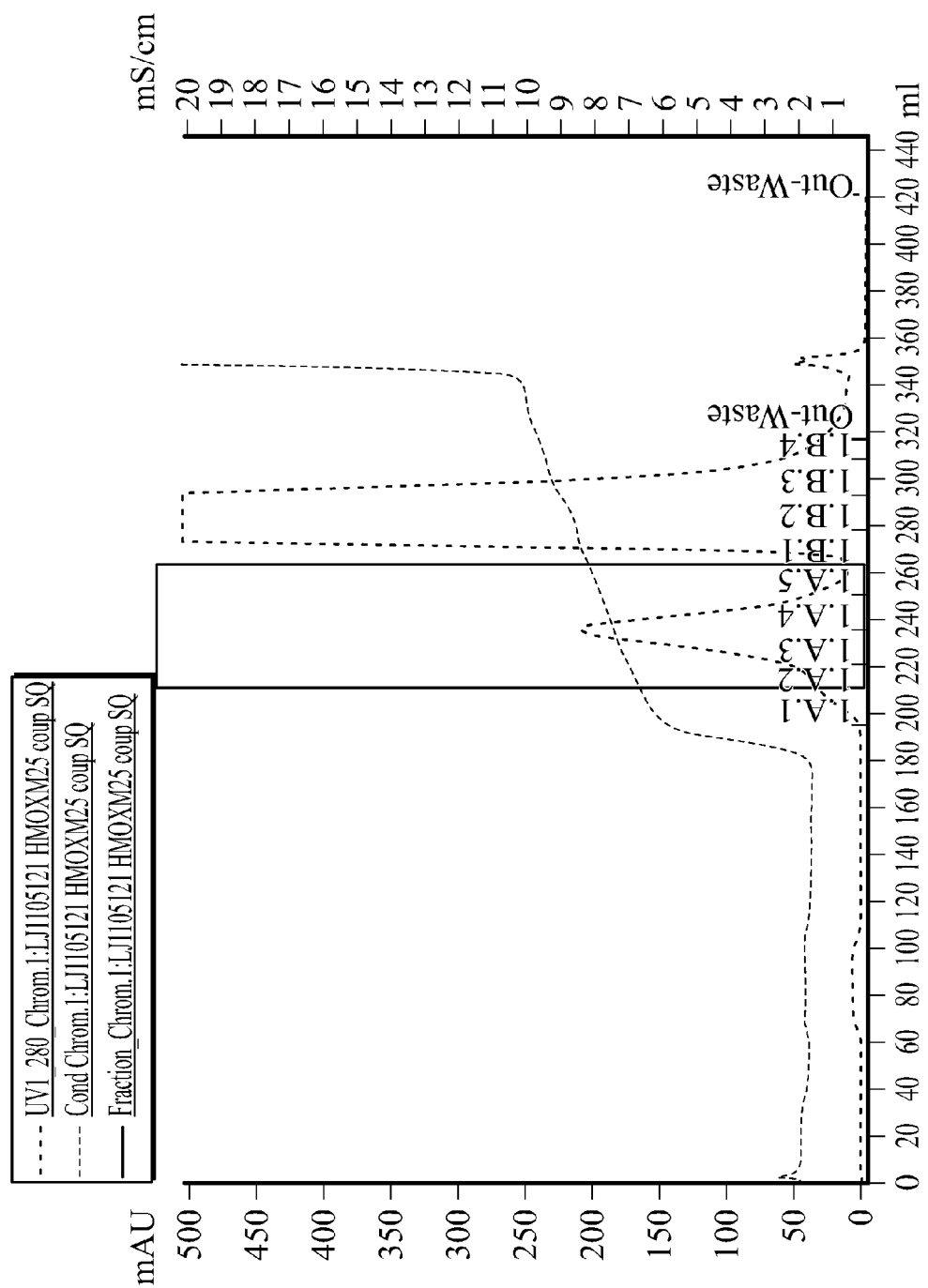
FIG. 10b is a graph showing the result of purifying conjugates including oxyntomodulin derivative (SEQ ID NO. 25) and immunoglobulin Fc through a Source 15Q purification column.
Figure 10C:
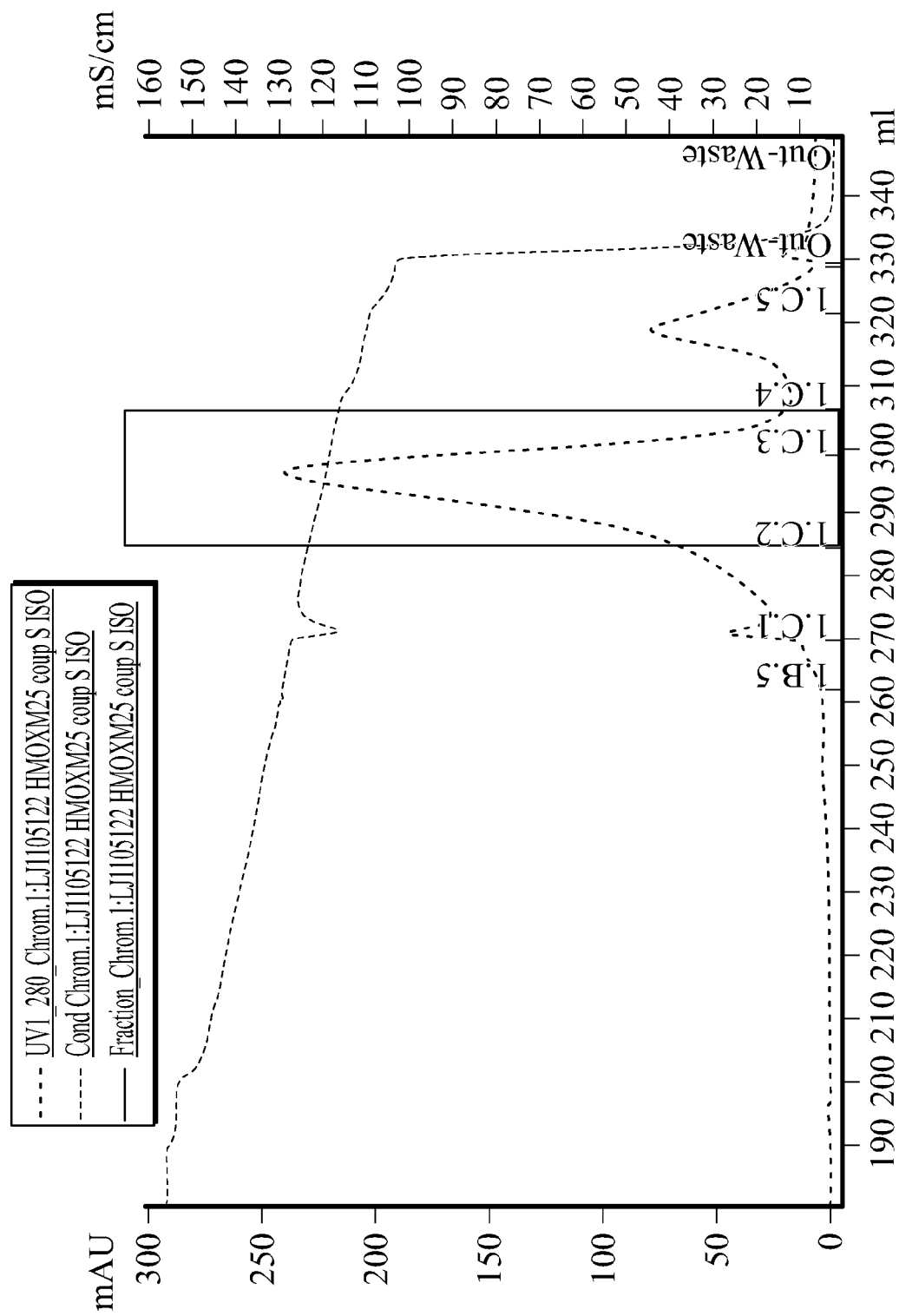
FIG. 10c is a graph showing the result of purifying conjugates including oxyntomodulin derivative (SEQ ID NO. 25) and immunoglobulin Fc through a SOURCE ISO purification column.

Next, the purified mono-PEGylated oxyntomodulin derivative (SEQ ID NO. 25) and immunoglobulin Fc were reacted at a molar ratio of 1:5 with the protein concentration of 20 mg/ml at 4° C. for 16 hours. At this time, the reaction was conducted in 100 mM potassium phosphate buffer (pH 6.0) and 20 mM SCB was added thereto as a reducing agent. After completion of the reaction, the reaction mixture was applied to a SOURCE 15Q purification column (column: SOURCE 15Q, flow rate: 2.0 ml/min, gradient: A 0→4% 1 min B→20% 80 min B (A: 20 mM Tris-HCl, pH 7.5, B: A+1M NaCl)) (FIG. 10b) and a Source ISO purification column (column: SOURCE ISO, flow rate: 2.0 ml/min, gradient: B 0→100% 100 min A, (A: 20 mM Tris-HCl, pH 7.5, B: A+1.1M AS)) (FIG. 10c) to purify conjugates including oxyntomodulin derivative (SEQ ID NO. 25) and immunoglobulin Fc. FIG. 10b is a graph showing the result of purifying conjugates including oxyntomodulin derivative (SEQ ID NO. 25) and immunoglobulin Fc through a SOURCE 15Q purification column, and FIG. 10c is a graph showing the result of purifying conjugates including oxyntomodulin derivative (SEQ ID NO. 25) and immunoglobulin Fc through a Source ISO purification column.

Figure 11A:
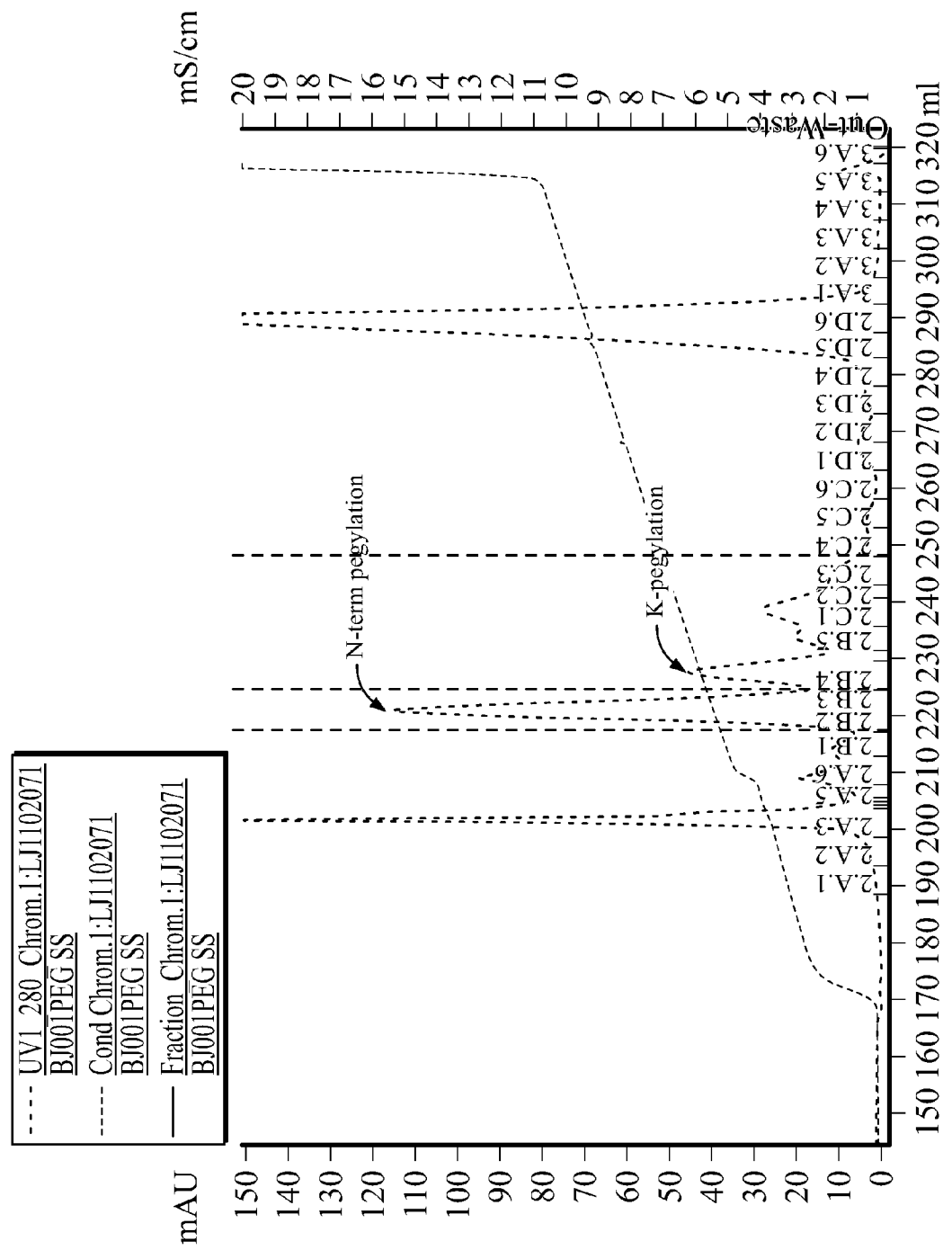
FIG. 11a is a graph showing the result of purifying a mono-PEGylated oxyntomodulin derivative (SEQ ID NO. 28) through a SOURCE S purification column.

Example 13: Preparation of Conjugates Including Oxyntomodulin Derivative (SEQ ID NO. 28) and Immunoglobulin Fc Firstly, for PEGylation of lysine residue at position 20 of the amino acid sequence of oxyntomodulin derivative (SEQ ID NO. 28) with 3.4 K PropionALD(2) PEG, the oxyntomodulin derivative (SEQ ID NO. 28) and MAL-10K-ALD PEG were reacted at a molar ratio of 1:5 with the protein concentration of 3 mg/ml at 4° C. for 3 hours. At this time, the reaction was conducted in 50 mM Na-Borate buffer (pH 9.0) and 2M guanidine was added thereto. After completion of the reaction, the reaction mixture was applied to a SOURCE Spurification column to purify the oxyntomodulin derivative having mono-pegylated lysine (column: SOURCE S, flow rate: 2.0 ml/min, gradient: A 0→3% 1 min B→40% 222 min B (A: 20 mM Na-citrate, pH 3.0+45% ethanol, B: A+1M KCl)) (FIG. 11a). FIG. 11a is a graph showing the result of purifying a mono-PEGylated oxyntomodulin derivative (SEQ ID NO. 28) through a SOURCE S purification column.

Figure 11B:
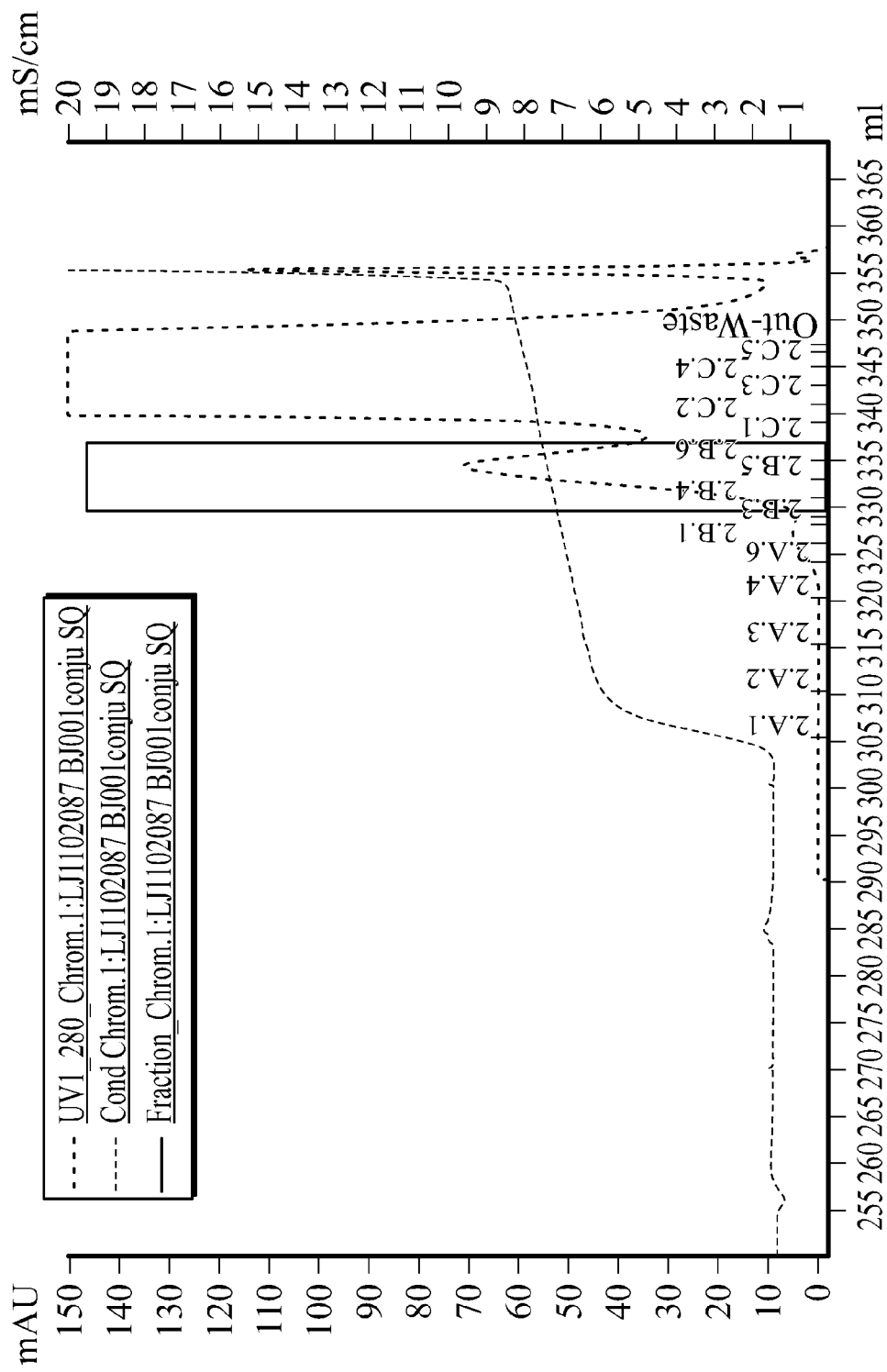
FIG. 11b is a graph showing the result of purifying conjugates including oxyntomodulin derivative (SEQ ID NO. 28) and immunoglobulin Fc through a Source 15Q purification column.
Figure 11C:
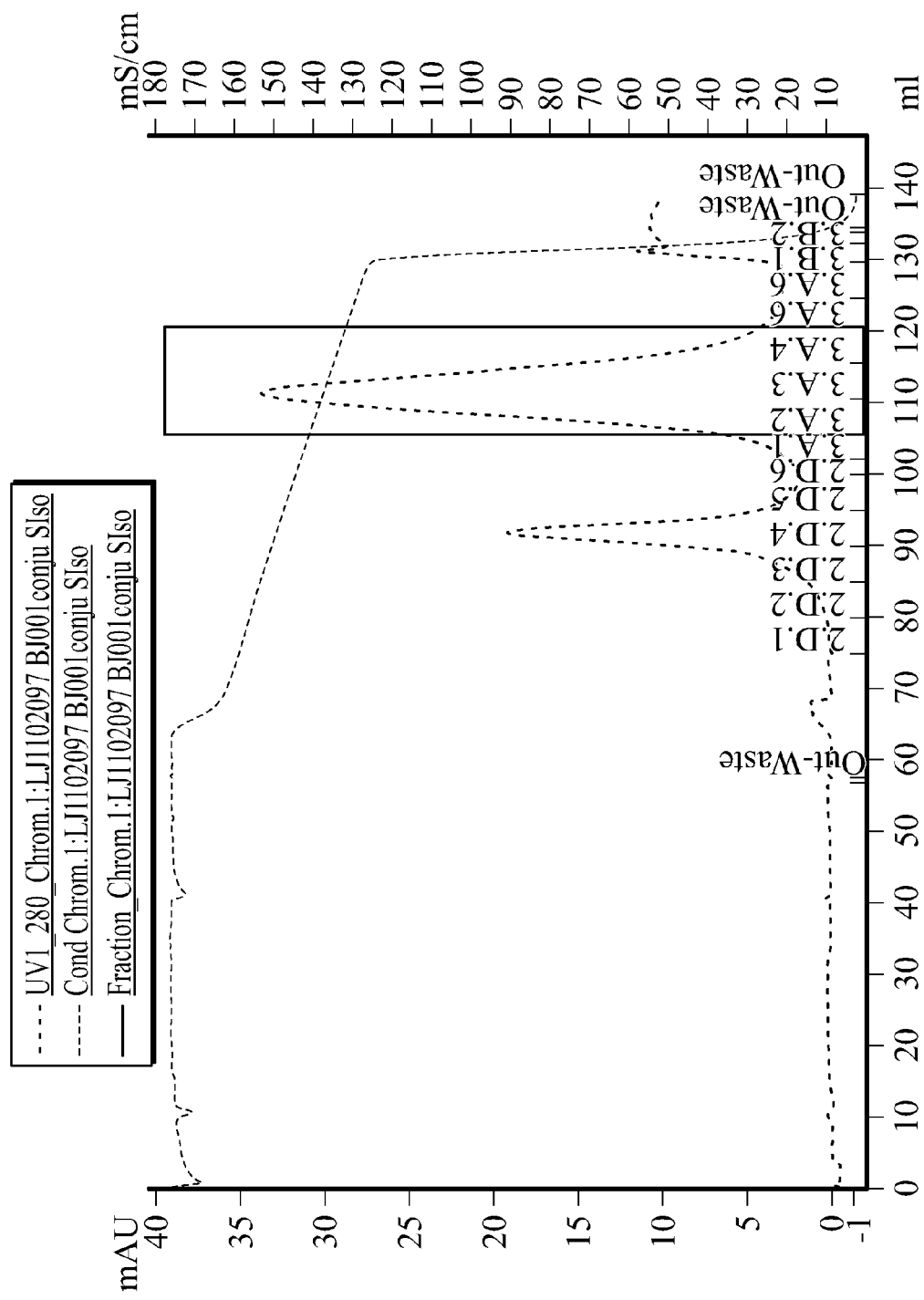
FIG. 11c is a graph showing the result of purifying conjugates including oxyntomodulin derivative (SEQ ID NO. 28) and immunoglobulin Fc through a SOURCE ISO purification column.

Next, the purified mono-PEGylated oxyntomodulin derivative (SEQ ID NO. 28) and immunoglobulin Fc were reacted at a molar ratio of 1:10 with the protein concentration of 20 mg/ml at 4° C. for 16 hours. At this time, the reaction was conducted in 100 mM potassium phosphate buffer (pH 6.0) and 20 mM SCB was added thereto as a reducing agent. After completion of the reaction, the reaction mixture was applied to a SOURCE 15Q purification column (column: SOURCE 15Q, flow rate: 2.0 ml/min, gradient: A 0→4% 1 min B→20% 80 min B (A: 20 mM Tris-HCl, pH 7.5, B: A+1M NaCl)) (FIG. 11b) and a Source ISO purification column (column: SOURCE ISO, flow rate: 2.0 ml/min, gradient: B 0→100% 100 min A, (A: 20 mM Tris-HCl, pH 7.5, B: A+1.1M AS)) (FIG. 11c) to purify conjugates including oxyntomodulin derivative (SEQ ID NO. 28) and immunoglobulin Fc. FIG. 11b is a graph showing the result of purifying conjugates including oxyntomodulin derivative (SEQ ID NO. 28) and immunoglobulin Fc through a SOURCE 15Q purification column, and FIG. 11c is a graph showing the result of purifying conjugates including oxyntomodulin derivative (SEQ ID NO. 28) and immunoglobulin Fc through a Source ISO purification column.

Example 14: Preparation of Conjugates Including Oxyntomodulin Derivative (SEQ ID NO. 32) and Immunoglobulin Fc Firstly, for PEGylation of cysteine residue at position 30 of the amino acid sequence of oxyntomodulin derivative (SEQ ID NO. 32) with MAL-10K-ALD PEG, the oxyntomodulin derivative (SEQ ID NO. 32) and MAL-10K-ALD PEG were reacted at a molar ratio of 1:3 with the protein concentration of 1 mg/ml at room temperature for 3 hours. At this time, the reaction was conducted in 50 mM Tris buffer (pH 8.0) and 2M guanidine was added thereto. After completion of the reaction, the reaction mixture was applied to a SOURCE Spurification column to purify the oxyntomodulin derivative having mono-pegylated cysteine (column: SOURCE S, flow rate: 2.0 ml/min, gradient: A 0→100% 50 min B (A: 20 mM Na-citrate, pH 3.0+45% ethanol, B: A+1M KCl)).

Next, the purified mono-PEGylated oxyntomodulin derivative (SEQ ID NO. 32) and immunoglobulin Fc were reacted at a molar ratio of 1:8 with the protein concentration of 20 mg/ml at 4° C. for 16 hours. At this time, the reaction was conducted in 100 mM potassium phosphate buffer (pH 6.0) and 20 mM SCB was added thereto as a reducing agent. After completion of the reaction, the reaction mixture was applied to a SOURCE 15Q purification column (column: SOURCE 15Q, flow rate: 2.0 ml/min, gradient: A 0→4% 1 min B→20% 80 min B (A: 20 mM Tris-HCl, pH 7.5, B: A+1M NaCl)) and a Source ISO purification column (column: SOURCE ISO, flow rate: 2.0 ml/min, gradient: B 0→100% 100 min A, (A: 20 mM Tris-HCl, pH 7.5, B: A+1.1M AS)) to purify conjugates including oxyntomodulin derivative (SEQ ID NO. 32) and immunoglobulin Fc.

Example 15: Preparation of Conjugates Including Oxyntomodulin Derivative (SEQ ID NO. 33) and Immunoglobulin Fc Firstly, for PEGylation of cysteine residue at position 30 of the amino acid sequence of oxyntomodulin derivative (SEQ ID NO. 33) with MAL-10K-ALD PEG, the oxyntomodulin derivative (SEQ ID NO. 33) and MAL-10K-ALD PEG were reacted at a molar ratio of 1:1 with the protein concentration of 1 mg/ml at room temperature for 3 hours. At this time, the reaction was conducted in 50 mM Tris buffer (pH 8.0) and 2M guanidine was added thereto. After completion of the reaction, the reaction mixture was applied to a SOURCE Spurification column to purify the oxyntomodulin derivative having mono-pegylated cysteine (column: SOURCE S, flow rate: 2.0 ml/min, gradient: A 0→100% 50 min B (A: 20 mM Na-citrate, pH 3.0+45% ethanol, B: A+1M KCl)).

Next, the purified mono-PEGylated oxyntomodulin derivative (SEQ ID NO. 33) and immunoglobulin Fc were reacted at a molar ratio of 1:5 with the protein concentration of 20 mg/ml at 4° C. for 16 hours. At this time, the reaction was conducted in 100 mM potassium phosphate buffer (pH 6.0) and 20 mM SCB was added thereto as a reducing agent. After completion of the reaction, the reaction mixture was applied to a SOURCE 15Q purification column (column: SOURCE 15Q, flow rate: 2.0 ml/min, gradient: A 0→4% 1 min B→20% 80 min B (A: 20 mM Tris-HCl, pH 7.5, B: A+1M NaCl)) and a Source ISO purification column (column: SOURCE ISO, flow rate: 2.0 ml/min, gradient: B 0→100% 100 min A, (A: 20 mM Tris-HCl, pH 7.5, B: A+1.1M AS)) to purify conjugates including oxyntomodulin derivative (SEQ ID NO. 33) and immunoglobulin Fc.

Example 16: Preparation of Conjugates Including Oxyntomodulin Derivative (SEQ ID NO. 34) and Immunoglobulin Fc Firstly, for PEGylation of cysteine residue at position 30 of the amino acid sequence of oxyntomodulin derivative (SEQ ID NO. 34) with MAL-10K-ALD PEG, the oxyntomodulin derivative (SEQ ID NO. 34) and MAL-10K-ALD PEG were reacted at a molar ratio of 1:1 with the protein concentration of 3 mg/ml at room temperature for 3 hours. At this time, the reaction was conducted in 50 mM Tris buffer (pH 8.0) and 1M guanidine was added thereto. After completion of the reaction, the reaction mixture was applied to a SOURCE Spurification column to purify the oxyntomodulin derivative having mono-pegylated cysteine (column: SOURCE S, flow rate: 2.0 ml/min, gradient: A 0→100% 50 min B (A: 20 mM Na-citrate, pH 3.0+45% ethanol, B: A+1M KCl)).

Next, the purified mono-PEGylated oxyntomodulin derivative (SEQ ID NO. 34) and immunoglobulin Fc were reacted at a molar ratio of 1:5 with the protein concentration of 20 mg/ml at 4° C. for 16 hours. At this time, the reaction was conducted in 100 mM potassium phosphate buffer (pH 6.0) and 20 mM SCB was added thereto as a reducing agent. After completion of the reaction, the reaction mixture was applied to a SOURCE 15Q purification column (column: SOURCE 15Q, flow rate: 2.0 ml/min, gradient: A 0→4% 1 min B→20% 80 min B (A: 20 mM Tris-HCl, pH 7.5, B: A+1M NaCl)) and a Source ISO purification column (column: SOURCE ISO, flow rate: 2.0 ml/min, gradient: B 0→100% 100 min A, (A: 20 mM Tris-HCl, pH 7.5, B: A+1.1M AS)) to purify conjugates including oxyntomodulin derivative (SEQ ID NO. 34) and immunoglobulin Fc.

Example 17: In Vitro Activity of Oxyntomodulin Derivative-Immunoglobulin Fc Conjugates In order to measure anti-obesity efficacies of the conjugates including the oxyntomodulin or oxyntomodulin derivative and the immunoglobulin Fc that were prepared in the above Examples, experiments were performed in the same manner as in Example 2-2.

Specifically, each of the transformants prepared in Examples 1-1 and 1-2 was sub-cultured two or three times a week, and aliquoted in each well of a 96-well plate at a density of $1 \times 10^5$, followed by cultivation for 24 hours. Each of the cultured transformants was washed with KRB buffer and suspended in 40 ml of KRB buffer containing 1 mM IBMX, and left at room temperature for 5 minutes. GLP-1, glucagon, and oxyntomodulin derivative (SEQ ID NO. 23, 24, 25, 32, 33 or 34)-immunoglobulin Fc conjugates were diluted from 1000 nM to 0.02 nM by 5-fold serial dilution, and each 40 ml thereof was added to each transformant, and cultured at 37° C. for 1 hour in a $CO_2$ incubator. Then, 20 ml of cell lysis buffer was added for cell lysis, and the cell lysates were applied to a cAMP assay kit (Molecular Device, USA) to measure cAMP concentrations using a Victor (PERKIN ELMER®, USA). $EC_{50}$ values were calculated therefrom, and compared to each other (Table 3).

TABLE 3

In vitro activity of oxyntomodulin derivative-immunoglobulin Fc conjugates

| SEQ ID NO. | $EC_{50}$ (nM) | |
|---|---|---|
| | CHO/GLP-1R | CHO/GCGR |
| GLP-1 | 1.7 ± 0.82 | >1,000 |
| Glucagon | >1,000 | 1.7 ± 1.69 |
| SEQ ID NO. 23 - Fc conjugates | 5.4 | 15.8 |
| SEQ ID NO. 24 - Fc conjugates | 8.4 | 76.8 |
| SEQ ID NO. 25 - Fc conjugates | 5.5 | 9.4 |
| SEQ ID NO. 32 - Fc conjugates | 68.7 | 11.9 |
| SEQ ID NO. 33 - Fc conjugates | 11.7 | 85.9 |
| SEQ ID NO. 34 - Fc conjugates | 168.0 | 8.0 |

As shown in Table 3, the oxyntomodulin derivative-immunoglobulin Fc conjugates were found to show the in vitro activity to GLP-1 and glucagon receptors.

Example 18: In Vivo Activity of Oxyntomodulin Derivative-Immunoglobulin Conjugates It was examined whether the oxyntomodulin derivative-immunoglobulin Fc conjugates show excellent body weight-reducing effects in vivo.

Figure 13:
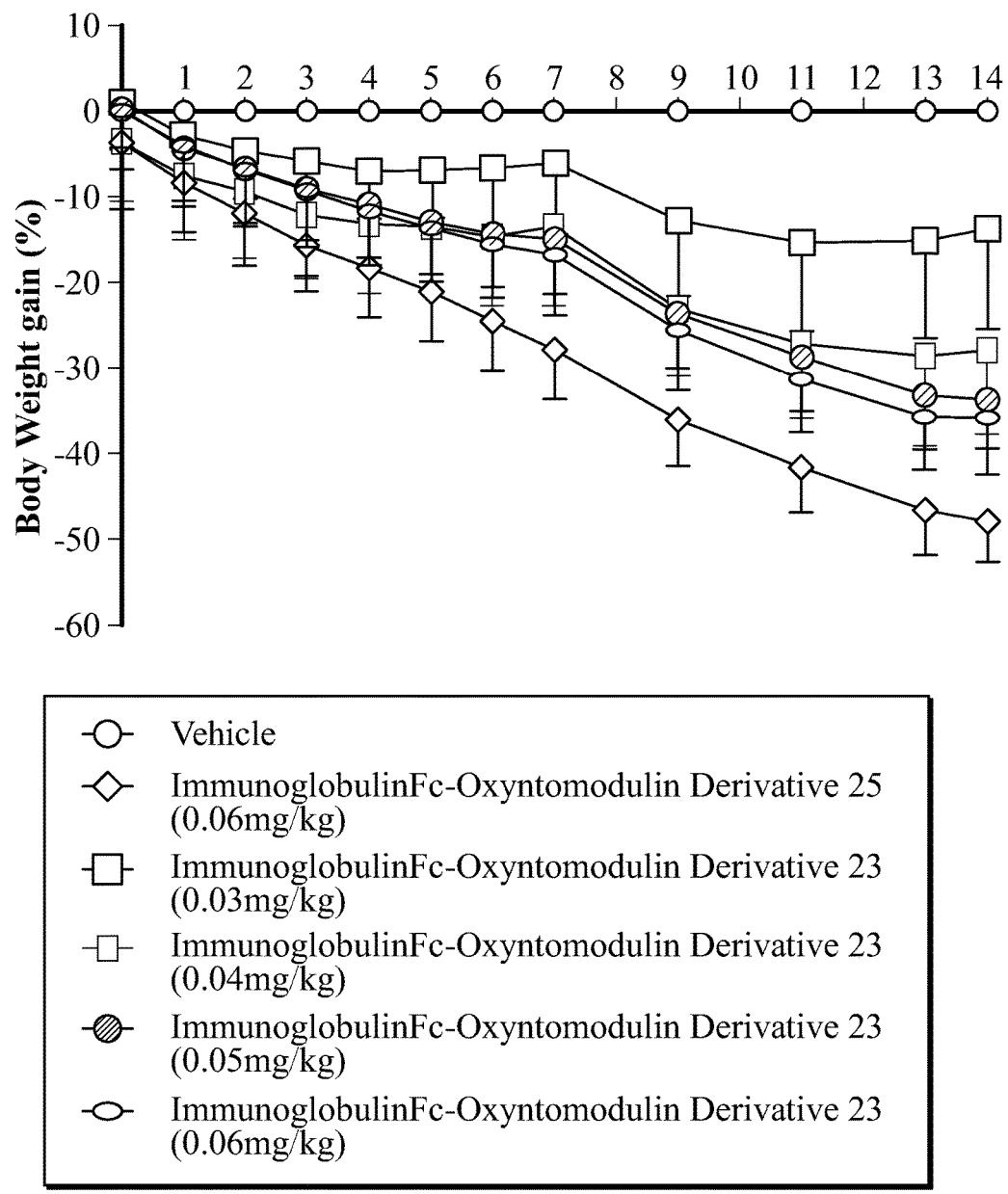
FIG. 13 is a graph showing changes in body weight of mice according to the type and administration dose of oxyntomodulin derivative-immunoglobulin Fc conjugates.

Specifically, 6-week-old normal C57BL/6 mice were fed a high fat diet of 60 kcal for 24 weeks to increase their body weight by approximately 50 g on average, and subcutaneously administered with oxyntomodulin derivative (SEQ ID NO. 23, 24 or 25)-immunoglobulin Fc conjugates at a dose of 0.03 or 0.06 mg/kg/week for 3 weeks. Thereafter, changes in the body weight of the mice were measured (FIG. 12 and FIG. 13). FIG. 12 and FIG. 13 are graphs showing changes in body weight of mice according to the type and administration dose of oxyntomodulin derivative-immunoglobulin Fc conjugates. As shown in FIG. 12 and FIG. 13, as the administration dose of the oxyntomodulin derivative-immunoglobulin Fc conjugates was increased, the body weight was reduced in direct proportion, even though there were differences between the types of the oxyntomodulin derivative-immunoglobulin Fc conjugates, suggesting that the oxyntomodulin derivative-immunoglobulin Fc conjugates reduce the body weight in a dose-dependent manner.

The invention claimed is:

1. A conjugate comprising:
 an oxyntomodulin derivative comprising the amino acid sequence of SEQ ID NO: 33;
 an immunoglobulin Fc region; and
 a non-peptidyl polymer, wherein the non-peptidyl polymer links the oxyntomodulin derivative and the immunoglobulin Fc region via covalent bonds.

2. The conjugate according to claim 1, wherein the oxyntomodulin derivative activates glucagon-like peptide-1 receptor, glucagon receptor, or both.

3. The conjugate according to claim 1, wherein the conjugate has anti-obesity effects.

4. The conjugate according to claim 1, wherein the non-peptidyl polymer is polyethylene glycol, polypropylene glycol, an ethylene glycol-propylene glycol copolymer, a polyoxyethylated polyol, polyvinyl alcohol, a polysaccharide, polyvinyl ethyl ether, polylactic acid, polylacticglycolic acid, a lipid polymer, hyaluronic acid, or combinations thereof.

5. The conjugate according to claim 4, wherein the non-peptidyl polymer is polyethylene glycol.

6. The conjugate according to claim 4, wherein the polysaccharide is dextran, a chitin, or a combination thereof.

7. The conjugate according to claim 1, wherein an amine group or a thiol group of the immunoglobulin Fc region is attached to one end of the non-peptidyl polymer and an amine group or a thiol group of the oxyntomodulin derivative is attached to the other end of the non-peptidyl polymer.

8. The conjugate according to claim 1, wherein the conjugate is prepared by covalently linking the oxyntomodulin derivative to the immunoglobulin Fc region via the non-peptidyl polymer, the non-peptidyl polymer having, prior to forming the conjugate, reactive functional groups at both ends.

9. The conjugate according to claim 8, wherein the reactive functional groups are an aldehyde group, a maleimide group, a succinimide derivative, or combinations thereof.

10. The conjugate according to claim 1, wherein the immunoglobulin Fc region is a non-glycosylated Fc region.

11. The conjugate according to claim 1, wherein the immunoglobulin Fc region is a heavy-chain constant region 1 (CH1) domain, a heavy-chain constant region 2 (CH2) domain, a heavy-chain constant region 3 (CH3) domain and a heavy-chain constant region 4 (CH4) domain; a CH1 domain and a CH2 domain; a CH1 domain and a CH3 domain; a CH2 domain and a CH3 domain; a combination of one or more domains and an immunoglobulin hinge region or a portion of the hinge region; or a dimer of each domain of the heavy-chain constant regions and the light-chain constant region.

12. The conjugate according to claim 1, wherein the immunoglobulin Fc region comprises a modification of a native Fc region comprising: (i) an amino acid modification to prevent formation of a disulfide bond; (ii) elimination of one or more amino acid residues from the N-terminal end of the native Fc region; (iii) addition of a methionine residue to the N-terminal end of the Fc region; (iv) deletion of a complement-binding site; or (v) deletion of an antibody dependent cell mediated cytotoxicity (ADCC) site.

13. The conjugate according to claim 1, wherein the immunoglobulin Fc region is an Fc region from an immunoglobulin G, immunoglobulin A, immunoglobulin D, immunoglobulin E, or immunoglobulin M.

14. The conjugate according to claim 13, wherein the immunoglobulin Fc region is an IgG4 Fc region.

15. The conjugate according to claim 1, wherein the immunoglobulin Fc region is a human IgG4-derived non-glycosylated Fc region.

16. The conjugate of claim 1, wherein the non-peptidyl polymer is linked via a covalent bond to the oxyntomodulin derivative at a cysteine residue.

17. A pharmaceutical composition comprising the conjugate of claim 1 and a pharmaceutically acceptable carrier.

18. The pharmaceutical composition according to claim 17, further comprising a glucagon-like peptide-1 receptor agonist, a leptin receptor agonist, a dipeptidyl peptidase-IV inhibitor, a Y5 receptor antagonist, a melanin-concentrating hormone receptor antagonist, a Y2/3 receptor agonist, a MC3/4 receptor agonist, a gastric/pancreatic lipase inhibitor, a 5HT2c agonist, a β3A receptor agonist, an amylin receptor agonist, a ghrelin antagonist, or a ghrelin receptor antagonist.

19. A method for treating obesity, comprising administering the conjugate of claim 1 to a subject in need thereof.

20. The method of claim 19, which further comprises administering a glucagon-like peptide-1 receptor agonist, a leptin receptor agonist, a dipeptidyl peptidase-IV inhibitor, a Y5 receptor antagonist, a melanin-concentrating hormone receptor antagonist, a Y2/3 receptor agonist, a MC3/4 receptor agonist, a gastric/pancreatic lipase inhibitor, a 5HT2c agonist, a β3A receptor agonist, an amylin receptor agonist, a ghrelin antagonist, or a ghrelin receptor antagonist.

* * * * *